(12) United States Patent
Wiley

(10) Patent No.: US 7,482,430 B2
(45) Date of Patent: *Jan. 27, 2009

(54) COMPOSITIONS AND METHODS RELATING TO MULTIMERIC AND OLIGOMERIC SOLUBLE FRAGMENTS OF THE TWEAK RECEPTOR

(75) Inventor: Steven R. Wiley, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 238 days.

This patent is subject to a terminal disclaimer.

(21) Appl. No.: 10/898,575

(22) Filed: Jul. 23, 2004

(65) Prior Publication Data

US 2005/0054047 A1  Mar. 10, 2005

Related U.S. Application Data

(60) Provisional application No. 60/490,036, filed on Jul. 24, 2003.

(51) Int. Cl.
*A61J 38/00* (2006.01)
*A61K 39/00* (2006.01)
*C07K 14/00* (2006.01)

(52) U.S. Cl. .................. 530/350; 530/300; 424/192.1; 514/2; 514/12

(58) Field of Classification Search ................ None
See application file for complete search history.

(56) References Cited

U.S. PATENT DOCUMENTS

| | | | |
|---|---|---|---|
| 5,759,546 A | 6/1998 | Weinberg et al. | |
| 6,207,642 B1 | 3/2001 | Wiley | |
| 6,531,447 B1 | 3/2003 | Ruben et al. | |
| 6,727,225 B2 | 4/2004 | Wiley | |
| 6,824,773 B2 | 11/2004 | Wiley | |
| 2002/0015703 A1 | 2/2002 | Rennert | |
| 2002/0041876 A1* | 4/2002 | Wiley | 424/145.1 |
| 2003/0105297 A1 | 6/2003 | Rubin et al. | |
| 2004/0253610 A1 | 12/2004 | Wiley | |

FOREIGN PATENT DOCUMENTS

| | | |
|---|---|---|
| WO | WO 94 10308 | 5/1994 |
| WO | WO98/35061 | 8/1998 |
| WO | WO98/54206 | 12/1998 |
| WO | WO98/55508 | 12/1998 |
| WO | WO99/19490 | 4/1999 |
| WO | WO99/61471 | 12/1999 |
| WO | WO00/06698 | 2/2000 |
| WO | WO00/42073 | 7/2000 |
| WO | WO 01/45730 A3 | 6/2001 |
| WO | WO/01/85193 A2 | 11/2001 |
| WO | WO/02/22166 A2 | 3/2002 |

OTHER PUBLICATIONS

Mickle J.E. et al. Genotype-phenotype relationships in cystic fibrosis. 2000. Med. Clin. North Am. vol. 84, No. 3, pp. 597-607.*
Engel, J, et al. What are oligomerization domains good for? Matrix Biology, 2000, vol. 19, pp. 283-288.*

Han et al. TNF-related weak inducer of apoptosis receptor, a TNF receptor superfamily member, activates NF-kB through TNF receptor-associated factors. Biochem. Biophys. Res. Comm. 2003. vol. 305, pp. 789-796.*
U.S. Appl. No. 10/862,109, filed Jun. 4, 2004, Wiley, S.F.
U.S. Appl. No. 10/971,250, filed Oct. 22, 2004, Wiley et al.
Schreiber Martha, et al., "Myxoma virus T2 protein, a tumor necrosis factor (TNF) receptor homolog, is secreted as a monomer and dimer that each bind rabbit TNF-alpha, but the dimer is a more potent TNF inhibitor," *J. of Biological Chemistry*, 271(23) 13333-13341, 1996. (abstract).
Howard O.M Zack, et al., "Soluble tumor necrosis factor receptor: Inhibition of human immunodeficiency virus activation," *Proceedings of the National Academy of Sciences of the U S.A.*, 90(6):2335-2339, 1993 (abstract).
Collette Y., et al. "A co-evolution perspective of the TNFSF and TNFRSF families in the immune system,". *Trends in Immunology*, Elsevier, Cambridge, GB, 24(7):387-394, Jul. 2003.
Bu Rongfa et al., "Expression and function of TNF-family protiens and receptors in human osteoblasts," *BONE* (New York), 33(5):760-770, Nov. 2003 (abstract).
Chicheportiche Y, et al., "TWEAK, A New Secreted Ligand In The Tumor Necrosis Factor Family That Weakly Induces Apoptosis," *Biological Chem.* 272 (51):32401-32410, 1997.
Feng S-L Y, et al. "The Fn14 Immediate-Early Response Gene is Induced During Liver Regeneration and Highly Expressed in Both Human and Murine Hepatocellular Carcinomas," *Am. J. Pathology* 156 (4):1253-1261, Apr. 2000.
Kaplau MJ, et al. "Th2 Lymphocytes Kil.1 Antigen Presenting Macrophages Through a TWEAK Dependent Pathway," *J. Invest. Med. US, Am. Fed for Clinical Research* 46:287A, 1998 (abstract).
Lynch CN et al., "TWEAK Induces Angiogenesis and Proliferation of Endothelial Cells," *Biological Chem.* 274 (13):8455-8459, 1999.
Marsters SA, et al., "Identification of a Ligand for the Death-Domain-Containing Receptor Apo3," *Current Biology* 8 (9):525-528, 1998.
Meighan-Mantha RL, et al. "The Mitogen-inducible *Fn14* Gene Encoded a Type I Transmembrane Protein that Modulates Fibroblast Adhesion and Migration," *J. Bio. Chem* 274(46):33166-33176, Nov. 1999.
Schneider P., et al., "TWEAK Can Induce Cell Death Via Endogenous TNF And TNF Receptor 1," *Eur. J. Immunol.* 29:1785-1792, 1999.
Tanaka S. and Sugimachi K., Human Homologue of Fn14, "DDBJ/EMBL/GenBank databases; AB035480," Dec. 2, 1999.
Chicheportiche et al., "Proinflammatory activity of TWEAK on human dermal fibroblasts and synoviocytes: blocking and enhancing effect of anti-TWEAK monoclonal antibodies," *Arthritis Res* 4:126-133, 2002.
Jakubowski et al., "Dual role for TWEAK in angiogenic regulation," *Journal of Cell Science* 115:267-274, 2002.

* cited by examiner

*Primary Examiner*—Robert Landsman
*Assistant Examiner*—Bruce D. Hissong
(74) *Attorney, Agent, or Firm*—Nathan A. Machin

(57) ABSTRACT

The present invention provides methods and compositions relating to fusion proteins comprising multimeric soluble TWEAK receptor fragments and an oligomerization domain. Such fusion proteins are useful for antagonizing the TWEAK receptor and for treating diseases or conditions mediated by angiogenesis, such as solid tumors and inflammatory conditions.

37 Claims, 12 Drawing Sheets

```
  1 MAPGWPRSLPQILVLGFGLVLMRAAAGEQAPGTSPCSSGSSWSADLDKCM   50
    ||   |   ||| |||  |||  ||||||||| |||| |||||||||||
  1 MARGSLRLLRLLVLGLWLALLRSVAGEQAPGTAPCSRGSSWSADLDKCM    50

51 DCASCPARPHSDFCLGCAAAPPAHFRLLWPILGGALSLVLVLALVSSFLV  100
    |||||| ||||||||||||||||| |||||||||||||| | |  ||||
 51 DCASCRARPHSDFCLGCAAAPPAPFRLLWPILGGALSLTFVLGLLSGFLV  100

101 WRRCRRREKFTTPIEETGGEGCPGVALIQ  129
    |||||||||||||||||||| ||| ||||
101 WRRCRRREKFTTPIEETGGEGCPAVALIQ  129
```

Fig. 1

```
                           SEQUENCE LISTING

<160> NUMBER OF SEQ ID NOS: 45

<210> SEQ ID NO 1
<211> LENGTH: 898
<212> TYPE: DNA
<213> ORGANISM: Artificial Sequence
<220> FEATURE:
<223> OTHER INFORMATION: LZ-TWEAK
<220> FEATURE:
<221> NAME/KEY: CDS
<222> LOCATION: (52)..(873)

<400> SEQUENCE: 1
tctcgagggc cacgcgttta aacgtcgagg tacctatccc gggccgccac c atg gct       57
                                                        Met Ala
                                                        1 aca ggc tcc cgg acg tcc ctg ctc ctg gct ttt ggc ctg ctc tgc ctg      105
Thr Gly Ser Arg Thr Ser Leu Leu Leu Ala Phe Gly Leu Leu Cys Leu
         5                  10                  15 ccc tgg ctt caa gag ggc agt gca act agt tct gac cgt atg aaa cag      153
Pro Trp Leu Gln Glu Gly Ser Ala Thr Ser Ser Asp Arg Met Lys Gln
 20                  25                  30 ata gag gat aag atc gaa gag atc cta agt aag att tat cat ata gag      201
Ile Glu Asp Lys Ile Glu Glu Ile Leu Ser Lys Ile Tyr His Ile Glu
35                  40                  45                  50 aat gaa atc gcc cgt atc aaa aag ctg att ggc gag cgg act aga tct      249
Asn Glu Ile Ala Arg Ile Lys Lys Leu Ile Gly Glu Arg Thr Arg Ser
                 55                  60                  65 agt ttg ggg agc cgg gca tcg ctg tcc gcc cag gag cct gcc cag gag      297
Ser Leu Gly Ser Arg Ala Ser Leu Ser Ala Gln Glu Pro Ala Gln Glu
             70                  75                  80 gag ctg gtg gca gag gag gac cag gac ccg tcg gaa ctg aat ccc cag      345
Glu Leu Val Ala Glu Glu Asp Gln Asp Pro Ser Glu Leu Asn Pro Gln
         85                  90                  95 aca gaa gaa agc cag gat cct gcg cct ttc ctg aac cga cta gtt cgg      393
Thr Glu Glu Ser Gln Asp Pro Ala Pro Phe Leu Asn Arg Leu Val Arg
    100                 105                 110 cct cgc aga agt gca cct aaa ggc cgg aaa aca cgg gct cga aga gcg      441
Pro Arg Arg Ser Ala Pro Lys Gly Arg Lys Thr Arg Ala Arg Arg Ala
115                 120                 125                 130 atc gca gcc cat tat gaa gtt cat cca cga cct gga cag gac gga gcg      489
Ile Ala Ala His Tyr Glu Val His Pro Arg Pro Gly Gln Asp Gly Ala
                135                 140                 145 cag gca ggt gtg gac ggg aca gtg agt ggc tgg gag gaa gcc aga atc      537
Gln Ala Gly Val Asp Gly Thr Val Ser Gly Trp Glu Glu Ala Arg Ile
            150                 155                 160 aac agc tcc agc cct ctg cgc tac aac cgc cag atc ggg gag ttt ata      585
Asn Ser Ser Ser Pro Leu Arg Tyr Asn Arg Gln Ile Gly Glu Phe Ile
        165                 170                 175 gtc acc cgg gct ggg ctc tac tac ctg tac tgt cag gtg cac ttt gat      633
Val Thr Arg Ala Gly Leu Tyr Tyr Leu Tyr Cys Gln Val His Phe Asp
```

```
                    180                 185                 190
gag ggg aag gct gtc tac ctg aag ctg gac ttg ctg gtg gat ggt gtg       681
Glu Gly Lys Ala Val Tyr Leu Lys Leu Asp Leu Leu Val Asp Gly Val
195                 200                 205                 210 ctg gcc ctg cgc tgc ctg gag gaa ttc tca gcc act gcg gcc agt tcc       729
Leu Ala Leu Arg Cys Leu Glu Glu Phe Ser Ala Thr Ala Ala Ser Ser
                215                 220                 225 ctc ggg ccc cag ctc cgc ctc tgc cag gtg tct ggg ctg ttg gcc ctg       777
Leu Gly Pro Gln Leu Arg Leu Cys Gln Val Ser Gly Leu Leu Ala Leu
            230                 235                 240 cgg cca ggg tcc tcc ctg cgg atc cgc acc ctc ccc tgg gcc cat ctc       825
Arg Pro Gly Ser Ser Leu Arg Ile Arg Thr Leu Pro Trp Ala His Leu
        245                 250                 255 aag gct gcc ccc ttc ctc acc tac ttc gga ctc ttc cag gtt cac tga       873
Lys Ala Ala Pro Phe Leu Thr Tyr Phe Gly Leu Phe Gln Val His
    260                 265                 270 gcggccgcgg atctgtttaa actag                                           898

<210> SEQ ID NO 2
<211> LENGTH: 273
<212> TYPE: PRT
<213> ORGANISM: Artificial Sequence
<220> FEATURE:
<223> OTHER INFORMATION: Synthetic Construct

<400> SEQUENCE: 2

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Thr Ser Ser Asp Arg Met
                20                  25                  30

Lys Gln Ile Glu Asp Lys Ile Glu Glu Ile Leu Ser Lys Ile Tyr His
            35                  40                  45

Ile Glu Asn Glu Ile Ala Arg Ile Lys Lys Leu Ile Gly Glu Arg Thr
        50                  55                  60

Arg Ser Ser Leu Gly Ser Arg Ala Ser Leu Ser Ala Gln Glu Pro Ala
65                  70                  75                  80

Gln Glu Glu Leu Val Ala Glu Asp Gln Asp Pro Ser Glu Leu Asn
                85                  90                  95

Pro Gln Thr Glu Glu Ser Gln Asp Pro Ala Pro Phe Leu Asn Arg Leu
            100                 105                 110

Val Arg Pro Arg Arg Ser Ala Pro Lys Gly Arg Lys Thr Arg Ala Arg
        115                 120                 125

Arg Ala Ile Ala Ala His Tyr Glu Val His Pro Arg Pro Gly Gln Asp
    130                 135                 140

Gly Ala Gln Ala Gly Val Asp Gly Thr Val Ser Gly Trp Glu Glu Ala
145                 150                 155                 160

Arg Ile Asn Ser Ser Ser Pro Leu Arg Tyr Asn Arg Gln Ile Gly Glu
                165                 170                 175

Phe Ile Val Thr Arg Ala Gly Leu Tyr Tyr Leu Tyr Cys Gln Val His
            180                 185                 190

Phe Asp Glu Gly Lys Ala Val Tyr Leu Lys Leu Asp Leu Leu Val Asp
        195                 200                 205

Gly Val Leu Ala Leu Arg Cys Leu Glu Glu Phe Ser Ala Thr Ala Ala
    210                 215                 220

Ser Ser Leu Gly Pro Gln Leu Arg Leu Cys Gln Val Ser Gly Leu Leu
225                 230                 235                 240
```

```
Ala Leu Arg Pro Gly Ser Ser Leu Arg Ile Arg Thr Leu Pro Trp Ala
            245                 250                 255
His Leu Lys Ala Ala Pro Phe Leu Thr Tyr Phe Gly Leu Phe Gln Val
        260                 265                 270
His
```

<210> SEQ ID NO 3
<211> LENGTH: 868
<212> TYPE: DNA
<213> ORGANISM: Homo sapiens
<220> FEATURE:
<221> NAME/KEY: CDS
<222> LOCATION: (53)..(442)

<400> SEQUENCE: 3

```
gcttgaattc aataactata acggtcctaa ggtagcgaag aggacgtgca ct atg gct      58
                                                          Met Ala
                                                            1 cgg ggc tcg ctg cgc cgg ttg ctg cgg ctc ctc gtg ctg ggg ctc tgg      106
Arg Gly Ser Leu Arg Arg Leu Leu Arg Leu Leu Val Leu Gly Leu Trp
        5                   10                  15 ctg gcg ttg ctg cgc tcc gtg gcc ggg gag caa gcg cca ggc acc gcc      154
Leu Ala Leu Leu Arg Ser Val Ala Gly Glu Gln Ala Pro Gly Thr Ala
    20                  25                  30 ccc tgc tcc cgc ggc agc tcc tgg agc gcg gac ctg gac aag tgc atg      202
Pro Cys Ser Arg Gly Ser Ser Trp Ser Ala Asp Leu Asp Lys Cys Met
35                  40                  45                  50 gac tgc gcg tct tgc agg gcg cga ccg cac agc gac ttc tgc ctg ggc      250
Asp Cys Ala Ser Cys Arg Ala Arg Pro His Ser Asp Phe Cys Leu Gly
                55                  60                  65 tgc gct gca gca cct cct gcc ccc ttc cgg ctg ctt tgg ccc atc ctt      298
Cys Ala Ala Ala Pro Pro Ala Pro Phe Arg Leu Leu Trp Pro Ile Leu
            70                  75                  80 ggg ggc gct ctg agc ctg acc ttc gtg ctg ggg ctg ctt tct ggc ttt      346
Gly Gly Ala Leu Ser Leu Thr Phe Val Leu Gly Leu Leu Ser Gly Phe
        85                  90                  95 ttg gtc tgg aga cga tgc cgc agg aga gag aag ttc acc acc ccc ata      394
Leu Val Trp Arg Arg Cys Arg Arg Arg Glu Lys Phe Thr Thr Pro Ile
    100                 105                 110 gag gag acc ggc gga gag ggc tgc cca gct gtg gcg ctg atc cag tga      442
Glu Glu Thr Gly Gly Glu Gly Cys Pro Ala Val Ala Leu Ile Gln
115                 120                 125 caatgtgccc cctgccagcc ggggctcgcc cactcatcat tcattcatcc attctagagc      502
cagtctctgc ctcccagacg cggcgggagc caagctcctc caaccacaag ggggtgggg       562 ggcggtgaat cacctctgag gcctgggccc agggttcagg ggaaccttcc aaggtgtctg      622
gttgccctgc ctctggctcc agaacagaaa gggagcctca cgctggctca cacaaaacag      682
ctgacactga ctaaggaact gcagcatttg cacaggggag ggggtgccc tccttcctag       742 aggccctggg ggccaggctg acttgggggg cagacttgac actaggcccc actcactcag      802
atgtcctgaa attccaccac gggggtcacc ctgggggtt agggacctat ttttaacact       862
agaggg                                                                 868
```

<210> SEQ ID NO 4
<211> LENGTH: 129
<212> TYPE: PRT
<213> ORGANISM: Homo sapiens

<400> SEQUENCE: 4

-continued

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Glu Lys Phe Thr Thr
                100                 105                 110

Pro Ile Glu Glu Thr Gly Gly Glu Gly Cys Pro Ala Val Ala Leu Ile
            115                 120                 125

Gln
```

<210> SEQ ID NO 5
<211> LENGTH: 129
<212> TYPE: PRT
<213> ORGANISM: Mus sp.

<400> SEQUENCE: 5

```
Met Ala Pro Gly Trp Pro Arg Ser Leu Pro Gln Ile Leu Val Leu Gly
1               5                   10                  15

Phe Gly Leu Val Leu Met Arg Ala Ala Ala Gly Glu Gln Ala Pro Gly
            20                  25                  30

Thr Ser Pro Cys Ser Ser Gly Ser Ser Trp Ser Ala Asp Leu Asp Lys
        35                  40                  45

Cys Met Asp Cys Ala Ser Cys Pro Ala Arg Pro His Ser Asp Phe Cys
50                  55                  60

Leu Gly Cys Ala Ala Ala Pro Pro Ala His Phe Arg Leu Leu Trp Pro
65                  70                  75                  80

Ile Leu Gly Gly Ala Leu Ser Leu Val Leu Val Leu Ala Leu Val Ser
                85                  90                  95

Ser Phe Leu Val Trp Arg Arg Cys Arg Arg Arg Glu Lys Phe Thr Thr
                100                 105                 110

Pro Ile Glu Glu Thr Gly Gly Glu Gly Cys Pro Gly Val Ala Leu Ile
            115                 120                 125

Gln
```

<210> SEQ ID NO 6
<211> LENGTH: 932
<212> TYPE: DNA
<213> ORGANISM: Artificial Sequence
<220> FEATURE:
<223> OTHER INFORMATION: TWEAKR:Fc
<220> FEATURE:
<221> NAME/KEY: CDS
<222> LOCATION: (1)..(930)

<400> SEQUENCE: 6

```
atg gct cgg ggc tcg ctg cgc cgg ttg ctg cgg ctc ctc gtg ctg ggg    48
Met Ala Arg Gly Ser Leu Arg Arg Leu Leu Arg Leu Leu Val Leu Gly
1               5                   10                  15 ctc tgg ctg gcg ttg ctc cgc tcc gtg gcc ggg gag caa gcg cca ggc    96
Leu Trp Leu Ala Leu Leu Arg Ser Val Ala Gly Glu Gln Ala Pro Gly
```

```
                     20                  25                  30
acc gcc ccc tgc tcc cgc ggc agc tcc tgg agc gcg gac ctg gac aag     144
Thr Ala Pro Cys Ser Arg Gly Ser Ser Trp Ser Ala Asp Leu Asp Lys
         35                  40                  45 tgc atg gac tgc gcg tct tgc agg gcg cga ccg cac agc gac ttc tgc     192
Cys Met Asp Cys Ala Ser Cys Arg Ala Arg Pro His Ser Asp Phe Cys
 50                  55                  60 ctg ggc tgc gct gca gca cct cct gcc ccc ttc cgg ctg ctt tgg aga     240
Leu Gly Cys Ala Ala Ala Pro Pro Ala Pro Phe Arg Leu Leu Trp Arg
 65                  70                  75                  80 tct tgt gac aaa act cac aca tgc cca ccg tgc cca gca cct gaa gcc     288
Ser Cys Asp Lys Thr His Thr Cys Pro Pro Cys Pro Ala Pro Glu Ala
             85                  90                  95 gag ggc gcg ccg tca gtc ttc ctc ttc ccc cca aaa ccc aag gac acc     336
Glu Gly Ala Pro Ser Val Phe Leu Phe Pro Pro Lys Pro Lys Asp Thr
                100                 105                 110 ctc atg atc tcc cgg acc cct gag gtc aca tgc gtg gtg gtg gac gtg     384
Leu Met Ile Ser Arg Thr Pro Glu Val Thr Cys Val Val Val Asp Val
            115                 120                 125 agc cac gaa gac cct gag gtc aag ttc aac tgg tac gtg gac ggc gtg     432
Ser His Glu Asp Pro Glu Val Lys Phe Asn Trp Tyr Val Asp Gly Val
130                 135                 140 gag gtg cat aat gcc aag aca aag ccg cgg gag gag cag tac aac agc     480
Glu Val His Asn Ala Lys Thr Lys Pro Arg Glu Glu Gln Tyr Asn Ser
145                 150                 155                 160 acg tac cgt gtg gtc agc gtc ctc acc gtc ctg cac cag gac tgg ctg     528
Thr Tyr Arg Val Val Ser Val Leu Thr Val Leu His Gln Asp Trp Leu
                165                 170                 175 aat ggc aag gag tac aag tgc aag gtc tcc aac aaa gcc ctc cca gcc     576
Asn Gly Lys Glu Tyr Lys Cys Lys Val Ser Asn Lys Ala Leu Pro Ala
            180                 185                 190 ccc atc gag aaa acc atc tcc aaa gcc aaa ggg cag ccc cga gaa cca     624
Pro Ile Glu Lys Thr Ile Ser Lys Ala Lys Gly Gln Pro Arg Glu Pro
        195                 200                 205 cag gtg tac acc ctg ccc cca tcc cgg gag gag atg acc aag aac cag     672
Gln Val Tyr Thr Leu Pro Pro Ser Arg Glu Glu Met Thr Lys Asn Gln
    210                 215                 220 gtc agc ctg acc tgc ctg gtc aaa ggc ttc tat ccc agc gac atc gcc     720
Val Ser Leu Thr Cys Leu Val Lys Gly Phe Tyr Pro Ser Asp Ile Ala
225                 230                 235                 240 gtg gag tgg gag agc aat ggg cag ccg gag aac aac tac aag acc acg     768
Val Glu Trp Glu Ser Asn Gly Gln Pro Glu Asn Asn Tyr Lys Thr Thr
                245                 250                 255 cct ccc gtg ctg gac tcc gac ggc tcc ttc ttc ctc tat agc aag ctc     816
Pro Pro Val Leu Asp Ser Asp Gly Ser Phe Phe Leu Tyr Ser Lys Leu
            260                 265                 270 acc gtg gac aag agc agg tgg cag cag ggg aac gtc ttc tca tgc tcc     864
Thr Val Asp Lys Ser Arg Trp Gln Gln Gly Asn Val Phe Ser Cys Ser
        275                 280                 285 gtg atg cat gag gct ctg cac aac cac tac acg cag aag agc ctc tcc     912
Val Met His Glu Ala Leu His Asn His Tyr Thr Gln Lys Ser Leu Ser
    290                 295                 300 ctg tct ccg ggt aaa tga ac                                          932
Leu Ser Pro Gly Lys
305

<210> SEQ ID NO 7
<211> LENGTH: 309
<212> TYPE: PRT
<213> ORGANISM: Artificial Sequence
```

<220> FEATURE:
<223> OTHER INFORMATION: Synthetic Construct

<400> SEQUENCE: 7

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Arg
65                  70                  75                  80

Ser Cys Asp Lys Thr His Thr Cys Pro Pro Cys Pro Ala Pro Glu Ala
                85                  90                  95

Glu Gly Ala Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Glu Glu Met Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305
```

<210> SEQ ID NO 8
<211> LENGTH: 1089
<212> TYPE: DNA
<213> ORGANISM: Artificial Sequence
<220> FEATURE:
<223> OTHER INFORMATION: TWEAKRDr5-Fc
<220> FEATURE:
<221> NAME/KEY: CDS
<222> LOCATION: (1)..(1086)

<400> SEQUENCE: 8 atg gct cgg ggc tcg ctg cgc cgg ttg ctg cgg ctc ctc gtg ctg ggg    48

```
        Met Ala Arg Gly Ser Leu Arg Arg Leu Leu Arg Leu Leu Val Leu Gly
        1               5                   10                  15 ctc tgg ctg gcg ttg ctg cgc tcc gtg gcc ggg gag caa gcg cca ggc              96
Leu Trp Leu Ala Leu Leu Arg Ser Val Ala Gly Glu Gln Ala Pro Gly
                20                  25                  30 acc gcc ccc tgc tcc cgc ggc agc tcc tgg agc gcg gac ctg gac aag             144
Thr Ala Pro Cys Ser Arg Gly Ser Ser Trp Ser Ala Asp Leu Asp Lys
            35                  40                  45 tgc atg gac tgc gcg tct tgc agg gcg cga ccg cac agc gac ttc tgc             192
Cys Met Asp Cys Ala Ser Cys Arg Ala Arg Pro His Ser Asp Phe Cys
        50                  55                  60 ctg ggc tgc gct gca gca cct cct gcc ccc ttc cgg ctg ctt tgg gag             240
Leu Gly Cys Ala Ala Ala Pro Pro Ala Pro Phe Arg Leu Leu Trp Glu
65                  70                  75                  80 caa gcg cca ggc acc gcc ccc tgc tcc cgc ggc agc act cac tgg aat             288
Gln Ala Pro Gly Thr Ala Pro Cys Ser Arg Gly Ser Thr His Trp Asn
                85                  90                  95 gac ctc ctt ttc tgc ttg cgc tgc acc agg tgt gat tca ggt gaa gtg             336
Asp Leu Leu Phe Cys Leu Arg Cys Thr Arg Cys Asp Ser Gly Glu Val
                100                 105                 110 gag cta agt ccc tgc acc acg acc gct gca gca cct cct gcc ccc ttc             384
Glu Leu Ser Pro Cys Thr Thr Thr Ala Ala Ala Pro Pro Ala Pro Phe
        115                 120                 125 cgg ctg ctt tgg aga tct tgt gac aaa act cac aca tgc cca ccg tgc             432
Arg Leu Leu Trp Arg Ser Cys Asp Lys Thr His Thr Cys Pro Pro Cys
    130                 135                 140 cca gca cct gaa gcc gag ggc gcg ccg tca gtc ttc ctc ttc ccc cca             480
Pro Ala Pro Glu Ala Glu Gly Ala Pro Ser Val Phe Leu Phe Pro Pro
145                 150                 155                 160 aaa ccc aag gac acc ctc atg atc tcc cgg acc cct gag gtc aca tgc             528
Lys Pro Lys Asp Thr Leu Met Ile Ser Arg Thr Pro Glu Val Thr Cys
                165                 170                 175 gtg gtg gtg gac gtg agc cac gaa gac cct gag gtc aag ttc aac tgg             576
Val Val Val Asp Val Ser His Glu Asp Pro Glu Val Lys Phe Asn Trp
                180                 185                 190 tac gtg gac ggc gtg gag gtg cat aat gcc aag aca aag ccg cgg gag             624
Tyr Val Asp Gly Val Glu Val His Asn Ala Lys Thr Lys Pro Arg Glu
            195                 200                 205 gag cag tac aac agc acg tac cgt gtg gtc agc gtc ctc acc gtc ctg             672
Glu Gln Tyr Asn Ser Thr Tyr Arg Val Val Ser Val Leu Thr Val Leu
        210                 215                 220 cac cag gac tgg ctg aat ggc aag gag tac aag tgc aag gtc tcc aac             720
His Gln Asp Trp Leu Asn Gly Lys Glu Tyr Lys Cys Lys Val Ser Asn
225                 230                 235                 240 aaa gcc ctc cca gcc ccc atc gag aaa acc atc tcc aaa gcc aaa ggg             768
Lys Ala Leu Pro Ala Pro Ile Glu Lys Thr Ile Ser Lys Ala Lys Gly
                245                 250                 255 cag ccc cga gaa cca cag gtg tac acc ctg ccc cca tcc cgg gag gag             816
Gln Pro Arg Glu Pro Gln Val Tyr Thr Leu Pro Pro Ser Arg Glu Glu
                260                 265                 270 atg acc aag aac cag gtc agc ctg acc tgc ctg gtc aaa ggc ttc tat             864
Met Thr Lys Asn Gln Val Ser Leu Thr Cys Leu Val Lys Gly Phe Tyr
            275                 280                 285 ccc agc gac atc gcc gtg gag tgg gag agc aat ggg cag ccg gag aac             912
Pro Ser Asp Ile Ala Val Glu Trp Glu Ser Asn Gly Gln Pro Glu Asn
        290                 295                 300 aac tac aag acc acg cct ccc gtg ctg gac tcc gac ggc tcc ttc ttc             960
Asn Tyr Lys Thr Thr Pro Pro Val Leu Asp Ser Asp Gly Ser Phe Phe
305                 310                 315                 320
```

```
ctc tat agc aag ctc acc gtg gac aag agc agg tgg cag cag ggg aac      1008
Leu Tyr Ser Lys Leu Thr Val Asp Lys Ser Arg Trp Gln Gln Gly Asn
            325                 330                 335 gtc ttc tca tgc tcc gtg atg cat gag gct ctg cac aac cac tac acg      1056
Val Phe Ser Cys Ser Val Met His Glu Ala Leu His Asn His Tyr Thr
340                 345                 350 cag aag agc ctc tcc ctg tct ccg ggt aaa tga                          1089
Gln Lys Ser Leu Ser Leu Ser Pro Gly Lys
            355                 360

<210> SEQ ID NO 9
<211> LENGTH: 362
<212> TYPE: PRT
<213> ORGANISM: Artificial Sequence
<220> FEATURE:
<223> OTHER INFORMATION: Synthetic Construct

<400> SEQUENCE: 9
```

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Glu
65                  70                  75                  80

Gln Ala Pro Gly Thr Ala Pro Cys Ser Arg Gly Ser Thr His Trp Asn
                85                  90                  95

Asp Leu Leu Phe Cys Leu Arg Cys Thr Arg Cys Asp Ser Gly Glu Val
            100                 105                 110

Glu Leu Ser Pro Cys Thr Thr Thr Ala Ala Ala Pro Ala Pro Ala Phe
        115                 120                 125

Arg Leu Leu Trp Arg Ser Cys Asp Lys Thr His Thr Cys Pro Pro Cys
130                 135                 140

Pro Ala Pro Glu Ala Glu Gly Ala Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Glu Glu
            260                 265                 270

Met Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

```
Asn Tyr Lys Thr Thr Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
            325                 330                 335

Val Phe Ser Cys Ser Val Met His Glu Ala Leu His Asn His Tyr Thr
            340                 345                 350

Gln Lys Ser Leu Ser Leu Ser Pro Gly Lys
        355                 360

<210> SEQ ID NO 10
<211> LENGTH: 1086
<212> TYPE: DNA
<213> ORGANISM: Artificial Sequence
<220> FEATURE:
<223> OTHER INFORMATION: Di TWEAKR-Fc
<220> FEATURE:
<221> NAME/KEY: CDS
<222> LOCATION: (1)..(1083)

<400> SEQUENCE: 10 atg gct cgg ggc tcg ctg cgc cgg ttg ctg cgg ctc ctc gtg ctg ggg       48
Met Ala Arg Gly Ser Leu Arg Arg Leu Leu Arg Leu Leu Val Leu Gly
1               5                   10                  15 ctc tgg ctg gcg ttg ctg cgc tcc gtg gcc ggg gag caa gcg cca ggc       96
Leu Trp Leu Ala Leu Leu Arg Ser Val Ala Gly Glu Gln Ala Pro Gly
            20                  25                  30 acc gcc ccc tgc tcc cgc ggc agc tcc tgg agc gcg gac ctg gac aag      144
Thr Ala Pro Cys Ser Arg Gly Ser Ser Trp Ser Ala Asp Leu Asp Lys
        35                  40                  45 tgc atg gac tgc gcg tct tgc agg gcg cga ccg cac agc gac ttc tgc      192
Cys Met Asp Cys Ala Ser Cys Arg Ala Arg Pro His Ser Asp Phe Cys
    50                  55                  60 ctg ggc tgc gct gca gca cct cct gcc ccc ttc cgg ctg ctt tgg gag      240
Leu Gly Cys Ala Ala Ala Pro Pro Ala Pro Phe Arg Leu Leu Trp Glu
65                  70                  75                  80 caa gcg cca ggc acc gcc ccc tgc tcc cgc ggc agc tcc tgg agc gcg      288
Gln Ala Pro Gly Thr Ala Pro Cys Ser Arg Gly Ser Ser Trp Ser Ala
                85                  90                  95 gac ctg gac aag tgc atg gac tgc gcg tct tgc agg gcg cga ccg cac      336
Asp Leu Asp Lys Cys Met Asp Cys Ala Ser Cys Arg Ala Arg Pro His
            100                 105                 110 agc gac ttc tgc ctg ggc tgc gct gca gca cct cct gcc ccc ttc cgg      384
Ser Asp Phe Cys Leu Gly Cys Ala Ala Ala Pro Pro Ala Pro Phe Arg
        115                 120                 125 ctg ctt tgg aga tct tgt gac aaa act cac aca tgc cca ccg tgc cca      432
Leu Leu Trp Arg Ser Cys Asp Lys Thr His Thr Cys Pro Pro Cys Pro
    130                 135                 140 gca cct gaa gcc gag ggc gcg ccg tca gtc ttc ctc ttc ccc cca aaa      480
Ala Pro Glu Ala Glu Gly Ala Pro Ser Val Phe Leu Phe Pro Pro Lys
145                 150                 155                 160 ccc aag gac acc ctc atg atc tcc cgg acc cct gag gtc aca tgc gtg      528
Pro Lys Asp Thr Leu Met Ile Ser Arg Thr Pro Glu Val Thr Cys Val
                165                 170                 175 gtg gtg gac gtg agc cac gaa gac cct gag gtc aag ttc aac tgg tac      576
Val Val Asp Val Ser His Glu Asp Pro Glu Val Lys Phe Asn Trp Tyr
            180                 185                 190 gtg gac ggc gtg gag gtg cat aat gcc aag aca aag ccg cgg gag gag      624
Val Asp Gly Val Glu Val His Asn Ala Lys Thr Lys Pro Arg Glu Glu
        195                 200                 205 cag tac aac agc acg tac cgt gtg gtc agc gtc ctc acc gtc ctg cac      672
Gln Tyr Asn Ser Thr Tyr Arg Val Val Ser Val Leu Thr Val Leu His
```

-continued

```
         210                 215                 220
cag gac tgg ctg aat ggc aag gag tac aag tgc aag gtc tcc aac aaa    720
Gln Asp Trp Leu Asn Gly Lys Glu Tyr Lys Cys Lys Val Ser Asn Lys
225                 230                 235                 240 gcc ctc cca gcc ccc atc gag aaa acc atc tcc aaa gcc aaa ggg cag    768
Ala Leu Pro Ala Pro Ile Glu Lys Thr Ile Ser Lys Ala Lys Gly Gln
                245                 250                 255 ccc cga gaa cca cag gtg tac acc ctg ccc cca tcc cgg gag gag atg    816
Pro Arg Glu Pro Gln Val Tyr Thr Leu Pro Pro Ser Arg Glu Glu Met
            260                 265                 270 acc aag aac cag gtc agc ctg acc tgc ctg gtc aaa ggc ttc tat ccc    864
Thr Lys Asn Gln Val Ser Leu Thr Cys Leu Val Lys Gly Phe Tyr Pro
        275                 280                 285 agc gac atc gcc gtg gag tgg gag agc aat ggg cag ccg gag aac aac    912
Ser Asp Ile Ala Val Glu Trp Glu Ser Asn Gly Gln Pro Glu Asn Asn
    290                 295                 300 tac aag acc acg cct ccc gtg ctg gac tcc gac ggc tcc ttc ttc ctc    960
Tyr Lys Thr Thr Pro Pro Val Leu Asp Ser Asp Gly Ser Phe Phe Leu
305                 310                 315                 320 tat agc aag ctc acc gtg gac aag agc agg tgg cag cag ggg aac gtc   1008
Tyr Ser Lys Leu Thr Val Asp Lys Ser Arg Trp Gln Gln Gly Asn Val
                325                 330                 335 ttc tca tgc tcc gtg atg cat gag gct ctg cac aac cac tac acg cag   1056
Phe Ser Cys Ser Val Met His Glu Ala Leu His Asn His Tyr Thr Gln
            340                 345                 350 aag agc ctc tcc ctg tct ccg ggt aaa tga                           1086
Lys Ser Leu Ser Leu Ser Pro Gly Lys
        355                 360

<210> SEQ ID NO 11
<211> LENGTH: 361
<212> TYPE: PRT
<213> ORGANISM: Artificial Sequence
<220> FEATURE:
<223> OTHER INFORMATION: Synthetic Construct

<400> SEQUENCE: 11

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
        50                  55                  60

Leu Gly Cys Ala Ala Ala Pro Pro Ala Pro Phe Arg Leu Leu Trp Glu
65                  70                  75                  80

Gln Ala Pro Gly Thr Ala Pro Cys Ser Arg Gly Ser Ser Trp Ser Ala
                85                  90                  95

Asp Leu Asp Lys Cys Met Asp Cys Ala Ser Cys Arg Ala Arg Pro His
            100                 105                 110

Ser Asp Phe Cys Leu Gly Cys Ala Ala Ala Pro Pro Ala Pro Phe Arg
        115                 120                 125

Leu Leu Trp Arg Ser Cys Asp Lys Thr His Thr Cys Pro Pro Cys Pro
    130                 135                 140

Ala Pro Glu Ala Glu Gly Ala Pro Ser Val Phe Leu Phe Pro Pro Lys
145                 150                 155                 160

Pro Lys Asp Thr Leu Met Ile Ser Arg Thr Pro Glu Val Thr Cys Val
```

```
                        165                 170                 175
Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
            210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
            245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
            290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 12
<211> LENGTH: 1242
<212> TYPE: DNA
<213> ORGANISM: Artificial Sequence
<220> FEATURE:
<223> OTHER INFORMATION: Tri TWEAKR-Fc
<220> FEATURE:
<221> NAME/KEY: CDS
<222> LOCATION: (1)..(1239)

<400> SEQUENCE: 12 atg gct cgg ggc tcg ctg cgc cgg ttg ctg cgg ctc ctc gtg ctg ggg      48
Met Ala Arg Gly Ser Leu Arg Arg Leu Leu Arg Leu Leu Val Leu Gly
1               5                   10                  15 ctc tgg ctg gcg ttg ctg cgc tcc gtg gcc ggg gag caa gcg cca ggc      96
Leu Trp Leu Ala Leu Leu Arg Ser Val Ala Gly Glu Gln Ala Pro Gly
            20                  25                  30 acc gcc ccc tgc tcc cgc ggc agc tcc tgg agc gcg gac ctg gac aag     144
Thr Ala Pro Cys Ser Arg Gly Ser Ser Trp Ser Ala Asp Leu Asp Lys
        35                  40                  45 tgc atg gac tgc gcg tct tgc agg gcg cga ccg cac agc gac ttc tgc     192
Cys Met Asp Cys Ala Ser Cys Arg Ala Arg Pro His Ser Asp Phe Cys
    50                  55                  60 ctg ggc tgc gct gca cct cct gcc ccc ttc cgg ctg ctt tgg gag         240
Leu Gly Cys Ala Ala Ala Pro Pro Ala Pro Phe Arg Leu Leu Trp Glu
65                  70                  75                  80 caa gcg cca ggc acc gcc ccc tgc tcc cgc ggc agc tcc tgg agc gcg     288
Gln Ala Pro Gly Thr Ala Pro Cys Ser Arg Gly Ser Ser Trp Ser Ala
            85                  90                  95 gac ctg gac aag tgc atg gac tgc gcg tct tgc agg gcg cga ccg cac     336
Asp Leu Asp Lys Cys Met Asp Cys Ala Ser Cys Arg Ala Arg Pro His
            100                 105                 110
```

```
agc gac ttc tgc ctg ggc tgc gct gca gca cct cct gcc ccc ttc cgg        384
Ser Asp Phe Cys Leu Gly Cys Ala Ala Ala Pro Pro Ala Pro Phe Arg
        115                 120                 125 ctg ctt tgg gag caa gcg cca ggc acc gcc ccc tgc tcc cgc ggc agc        432
Leu Leu Trp Glu Gln Ala Pro Gly Thr Ala Pro Cys Ser Arg Gly Ser
    130                 135                 140 tcc tgg agc gcg gac ctg gac aag tgc atg gac tgc gcg tct tgc agg        480
Ser Trp Ser Ala Asp Leu Asp Lys Cys Met Asp Cys Ala Ser Cys Arg
145                 150                 155                 160 gcg cga ccg cac agc gac ttc tgc ctg ggc tgc gct gca gca cct cct        528
Ala Arg Pro His Ser Asp Phe Cys Leu Gly Cys Ala Ala Ala Pro Pro
                165                 170                 175 gcc ccc ttc cgg ctg ctt tgg aga tct tgt gac aaa act cac aca tgc        576
Ala Pro Phe Arg Leu Leu Trp Arg Ser Cys Asp Lys Thr His Thr Cys
            180                 185                 190 cca ccg tgc cca gca cct gaa gcc gag ggc gcg cca tca gtc ttc ctc        624
Pro Pro Cys Pro Ala Pro Glu Ala Glu Gly Ala Pro Ser Val Phe Leu
        195                 200                 205 ttc ccc cca aaa ccc aag gac acc ctc atg atc tcc cgg acc cct gag        672
Phe Pro Pro Lys Pro Lys Asp Thr Leu Met Ile Ser Arg Thr Pro Glu
    210                 215                 220 gtc aca tgc gtg gtg gtg gac gtg agc cac gaa gac cct gag gtc aag        720
Val Thr Cys Val Val Val Asp Val Ser His Glu Asp Pro Glu Val Lys
225                 230                 235                 240 ttc aac tgg tac gtg gac ggc gtg gag gtg cat aat gcc aag aca aag        768
Phe Asn Trp Tyr Val Asp Gly Val Glu Val His Asn Ala Lys Thr Lys
                245                 250                 255 ccg cgg gag gag cag tac aac agc acg tac cgt gtg gtc agc gtc ctc        816
Pro Arg Glu Glu Gln Tyr Asn Ser Thr Tyr Arg Val Val Ser Val Leu
            260                 265                 270 acc gtc ctg cac cag gac tgg ctg aat ggc aag gag tac aag tgc aag        864
Thr Val Leu His Gln Asp Trp Leu Asn Gly Lys Glu Tyr Lys Cys Lys
        275                 280                 285 gtc tcc aac aaa gcc ctc cca gcc ccc atc gag aaa acc atc tcc aaa        912
Val Ser Asn Lys Ala Leu Pro Ala Pro Ile Glu Lys Thr Ile Ser Lys
    290                 295                 300 gcc aaa ggg cag ccc cga gaa cca cag gtg tac acc ctg ccc cca tcc        960
Ala Lys Gly Gln Pro Arg Glu Pro Gln Val Tyr Thr Leu Pro Pro Ser
305                 310                 315                 320 cgg gag gag atg acc aag aac cag gtc agc ctg acc tgc ctg gtc aaa       1008
Arg Glu Glu Met Thr Lys Asn Gln Val Ser Leu Thr Cys Leu Val Lys
                325                 330                 335 ggc ttc tat ccc agc gac atc gcc gtg gag tgg gag agc aat ggg cag       1056
Gly Phe Tyr Pro Ser Asp Ile Ala Val Glu Trp Glu Ser Asn Gly Gln
            340                 345                 350 ccg gag aac aac tac aag acc acg cct ccc gtg ctg gac tcc gac ggc       1104
Pro Glu Asn Asn Tyr Lys Thr Thr Pro Pro Val Leu Asp Ser Asp Gly
        355                 360                 365 tcc ttc ttc ctc tat agc aag ctc acc gtg gac aag agc agg tgg cag       1152
Ser Phe Phe Leu Tyr Ser Lys Leu Thr Val Asp Lys Ser Arg Trp Gln
    370                 375                 380 cag ggg aac gtc ttc tca tgc tcc gtg atg cat gag gct ctg cac aac       1200
Gln Gly Asn Val Phe Ser Cys Ser Val Met His Glu Ala Leu His Asn
385                 390                 395                 400 cac tac acg cag aag agc ctc tcc ctg tct ccg ggt aaa tga               1242
His Tyr Thr Gln Lys Ser Leu Ser Leu Ser Pro Gly Lys
                405                 410

<210> SEQ ID NO 13
<211> LENGTH: 413
```

<212> TYPE: PRT
<213> ORGANISM: Artificial Sequence
<220> FEATURE:
<223> OTHER INFORMATION: Synthetic Construct

<400> SEQUENCE: 13

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Cys
50                  55                  60

Leu Gly Cys Ala Ala Ala Pro Pro Ala Pro Phe Arg Leu Leu Trp Glu
65                  70                  75                  80

Gln Ala Pro Gly Thr Ala Pro Cys Ser Arg Gly Ser Ser Trp Ser Ala
                85                  90                  95

Asp Leu Asp Lys Cys Met Asp Cys Ala Ser Cys Arg Ala Arg Pro His
            100                 105                 110

Ser Asp Phe Cys Leu Gly Cys Ala Ala Ala Pro Pro Ala Pro Phe Arg
        115                 120                 125

Leu Leu Trp Glu Gln Ala Pro Gly Thr Ala Pro Cys Ser Arg Gly Ser
    130                 135                 140

Ser Trp Ser Ala Asp Leu Asp Lys Cys Met Asp Cys Ala Ser Cys Arg
145                 150                 155                 160

Ala Arg Pro His Ser Asp Phe Cys Leu Gly Cys Ala Ala Ala Pro Pro
                165                 170                 175

Ala Pro Phe Arg Leu Leu Trp Arg Ser Cys Asp Lys Thr His Thr Cys
            180                 185                 190

Pro Pro Cys Pro Ala Pro Glu Ala Glu Gly Ala Pro Ser Val Phe Leu
        195                 200                 205

Phe Pro Pro Lys Pro Lys Asp Thr Leu Met Ile Ser Arg Thr Pro Glu
    210                 215                 220

Val Thr Cys Val Val Asp Val Ser His Glu Asp Pro Glu Val Lys
225                 230                 235                 240

Phe Asn Trp Tyr Val Asp Gly Val Glu Val His Asn Ala Lys Thr Lys
                245                 250                 255

Pro Arg Glu Glu Gln Tyr Asn Ser Thr Tyr Arg Val Val Ser Val Leu
            260                 265                 270

Thr Val Leu His Gln Asp Trp Leu Asn Gly Lys Glu Tyr Lys Cys Lys
        275                 280                 285

Val Ser Asn Lys Ala Leu Pro Ala Pro Ile Glu Lys Thr Ile Ser Lys
    290                 295                 300

Ala Lys Gly Gln Pro Arg Glu Pro Gln Val Tyr Thr Leu Pro Pro Ser
305                 310                 315                 320

Arg Glu Glu Met Thr Lys Asn Gln Val Ser Leu Thr Cys Leu Val Lys
                325                 330                 335

Gly Phe Tyr Pro Ser Asp Ile Ala Val Glu Trp Glu Ser Asn Gly Gln
            340                 345                 350

Pro Glu Asn Asn Tyr Lys Thr Thr Pro Pro Val Leu Asp Ser Asp Gly
        355                 360                 365

Ser Phe Phe Leu Tyr Ser Lys Leu Thr Val Asp Lys Ser Arg Trp Gln
    370                 375                 380
```

```
          Gln Gly Asn Val Phe Ser Cys Ser Val Met His Glu Ala Leu His Asn
          385                 390                 395                 400

His Tyr Thr Gln Lys Ser Leu Ser Leu Ser Pro Gly Lys
                          405                 410

<210> SEQ ID NO 14
<211> LENGTH: 828
<212> TYPE: DNA
<213> ORGANISM: Artificial
<220> FEATURE:
<223> OTHER INFORMATION: HuTWEAKr 29-70:Gly5:Fc
<220> FEATURE:
<221> NAME/KEY: CDS
<222> LOCATION: (1)..(825)

<400> SEQUENCE: 14 atg caa gct cca ggt act gca cca tgt tct cgt ggt tct tct tgg tct      48
Met Gln Ala Pro Gly Thr Ala Pro Cys Ser Arg Gly Ser Ser Trp Ser
1               5                   10                  15 gct gat ctt gat aaa tgt atg gat tgt gct tct tgt cgt gct cgt cca      96
Ala Asp Leu Asp Lys Cys Met Asp Cys Ala Ser Cys Arg Ala Arg Pro
            20                  25                  30 cat tct gat ttt tgt ctg ggt tgt gct gct gct ggt ggt ggt ggt ggt     144
His Ser Asp Phe Cys Leu Gly Cys Ala Ala Ala Gly Gly Gly Gly Gly
        35                  40                  45 gac aaa act cac aca tgt cca ccg tgc cca gca cct gaa ctc ctg ggg     192
Asp Lys Thr His Thr Cys Pro Pro Cys Pro Ala Pro Glu Leu Leu Gly
50                  55                  60 gga ccg tca gtt ttc ctc ttc ccc cca aaa ccc aag gac acc ctc atg     240
Gly Pro Ser Val Phe Leu Phe Pro Pro Lys Pro Lys Asp Thr Leu Met
65                  70                  75                  80 atc tcc cgg acc cct gag gtc aca tgc gtg gtg gtg gac gtg agc cac     288
Ile Ser Arg Thr Pro Glu Val Thr Cys Val Val Val Asp Val Ser His
                85                  90                  95 gaa gac cct gag gtc aag ttc aac tgg tac gtg gac ggc gtg gag gtg     336
Glu Asp Pro Glu Val Lys Phe Asn Trp Tyr Val Asp Gly Val Glu Val
            100                 105                 110 cat aat gcc aag aca aag ccg cgg gag gag cag tac aac agc acg tac     384
His Asn Ala Lys Thr Lys Pro Arg Glu Glu Gln Tyr Asn Ser Thr Tyr
        115                 120                 125 cgt gtg gtc agc gtc ctc acc gtc ctg cac cag gac tgg ctg aat ggc     432
Arg Val Val Ser Val Leu Thr Val Leu His Gln Asp Trp Leu Asn Gly
    130                 135                 140 aag gag tac aag tgc aag gtc tcc aac aaa gcc ctc cca gcc ccc atc     480
Lys Glu Tyr Lys Cys Lys Val Ser Asn Lys Ala Leu Pro Ala Pro Ile
145                 150                 155                 160 gag aaa acc atc tcc aaa gcc aaa ggg cag ccc cga gaa cca cag gtg     528
Glu Lys Thr Ile Ser Lys Ala Lys Gly Gln Pro Arg Glu Pro Gln Val
                165                 170                 175 tac acc ctg ccc cca tcc cgg gat gag ctg acc aag aac cag gtc agc     576
Tyr Thr Leu Pro Pro Ser Arg Asp Glu Leu Thr Lys Asn Gln Val Ser
            180                 185                 190 ctg acc tgc ctg gtc aaa ggc ttc tat ccc agc gac atc gcc gtg gag     624
Leu Thr Cys Leu Val Lys Gly Phe Tyr Pro Ser Asp Ile Ala Val Glu
        195                 200                 205 tgg gag agc aat ggg cag ccg gag aac aac tac aag acc acg cct ccc     672
Trp Glu Ser Asn Gly Gln Pro Glu Asn Asn Tyr Lys Thr Thr Pro Pro
    210                 215                 220 gtg ctg gac tcc gac ggc tcc ttc ttc ctc tac agc aag ctc acc gtg     720
Val Leu Asp Ser Asp Gly Ser Phe Phe Leu Tyr Ser Lys Leu Thr Val
225                 230                 235                 240
```

```
gac aag agc agg tgg cag cag ggg aac gtc ttc tca tgc tcc gtg atg    768
Asp Lys Ser Arg Trp Gln Gln Gly Asn Val Phe Ser Cys Ser Val Met
        245                 250                 255 cat gag gct ctg cac aac cac tac acg cag aag agc ctc tcc ctg tct    816
His Glu Ala Leu His Asn His Tyr Thr Gln Lys Ser Leu Ser Leu Ser
    260                 265                 270 ccg ggt aaa taa                                                    828
Pro Gly Lys
        275
```

<210> SEQ ID NO 15
<211> LENGTH: 275
<212> TYPE: PRT
<213> ORGANISM: Artificial
<220> FEATURE:
<223> OTHER INFORMATION: Synthetic Construct

<400> SEQUENCE: 15

```
Met Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Gly Gly Gly Gly
        35                  40                  45

Asp Lys Thr His Thr Cys Pro Pro Cys Pro Ala Pro Glu Leu Leu Gly
    50                  55                  60

Gly Pro Ser Val Phe Leu Phe Pro Pro Lys Pro Lys Asp Thr Leu Met
65                  70                  75                  80

Ile Ser Arg Thr Pro Glu Val Thr Cys Val Val Val Asp Val Ser His
                85                  90                  95

Glu Asp Pro Glu Val Lys Phe Asn Trp Tyr Val Asp Gly Val Glu Val
            100                 105                 110

His Asn Ala Lys Thr Lys Pro Arg Glu Glu Gln Tyr Asn Ser Thr Tyr
        115                 120                 125

Arg Val Val Ser Val Leu Thr Val Leu His Gln Asp Trp Leu Asn Gly
    130                 135                 140

Lys Glu Tyr Lys Cys Lys Val Ser Asn Lys Ala Leu Pro Ala Pro Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Arg Asp Glu Leu Thr Lys Asn Gln Val Ser
            180                 185                 190

Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Lys Leu Thr Val
225                 230                 235                 240

Asp Lys Ser Arg Trp Gln Gln Gly Asn Val Phe Ser Cys Ser Val Met
                245                 250                 255

His Glu Ala Leu His Asn His Tyr Thr Gln Lys Ser Leu Ser Leu Ser
            260                 265                 270

Pro Gly Lys
        275
```

<210> SEQ ID NO 16
<211> LENGTH: 879

```
<212> TYPE: DNA
<213> ORGANISM: Artificial
<220> FEATURE:
<223> OTHER INFORMATION: HuTWEAKr 29-70:1KPEG:Fc
<220> FEATURE:
<221> NAME/KEY: CDS
<222> LOCATION: (1)..(876)

<400> SEQUENCE: 16
```

| | | | | | | | | | | | | | | | | |
|---|---|---|---|---|---|---|---|---|---|---|---|---|---|---|---|---|
| atg | caa | gct | cca | ggt | act | gca | cca | tgt | tct | cgt | ggt | tct | tct | tgg | tct | 48 |
| Met | Gln | Ala | Pro | Gly | Thr | Ala | Pro | Cys | Ser | Arg | Gly | Ser | Ser | Trp | Ser | |
| 1 | | | | 5 | | | | | 10 | | | | | 15 | | |
| gct | gat | ctt | gat | aaa | tgt | atg | gat | tgt | gct | tct | tgt | cgt | gct | cgt | cca | 96 |
| Ala | Asp | Leu | Asp | Lys | Cys | Met | Asp | Cys | Ala | Ser | Cys | Arg | Ala | Arg | Pro | |
| | | | 20 | | | | | 25 | | | | | 30 | | | |
| cat | tct | gat | ttt | tgt | ctg | ggt | tgt | gct | gct | gct | ggt | tcc | gga | tct | gct | 144 |
| His | Ser | Asp | Phe | Cys | Leu | Gly | Cys | Ala | Ala | Ala | Gly | Ser | Gly | Ser | Ala | |
| | 35 | | | | | 40 | | | | | 45 | | | | | |
| acc | ggt | ggt | tcc | ggt | tct | acc | gct | tct | tct | gga | tcc | ggt | tcc | gct | acc | 192 |
| Thr | Gly | Gly | Ser | Gly | Ser | Thr | Ala | Ser | Ser | Gly | Ser | Gly | Ser | Ala | Thr | |
| 50 | | | | | 55 | | | | | 60 | | | | | | |
| ggt | gac | aaa | act | cac | aca | tgt | cca | ccg | tgc | cca | gca | cct | gaa | ctc | ctg | 240 |
| Gly | Asp | Lys | Thr | His | Thr | Cys | Pro | Pro | Cys | Pro | Ala | Pro | Glu | Leu | Leu | |
| 65 | | | | 70 | | | | | 75 | | | | | 80 | | |
| ggg | gga | ccg | tca | gtt | ttc | ctc | ttc | ccc | cca | aaa | ccc | aag | gac | acc | ctc | 288 |
| Gly | Gly | Pro | Ser | Val | Phe | Leu | Phe | Pro | Pro | Lys | Pro | Lys | Asp | Thr | Leu | |
| | | | 85 | | | | | 90 | | | | | 95 | | | |
| atg | atc | tcc | cgg | acc | cct | gag | gtc | aca | tgc | gtg | gtg | gtg | gac | gtg | agc | 336 |
| Met | Ile | Ser | Arg | Thr | Pro | Glu | Val | Thr | Cys | Val | Val | Val | Asp | Val | Ser | |
| | | 100 | | | | | 105 | | | | | 110 | | | | |
| cac | gaa | gac | cct | gag | gtc | aag | ttc | aac | tgg | tac | gtg | gac | ggc | gtg | gag | 384 |
| His | Glu | Asp | Pro | Glu | Val | Lys | Phe | Asn | Trp | Tyr | Val | Asp | Gly | Val | Glu | |
| | | 115 | | | | | 120 | | | | | 125 | | | | |
| gtg | cat | aat | gcc | aag | aca | aag | ccg | cgg | gag | gag | cag | tac | aac | agc | acg | 432 |
| Val | His | Asn | Ala | Lys | Thr | Lys | Pro | Arg | Glu | Glu | Gln | Tyr | Asn | Ser | Thr | |
| 130 | | | | | 135 | | | | | 140 | | | | | | |
| tac | cgt | gtg | gtc | agc | gtc | ctc | acc | gtc | ctg | cac | cag | gac | tgg | ctg | aat | 480 |
| Tyr | Arg | Val | Val | Ser | Val | Leu | Thr | Val | Leu | His | Gln | Asp | Trp | Leu | Asn | |
| 145 | | | | | 150 | | | | | 155 | | | | | 160 | |
| ggc | aag | gag | tac | aag | tgc | aag | gtc | tcc | aac | aaa | gcc | ctc | cca | gcc | ccc | 528 |
| Gly | Lys | Glu | Tyr | Lys | Cys | Lys | Val | Ser | Asn | Lys | Ala | Leu | Pro | Ala | Pro | |
| | | | 165 | | | | | 170 | | | | | 175 | | | |
| atc | gag | aaa | acc | atc | tcc | aaa | gcc | aaa | ggg | cag | ccc | cga | gaa | cca | cag | 576 |
| Ile | Glu | Lys | Thr | Ile | Ser | Lys | Ala | Lys | Gly | Gln | Pro | Arg | Glu | Pro | Gln | |
| | | | 180 | | | | | 185 | | | | | 190 | | | |
| gtg | tac | acc | ctg | ccc | cca | tcc | cgg | gat | gag | ctg | acc | aag | aac | cag | gtc | 624 |
| Val | Tyr | Thr | Leu | Pro | Pro | Ser | Arg | Asp | Glu | Leu | Thr | Lys | Asn | Gln | Val | |
| | | 195 | | | | | 200 | | | | | 205 | | | | |
| agc | ctg | acc | tgc | ctg | gtc | aaa | ggc | ttc | tat | ccc | agc | gac | atc | gcc | gtg | 672 |
| Ser | Leu | Thr | Cys | Leu | Val | Lys | Gly | Phe | Tyr | Pro | Ser | Asp | Ile | Ala | Val | |
| | 210 | | | | | 215 | | | | | 220 | | | | | |
| gag | tgg | gag | agc | aat | ggg | cag | ccg | gag | aac | aac | tac | aag | acc | acg | cct | 720 |
| Glu | Trp | Glu | Ser | Asn | Gly | Gln | Pro | Glu | Asn | Asn | Tyr | Lys | Thr | Thr | Pro | |
| 225 | | | | | 230 | | | | | 235 | | | | | 240 | |
| ccc | gtg | ctg | gac | tcc | gac | ggc | tcc | ttc | ttc | ctc | tac | agc | aag | ctc | acc | 768 |
| Pro | Val | Leu | Asp | Ser | Asp | Gly | Ser | Phe | Phe | Leu | Tyr | Ser | Lys | Leu | Thr | |
| | | | 245 | | | | | 250 | | | | | 255 | | | |
| gtg | gac | aag | agc | agg | tgg | cag | cag | ggg | aac | gtc | ttc | tca | tgc | tcc | gtg | 816 |
| Val | Asp | Lys | Ser | Arg | Trp | Gln | Gln | Gly | Asn | Val | Phe | Ser | Cys | Ser | Val | |
| | | 260 | | | | | 265 | | | | | 270 | | | | |
| atg | cat | gag | gct | ctg | cac | aac | cac | tac | acg | cag | aag | agc | ctc | tcc | ctg | 864 |

```
Met His Glu Ala Leu His Asn His Tyr Thr Gln Lys Ser Leu Ser Leu
            275                 280                 285 tct ccg ggt aaa taa                                                         879
Ser Pro Gly Lys
    290
```

<210> SEQ ID NO 17
<211> LENGTH: 292
<212> TYPE: PRT
<213> ORGANISM: Artificial
<220> FEATURE:
<223> OTHER INFORMATION: Synthetic Construct

<400> SEQUENCE: 17

```
Met Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Ala Gly Ser Gly Ser Ala
        35                  40                  45

Thr Gly Gly Ser Gly Ser Thr Ala Ser Ser Gly Ser Gly Ser Ala Thr
    50                  55                  60

Gly Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Asp Glu Leu Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290
```

<210> SEQ ID NO 18
<211> LENGTH: 339
<212> TYPE: PRT
<213> ORGANISM: Artificial sequence
<220> FEATURE:
<223> OTHER INFORMATION: TWEAKR:1KPEG:TWEAKR:Gly5:Fc

<400> SEQUENCE: 18

```
Met Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Gly Ser Gly Ser Ala
        35                  40                  45

Thr Gly Gly Ser Gly Ser Thr Ala Ser Ser Gly Ser Ala Thr
    50                  55                  60

His Gln Ala Pro Gly Thr Ala Pro Cys Ser Arg Gly Ser Ser Trp Ser
65                  70                  75                  80

Ala Asp Leu Asp Lys Cys Met Asp Cys Ala Ser Cys Arg Ala Arg Pro
            85                  90                  95

His Ser Asp Phe Cys Leu Gly Cys Ala Ala Gly Gly Gly Gly
        100                 105                 110

Asp Lys Thr His Thr Cys Pro Pro Cys Pro Ala Pro Glu Leu Leu Gly
        115                 120                 125

Gly Pro Ser Val Phe Leu Phe Pro Pro Lys Pro Lys Asp Thr Leu Met
130                 135                 140

Ile Ser Arg Thr Pro Glu Val Thr Cys Val Val Val Asp Val Ser His
145                 150                 155                 160

Glu Asp Pro Glu Val Lys Phe Asn Trp Tyr Val Asp Gly Val Glu Val
                165                 170                 175

His Asn Ala Lys Thr Lys Pro Arg Glu Glu Gln Tyr Asn Ser Thr Tyr
            180                 185                 190

Arg Val Val Ser Val Leu Thr Val Leu His Gln Asp Trp Leu Asn Gly
        195                 200                 205

Lys Glu Tyr Lys Cys Lys Val Ser Asn Lys Ala Leu Pro Ala Pro Ile
210                 215                 220

Glu Lys Thr Ile Ser Lys Ala Lys Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335

Pro Gly Lys
```

<210> SEQ ID NO 19
<211> LENGTH: 322
<212> TYPE: PRT
<213> ORGANISM: Artificial sequence
<220> FEATURE:
<223> OTHER INFORMATION: TWEAKR:Gly5:TWEAKR:Gly5:Fc

<400> SEQUENCE: 19

Met Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Gly Gly Gly Gly Gly
        35                  40                  45

Gln Ala Pro Gly Thr Ala Pro Cys Ser Arg Gly Ser Ser Trp Ser Ala
    50                  55                  60

Asp Leu Asp Lys Cys Met Asp Cys Ala Ser Cys Arg Ala Arg Pro His
65                  70                  75                  80

Ser Asp Phe Cys Leu Gly Cys Ala Ala Gly Gly Gly Gly Asp
            85                  90                  95

Lys Thr His Thr Cys Pro Pro Cys Pro Ala Pro Glu Leu Leu Gly Gly
            100                 105                 110

Pro Ser Val Phe Leu Phe Pro Pro Lys Pro Lys Asp Thr Leu Met Ile
            115                 120                 125

Ser Arg Thr Pro Glu Val Thr Cys Val Val Val Asp Val Ser His Glu
    130                 135                 140

Asp Pro Glu Val Lys Phe Asn Trp Tyr Val Asp Gly Val Glu Val His
145                 150                 155                 160

Asn Ala Lys Thr Lys Pro Arg Glu Glu Gln Tyr Asn Ser Thr Tyr Arg
                165                 170                 175

Val Val Ser Val Leu Thr Val Leu His Gln Asp Trp Leu Asn Gly Lys
            180                 185                 190

Glu Tyr Lys Cys Lys Val Ser Asn Lys Ala Leu Pro Ala Pro Ile Glu
        195                 200                 205

Lys Thr Ile Ser Lys Ala Lys Gly Gln Pro Arg Glu Pro Gln Val Tyr
    210                 215                 220

Thr Leu Pro Pro Ser Arg Asp Glu Leu Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Val
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys

```
<210> SEQ ID NO 20
<211> LENGTH: 867
<212> TYPE: DNA
<213> ORGANISM: Artificial sequence
<220> FEATURE:
<223> OTHER INFORMATION: TWEAKR 40mono-3
<220> FEATURE:
<221> NAME/KEY: CDS
<222> LOCATION: (1)..(867)

<400> SEQUENCE: 20
``` atg gag aca gac aca ctc ctg cta tgg gta ctg ctg ctc tgg gtt cca    48
Met Glu Thr Asp Thr Leu Leu Leu Trp Val Leu Leu Leu Trp Val Pro
1               5                   10                  15

```
ggt tcc acc ggt gca cca ggc acc gcc ccc tgc tcc cgc ggc agc tcc        96
Gly Ser Thr Gly Ala Pro Gly Thr Ala Pro Cys Ser Arg Gly Ser Ser
             20                  25                  30 tgg agc gcg gac ctg gac aag tgc atg gac tgc gcg tct tgc agg gcg       144
Trp Ser Ala Asp Leu Asp Lys Cys Met Asp Cys Ala Ser Cys Arg Ala
         35                  40                  45 cga ccg cac agc gac ttc tgc ctg ggc tgc gct gca gca gac aaa act       192
Arg Pro His Ser Asp Phe Cys Leu Gly Cys Ala Ala Ala Asp Lys Thr
     50                  55                  60 cac aca tgt cca ccg tgc cca gca cct gaa ctc ctg ggg gga ccg tca       240
His Thr Cys Pro Pro Cys Pro Ala Pro Glu Leu Leu Gly Gly Pro Ser
 65                  70                  75                  80 gtt ttc ctc ttc ccc cca aaa ccc aag gac acc ctc atg atc tcc cgg       288
Val Phe Leu Phe Pro Pro Lys Pro Lys Asp Thr Leu Met Ile Ser Arg
                 85                  90                  95 acc cct gag gtc aca tgc gtg gtg gtg gac gtg agc cac gaa gac cct       336
Thr Pro Glu Val Thr Cys Val Val Val Asp Val Ser His Glu Asp Pro
             100                 105                 110 gag gtc aag ttc aac tgg tac gtg gac ggc gtg gag gtg cat aat gcc       384
Glu Val Lys Phe Asn Trp Tyr Val Asp Gly Val Glu Val His Asn Ala
         115                 120                 125 aag aca aag ccg cgg gag gag cag tac aac agc acg tac cgt gtg gtc       432
Lys Thr Lys Pro Arg Glu Glu Gln Tyr Asn Ser Thr Tyr Arg Val Val
     130                 135                 140 agc gtc ctc acc gtc ctg cac cag gac tgg ctg aat ggc aag gag tac       480
Ser Val Leu Thr Val Leu His Gln Asp Trp Leu Asn Gly Lys Glu Tyr
145                 150                 155                 160 aag tgc aag gtc tcc aac aaa gcc ctc cca gcc ccc atc gag aaa acc       528
Lys Cys Lys Val Ser Asn Lys Ala Leu Pro Ala Pro Ile Glu Lys Thr
                 165                 170                 175 atc tcc aaa gcc aaa ggg cag ccc cga gaa cca cag gtg tac acc ctg       576
Ile Ser Lys Ala Lys Gly Gln Pro Arg Glu Pro Gln Val Tyr Thr Leu
             180                 185                 190 ccc cca tcc cgg gat gag ctg acc aag aac cag gtc agc ctg acc tgc       624
Pro Pro Ser Arg Asp Glu Leu Thr Lys Asn Gln Val Ser Leu Thr Cys
         195                 200                 205 ctg gtc aaa ggc ttc tat ccc agc gac atc gcc gtg gag tgg gag agc       672
Leu Val Lys Gly Phe Tyr Pro Ser Asp Ile Ala Val Glu Trp Glu Ser
     210                 215                 220 aat ggg cag ccg gag aac aac tac aag acc acg cct ccc gtg ctg gac       720
Asn Gly Gln Pro Glu Asn Asn Tyr Lys Thr Thr Pro Pro Val Leu Asp
225                 230                 235                 240 tcc gac ggc tcc ttc ttc ctc tac agc aag ctc acc gtg gac aag agc       768
Ser Asp Gly Ser Phe Phe Leu Tyr Ser Lys Leu Thr Val Asp Lys Ser
                 245                 250                 255 agg tgg cag cag ggg aac gtc ttc tca tgc tcc gtg atg cat gag gct       816
Arg Trp Gln Gln Gly Asn Val Phe Ser Cys Ser Val Met His Glu Ala
             260                 265                 270 ctg cac aac cac tac acg cag aag agc ctc tcc ctg tct ccg ggt aaa       864
Leu His Asn His Tyr Thr Gln Lys Ser Leu Ser Leu Ser Pro Gly Lys
         275                 280                 285 taa                                                                   867

<210> SEQ ID NO 21
<211> LENGTH: 288
<212> TYPE: PRT
<213> ORGANISM: Artificial sequence
<220> FEATURE:
<223> OTHER INFORMATION: Synthetic Construct
```

-continued

<400> SEQUENCE: 21

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Ala Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 22
<211> LENGTH: 990
<212> TYPE: DNA
<213> ORGANISM: Artificial sequence
<220> FEATURE:
<223> OTHER INFORMATION: TWEAKR 40dimer-1
<220> FEATURE:
<221> NAME/KEY: CDS
<222> LOCATION: (1)..(990)

<400> SEQUENCE: 22 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc      96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg     144
Trp Ser Ala Asp Leu Asp Lys Cys Met Asp Cys Ala Ser Cys Arg Ala

```
                 35                  40                  45
cga ccg cac agc gac ttc tgc ctg ggc tgc gct gca gca gca cca ggc       192
Arg Pro His Ser Asp Phe Cys Leu Gly Cys Ala Ala Ala Ala Pro Gly
     50                  55                  60 acc gcc ccc tgc tcc cgc ggc agc tcc tgg agc gcg gac ctg gac aag       240
Thr Ala Pro Cys Ser Arg Gly Ser Ser Trp Ser Ala Asp Leu Asp Lys
 65                  70                  75                  80 tgc atg gac tgc gcg tct tgc agg gcg cga ccg cac agc gac ttc tgc       288
Cys Met Asp Cys Ala Ser Cys Arg Ala Arg Pro His Ser Asp Phe Cys
                 85                  90                  95 ctg ggc tgc gct gca gca gac aaa act cac aca tgt cca ccg tgc cca       336
Leu Gly Cys Ala Ala Ala Asp Lys Thr His Thr Cys Pro Pro Cys Pro
            100                 105                 110 gca cct gaa ctc ctg ggg gga ccg tca gtt ttc ctc ttc ccc cca aaa       384
Ala Pro Glu Leu Leu Gly Gly Pro Ser Val Phe Leu Phe Pro Pro Lys
        115                 120                 125 ccc aag gac acc ctc atg atc tcc cgg acc cct gag gtc aca tgc gtg       432
Pro Lys Asp Thr Leu Met Ile Ser Arg Thr Pro Glu Val Thr Cys Val
    130                 135                 140 gtg gtg gac gtg agc cac gaa gac cct gag gtc aag ttc aac tgg tac       480
Val Val Asp Val Ser His Glu Asp Pro Glu Val Lys Phe Asn Trp Tyr
145                 150                 155                 160 gtg gac ggc gtg gag gtg cat aat gcc aag aca aag ccg cgg gag gag       528
Val Asp Gly Val Glu Val His Asn Ala Lys Thr Lys Pro Arg Glu Glu
                165                 170                 175 cag tac aac agc acg tac cgt gtg gtc agc gtc ctc acc gtc ctg cac       576
Gln Tyr Asn Ser Thr Tyr Arg Val Val Ser Val Leu Thr Val Leu His
            180                 185                 190 cag gac tgg ctg aat ggc aag gag tac aag tgc aag gtc tcc aac aaa       624
Gln Asp Trp Leu Asn Gly Lys Glu Tyr Lys Cys Lys Val Ser Asn Lys
        195                 200                 205 gcc ctc cca gcc ccc atc gag aaa acc atc tcc aaa gcc aaa ggg cag       672
Ala Leu Pro Ala Pro Ile Glu Lys Thr Ile Ser Lys Ala Lys Gly Gln
    210                 215                 220 ccc cga gaa cca cag gtg tac acc ctg ccc cca tcc cgg gat gag ctg       720
Pro Arg Glu Pro Gln Val Tyr Thr Leu Pro Pro Ser Arg Asp Glu Leu
225                 230                 235                 240 acc aag aac cag gtc agc ctg acc tgc ctg gtc aaa ggc ttc tat ccc       768
Thr Lys Asn Gln Val Ser Leu Thr Cys Leu Val Lys Gly Phe Tyr Pro
                245                 250                 255 agc gac atc gcc gtg gag tgg gag agc aat ggg cag ccg gag aac aac       816
Ser Asp Ile Ala Val Glu Trp Glu Ser Asn Gly Gln Pro Glu Asn Asn
            260                 265                 270 tac aag acc acg cct ccc gtg ctg gac tcc gac ggc tcc ttc ttc ctc       864
Tyr Lys Thr Thr Pro Pro Val Leu Asp Ser Asp Gly Ser Phe Phe Leu
        275                 280                 285 tac agc aag ctc acc gtg gac aag agc agg tgg cag cag ggg aac gtc       912
Tyr Ser Lys Leu Thr Val Asp Lys Ser Arg Trp Gln Gln Gly Asn Val
    290                 295                 300 ttc tca tgc tcc gtg atg cat gag gct ctg cac aac cac tac acg cag       960
Phe Ser Cys Ser Val Met His Glu Ala Leu His Asn His Tyr Thr Gln
305                 310                 315                 320 aag agc ctc tcc ctg tct ccg ggt aaa taa                               990
Lys Ser Leu Ser Leu Ser Pro Gly Lys
                325

<210> SEQ ID NO 23
<211> LENGTH: 329
<212> TYPE: PRT
<213> ORGANISM: Artificial sequence
```

```
<220> FEATURE:
<223> OTHER INFORMATION: Synthetic Construct

<400> SEQUENCE: 23

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Ala Pro Gly
    50                  55                  60

Thr Ala Pro Cys Ser Arg Gly Ser Ser Trp Ser Ala Asp Leu Asp Lys
65                  70                  75                  80

Cys Met Asp Cys Ala Ser Cys Arg Ala Arg Pro His Ser Asp Phe Cys
                85                  90                  95

Leu Gly Cys Ala Ala Ala Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 24
<211> LENGTH: 1113
<212> TYPE: DNA
<213> ORGANISM: Artificial sequence
<220> FEATURE:
<223> OTHER INFORMATION: TWEAKR 40trimer-5
<220> FEATURE:
<221> NAME/KEY: CDS
<222> LOCATION: (1)..(1113)
```

<400> SEQUENCE: 24

```
atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc      96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg     144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cca ggc         192
Arg Pro His Ser Asp Phe Cys Leu Gly Cys Ala Ala Ala Pro Gly
    50                  55                  60 acc gcc ccc tgc tcc cgc ggc agc tcc tgg agc gcg gac ctg gac aag     240
Thr Ala Pro Cys Ser Arg Gly Ser Ser Trp Ser Ala Asp Leu Asp Lys
65                  70                  75                  80 tgc atg gac tgc gcg tct tgc agg gcg cga ccg cac agc gac ttc tgc     288
Cys Met Asp Cys Ala Ser Cys Arg Ala Arg Pro His Ser Asp Phe Cys
                85                  90                  95 ctg ggc tgc gct gca gca gca cca ggc acc gcc ccc tgc tcc cgc ggc     336
Leu Gly Cys Ala Ala Ala Ala Pro Gly Thr Ala Pro Cys Ser Arg Gly
            100                 105                 110 agc tcc tgg agc gcg gac ctg gac aag tgc atg gac tgc gcg tct tgc     384
Ser Ser Trp Ser Ala Asp Leu Asp Lys Cys Met Asp Cys Ala Ser Cys
        115                 120                 125 agg gcg cga ccg cac agc gac ttc tgc ctg ggc tgc gct gca gca gac     432
Arg Ala Arg Pro His Ser Asp Phe Cys Leu Gly Cys Ala Ala Ala Asp
    130                 135                 140 aaa act cac aca tgt cca ccg tgc cca gca cct gaa ctc ctg ggg gga     480
Lys Thr His Thr Cys Pro Pro Cys Pro Ala Pro Glu Leu Leu Gly Gly
145                 150                 155                 160 ccg tca gtt ttc ctc ttc ccc cca aaa ccc aag gac acc ctc atg atc     528
Pro Ser Val Phe Leu Phe Pro Pro Lys Pro Lys Asp Thr Leu Met Ile
                165                 170                 175 tcc cgg acc cct gag gtc aca tgc gtg gtg gtg gac gtg agc cac gaa     576
Ser Arg Thr Pro Glu Val Thr Cys Val Val Val Asp Val Ser His Glu
            180                 185                 190 gac cct gag gtc aag ttc aac tgg tac gtg gac ggc gtg gag gtg cat     624
Asp Pro Glu Val Lys Phe Asn Trp Tyr Val Asp Gly Val Glu Val His
        195                 200                 205 aat gcc aag aca aag ccg cgg gag gag cag tac aac agc acg tac cgt     672
Asn Ala Lys Thr Lys Pro Arg Glu Glu Gln Tyr Asn Ser Thr Tyr Arg
    210                 215                 220 gtg gtc agc gtc ctc acc gtc ctg cac cag gac tgg ctg aat ggc aag     720
Val Val Ser Val Leu Thr Val Leu His Gln Asp Trp Leu Asn Gly Lys
225                 230                 235                 240 gag tac aag tgc aag gtc tcc aac aaa gcc ctc cca gcc ccc atc gag     768
Glu Tyr Lys Cys Lys Val Ser Asn Lys Ala Leu Pro Ala Pro Ile Glu
                245                 250                 255 aaa acc atc tcc aaa gcc aaa ggg cag ccc cga gaa cca cag gtg tac     816
Lys Thr Ile Ser Lys Ala Lys Gly Gln Pro Arg Glu Pro Gln Val Tyr
            260                 265                 270 acc ctg ccc cca tcc cgg gat gag ctg acc aag aac cag gtc agc ctg     864
Thr Leu Pro Pro Ser Arg Asp Glu Leu Thr Lys Asn Gln Val Ser Leu
        275                 280                 285 acc tgc ctg gtc aaa ggc ttc tat ccc agc gac atc gcc gtg gag tgg     912
Thr Cys Leu Val Lys Gly Phe Tyr Pro Ser Asp Ile Ala Val Glu Trp
    290                 295                 300 gag agc aat ggg cag ccg gag aac aac tac aag acc acg cct ccc gtg     960
Glu Ser Asn Gly Gln Pro Glu Asn Asn Tyr Lys Thr Thr Pro Pro Val
```

```
                                              -continued

Glu Ser Asn Gly Gln Pro Glu Asn Asn Tyr Lys Thr Thr Pro Pro Val
305                 310                 315                 320 ctg gac tcc gac ggc tcc ttc ttc ctc tac agc aag ctc acc gtg gac      1008
Leu Asp Ser Asp Gly Ser Phe Phe Leu Tyr Ser Lys Leu Thr Val Asp
                325                 330                 335 aag agc agg tgg cag cag ggg aac gtc ttc tca tgc tcc gtg atg cat      1056
Lys Ser Arg Trp Gln Gln Gly Asn Val Phe Ser Cys Ser Val Met His
            340                 345                 350 gag gct ctg cac aac cac tac acg cag aag agc ctc tcc ctg tct ccg      1104
Glu Ala Leu His Asn His Tyr Thr Gln Lys Ser Leu Ser Leu Ser Pro
        355                 360                 365 ggt aaa taa                                                          1113
Gly Lys
    370

<210> SEQ ID NO 25
<211> LENGTH: 370
<212> TYPE: PRT
<213> ORGANISM: Artificial sequence
<220> FEATURE:
<223> OTHER INFORMATION: Synthetic Construct

<400> SEQUENCE: 25

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Ala Pro Gly
    50                  55                  60

Thr Ala Pro Cys Ser Arg Gly Ser Ser Trp Ser Ala Asp Leu Asp Lys
65                  70                  75                  80

Cys Met Asp Cys Ala Ser Cys Arg Ala Arg Pro His Ser Asp Phe Cys
                85                  90                  95

Leu Gly Cys Ala Ala Ala Ala Pro Gly Thr Ala Pro Cys Ser Arg Gly
            100                 105                 110

Ser Ser Trp Ser Ala Asp Leu Asp Lys Cys Met Asp Cys Ala Ser Cys
        115                 120                 125

Arg Ala Arg Pro His Ser Asp Phe Cys Leu Gly Cys Ala Ala Ala Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270
```

```
Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 26
<211> LENGTH: 1236
<212> TYPE: DNA
<213> ORGANISM: Artificial sequence
<220> FEATURE:
<223> OTHER INFORMATION: TWEAKR 40quad-2
<220> FEATURE:
<221> NAME/KEY: CDS
<222> LOCATION: (1)..(1236)

<400> SEQUENCE: 26 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc        96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg       144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cca ggc           192
Arg Pro His Ser Asp Phe Cys Leu Gly Cys Ala Ala Ala Pro Gly
    50                  55                  60 acc gcc ccc tgc tcc cgc ggc agc tcc tgg agc gcg gac ctg gac aag       240
Thr Ala Pro Cys Ser Arg Gly Ser Ser Trp Ser Ala Asp Leu Asp Lys
65                  70                  75                  80 tgc atg gac tgc gcg tct tgc agg gcg cga ccg cac agc gac ttc tgc       288
Cys Met Asp Cys Ala Ser Cys Arg Ala Arg Pro His Ser Asp Phe Cys
                85                  90                  95 ctg ggc tgc gct gca gca gca cca ggc acc gcc ccc tgc tcc cgc ggc       336
Leu Gly Cys Ala Ala Ala Ala Pro Gly Thr Ala Pro Cys Ser Arg Gly
            100                 105                 110 agc tcc tgg agc gcg gac ctg gac aag tgc atg gac tgc gcg tct tgc       384
Ser Ser Trp Ser Ala Asp Leu Asp Lys Cys Met Asp Cys Ala Ser Cys
        115                 120                 125 agg gcg cga ccg cac agc gac ttc tgc ctg ggc tgc gct gca gca gca       432
Arg Ala Arg Pro His Ser Asp Phe Cys Leu Gly Cys Ala Ala Ala Ala
    130                 135                 140 cca ggc acc gcc ccc tgc tcc cgc ggc agc tcc tgg agc gcg gac ctg       480
Pro Gly Thr Ala Pro Cys Ser Arg Gly Ser Ser Trp Ser Ala Asp Leu
145                 150                 155                 160 gac aag tgc atg gac tgc gcg tct tgc agg gcg cga ccg cac agc gac       528
Asp Lys Cys Met Asp Cys Ala Ser Cys Arg Ala Arg Pro His Ser Asp
                165                 170                 175
```

| | | | | | | | | | | | | | | | | |
|---|---|---|---|---|---|---|---|---|---|---|---|---|---|---|---|---|
| ttc | tgc | ctg | ggc | tgc | gct | gca | gca | gac | aaa | act | cac | aca | tgt | cca | ccg | 576 |
| Phe | Cys | Leu | Gly | Cys | Ala | Ala | Ala | Asp | Lys | Thr | His | Thr | Cys | Pro | Pro | |
| | | | 180 | | | | 185 | | | | | 190 | | | | |
| tgc | cca | gca | cct | gaa | ctc | ctg | ggg | gga | ccg | tca | gtt | ttc | ctc | ttc | ccc | 624 |
| Cys | Pro | Ala | Pro | Glu | Leu | Leu | Gly | Gly | Pro | Ser | Val | Phe | Leu | Phe | Pro | |
| | | 195 | | | | 200 | | | | | 205 | | | | | |
| cca | aaa | ccc | aag | gac | acc | ctc | atg | atc | tcc | cgg | acc | cct | gag | gtc | aca | 672 |
| Pro | Lys | Pro | Lys | Asp | Thr | Leu | Met | Ile | Ser | Arg | Thr | Pro | Glu | Val | Thr | |
| | 210 | | | | | 215 | | | | | 220 | | | | | |
| tgc | gtg | gtg | gtg | gac | gtg | agc | cac | gaa | gac | cct | gag | gtc | aag | ttc | aac | 720 |
| Cys | Val | Val | Val | Asp | Val | Ser | His | Glu | Asp | Pro | Glu | Val | Lys | Phe | Asn | |
| 225 | | | | | 230 | | | | | 235 | | | | | 240 | |
| tgg | tac | gtg | gac | ggc | gtg | gag | gtg | cat | aat | gcc | aag | aca | aag | ccg | cgg | 768 |
| Trp | Tyr | Val | Asp | Gly | Val | Glu | Val | His | Asn | Ala | Lys | Thr | Lys | Pro | Arg | |
| | | | | 245 | | | | | 250 | | | | | 255 | | |
| gag | gag | cag | tac | aac | agc | acg | tac | cgt | gtg | gtc | agc | gtc | ctc | acc | gtc | 816 |
| Glu | Glu | Gln | Tyr | Asn | Ser | Thr | Tyr | Arg | Val | Val | Ser | Val | Leu | Thr | Val | |
| | | | 260 | | | | | 265 | | | | | 270 | | | |
| ctg | cac | cag | gac | tgg | ctg | aat | ggc | aag | gag | tac | aag | tgc | aag | gtc | tcc | 864 |
| Leu | His | Gln | Asp | Trp | Leu | Asn | Gly | Lys | Glu | Tyr | Lys | Cys | Lys | Val | Ser | |
| | | 275 | | | | | 280 | | | | | 285 | | | | |
| aac | aaa | gcc | ctc | cca | gcc | ccc | atc | gag | aaa | acc | atc | tcc | aaa | gcc | aaa | 912 |
| Asn | Lys | Ala | Leu | Pro | Ala | Pro | Ile | Glu | Lys | Thr | Ile | Ser | Lys | Ala | Lys | |
| | 290 | | | | | 295 | | | | | 300 | | | | | |
| ggg | cag | ccc | cga | gaa | cca | cag | gtg | tac | acc | ctg | ccc | cca | tcc | cgg | gat | 960 |
| Gly | Gln | Pro | Arg | Glu | Pro | Gln | Val | Tyr | Thr | Leu | Pro | Pro | Ser | Arg | Asp | |
| 305 | | | | | 310 | | | | | 315 | | | | | 320 | |
| gag | ctg | acc | aag | aac | cag | gtc | agc | ctg | acc | tgc | ctg | gtc | aaa | ggc | ttc | 1008 |
| Glu | Leu | Thr | Lys | Asn | Gln | Val | Ser | Leu | Thr | Cys | Leu | Val | Lys | Gly | Phe | |
| | | | | 325 | | | | | 330 | | | | | 335 | | |
| tat | ccc | agc | gac | atc | gcc | gtg | gag | tgg | gag | agc | aat | ggg | cag | ccg | gag | 1056 |
| Tyr | Pro | Ser | Asp | Ile | Ala | Val | Glu | Trp | Glu | Ser | Asn | Gly | Gln | Pro | Glu | |
| | | | 340 | | | | | 345 | | | | | 350 | | | |
| aac | aac | tac | aag | acc | acg | cct | ccc | gtg | ctg | gac | tcc | gac | ggc | tcc | ttc | 1104 |
| Asn | Asn | Tyr | Lys | Thr | Thr | Pro | Pro | Val | Leu | Asp | Ser | Asp | Gly | Ser | Phe | |
| | | 355 | | | | | 360 | | | | | 365 | | | | |
| ttc | ctc | tac | agc | aag | ctc | acc | gtg | gac | aag | agc | agg | tgg | cag | cag | ggg | 1152 |
| Phe | Leu | Tyr | Ser | Lys | Leu | Thr | Val | Asp | Lys | Ser | Arg | Trp | Gln | Gln | Gly | |
| | 370 | | | | | 375 | | | | | 380 | | | | | |
| aac | gtc | ttc | tca | tgc | tcc | gtg | atg | cat | gag | gct | ctg | cac | aac | cac | tac | 1200 |
| Asn | Val | Phe | Ser | Cys | Ser | Val | Met | His | Glu | Ala | Leu | His | Asn | His | Tyr | |
| 385 | | | | | 390 | | | | | 395 | | | | | 400 | |
| acg | cag | aag | agc | ctc | tcc | ctg | tct | ccg | ggt | aaa | taa | | | | | 1236 |
| Thr | Gln | Lys | Ser | Leu | Ser | Leu | Ser | Pro | Gly | Lys | | | | | | |
| | | | | 405 | | | | | 410 | | | | | | | |

```
<210> SEQ ID NO 27
<211> LENGTH: 411
<212> TYPE: PRT
<213> ORGANISM: Artificial sequence
<220> FEATURE:
<223> OTHER INFORMATION: Synthetic Construct

<400> SEQUENCE: 27
```

| | | | | | | | | | | | | | | |
|---|---|---|---|---|---|---|---|---|---|---|---|---|---|---|
| Met | Glu | Thr | Asp | Thr | Leu | Leu | Leu | Trp | Val | Leu | Leu | Leu | Trp | Val | Pro |
| 1 | | | | 5 | | | | | 10 | | | | | 15 | |
| Gly | Ser | Thr | Gly | Ala | Pro | Gly | Thr | Ala | Pro | Cys | Ser | Arg | Gly | Ser | Ser |
| | | | 20 | | | | | 25 | | | | | 30 | | |
| Trp | Ser | Ala | Asp | Leu | Asp | Lys | Cys | Met | Asp | Cys | Ala | Ser | Cys | Arg | Ala |
| | | 35 | | | | | 40 | | | | | 45 | | | |

```
Arg Pro His Ser Asp Phe Cys Leu Gly Cys Ala Ala Ala Pro Gly
 50                  55                  60

Thr Ala Pro Cys Ser Arg Gly Ser Ser Trp Ser Ala Asp Leu Asp Lys
 65                  70                  75                  80

Cys Met Asp Cys Ala Ser Cys Arg Ala Arg Pro His Ser Asp Phe Cys
                 85                  90                  95

Leu Gly Cys Ala Ala Ala Pro Gly Thr Ala Pro Cys Ser Arg Gly
            100                 105                 110

Ser Ser Trp Ser Ala Asp Leu Asp Lys Cys Met Asp Cys Ala Ser Cys
        115                 120                 125

Arg Ala Arg Pro His Ser Asp Phe Cys Leu Gly Cys Ala Ala Ala
    130                 135                 140

Pro Gly Thr Ala Pro Cys Ser Arg Gly Ser Ser Trp Ser Ala Asp Leu
145                 150                 155                 160

Asp Lys Cys Met Asp Cys Ala Ser Cys Arg Ala Arg Pro His Ser Asp
                165                 170                 175

Phe Cys Leu Gly Cys Ala Ala Ala Asp Lys Thr His Thr Cys Pro Pro
            180                 185                 190

Cys Pro Ala Pro Glu Leu Leu Gly Gly Pro Ser Val Phe Leu Phe Pro
        195                 200                 205

Pro Lys Pro Lys Asp Thr Leu Met Ile Ser Arg Thr Pro Glu Val Thr
210                 215                 220

Cys Val Val Val Asp Val Ser His Glu Asp Pro Glu Val Lys Phe Asn
225                 230                 235                 240

Trp Tyr Val Asp Gly Val Glu Val His Asn Ala Lys Thr Lys Pro Arg
                245                 250                 255

Glu Glu Gln Tyr Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Ala Leu Pro Ala Pro Ile Glu Lys Thr Ile Ser Lys Ala Lys
    290                 295                 300

Gly Gln Pro Arg Glu Pro Gln Val Tyr Thr Leu Pro Pro Ser Arg Asp
305                 310                 315                 320

Glu Leu Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Lys Leu Thr Val Asp Lys Ser Arg Trp Gln Gln Gly
    370                 375                 380

Asn Val Phe Ser Cys Ser Val Met His Glu Ala Leu His Asn His Tyr
385                 390                 395                 400

Thr Gln Lys Ser Leu Ser Leu Ser Pro Gly Lys
                405                 410

<210> SEQ ID NO 28
<211> LENGTH: 1359
<212> TYPE: DNA
<213> ORGANISM: Artificial sequence
<220> FEATURE:
<223> OTHER INFORMATION: TWEAKR 40quint-1
<220> FEATURE:
<221> NAME/KEY: CDS
<222> LOCATION: (1)..(1359)
```

<400> SEQUENCE: 28

```
atg gag aca gac aca ctc ctg cta tgg gta ctg ctg ctc tgg gtt cca       48
Met Glu Thr Asp Thr Leu Leu Leu Trp Val Leu Leu Leu Trp Val Pro
 1               5                  10                  15 ggt tcc acc ggt gca cca ggc acc gcc ccc tgc tcc cgc ggc agc tcc       96
Gly Ser Thr Gly Ala Pro Gly Thr Ala Pro Cys Ser Arg Gly Ser Ser
             20                  25                  30 tgg agc gcg gac ctg gac aag tgc atg gac tgc gcg tct tgc agg gcg      144
Trp Ser Ala Asp Leu Asp Lys Cys Met Asp Cys Ala Ser Cys Arg Ala
         35                  40                  45 cga ccg cac agc gac ttc tgc ctg ggc tgc gct gca gca cca ggc          192
Arg Pro His Ser Asp Phe Cys Leu Gly Cys Ala Ala Ala Pro Gly
     50                  55                  60 acc gcc ccc tgc tcc cgc ggc agc tcc tgg agc gcg gac ctg gac aag      240
Thr Ala Pro Cys Ser Arg Gly Ser Ser Trp Ser Ala Asp Leu Asp Lys
 65                  70                  75                  80 tgc atg gac tgc gcg tct tgc agg gcg cga ccg cac agc gac ttc tgc      288
Cys Met Asp Cys Ala Ser Cys Arg Ala Arg Pro His Ser Asp Phe Cys
                 85                  90                  95 ctg ggc tgc gct gca gca cca ggc acc gcc ccc tgc tcc cgc ggc          336
Leu Gly Cys Ala Ala Ala Pro Gly Thr Ala Pro Cys Ser Arg Gly
             100                 105                 110 agc tcc tgg agc gcg gac ctg gac aag tgc atg gac tgc gcg tct tgc      384
Ser Ser Trp Ser Ala Asp Leu Asp Lys Cys Met Asp Cys Ala Ser Cys
         115                 120                 125 agg gcg cga ccg cac agc gac ttc tgc ctg ggc tgc gct gca gca          432
Arg Ala Arg Pro His Ser Asp Phe Cys Leu Gly Cys Ala Ala Ala
     130                 135                 140 cca ggc acc gcc ccc tgc tcc cgc ggc agc tcc tgg agc gcg gac ctg      480
Pro Gly Thr Ala Pro Cys Ser Arg Gly Ser Ser Trp Ser Ala Asp Leu
145                 150                 155                 160 gac aag tgc atg gac tgc gcg tct tgc agg gcg cga ccg cac agc gac      528
Asp Lys Cys Met Asp Cys Ala Ser Cys Arg Ala Arg Pro His Ser Asp
                 165                 170                 175 ttc tgc ctg ggc tgc gct gca gca gca cca ggc acc gcc ccc tgc tcc      576
Phe Cys Leu Gly Cys Ala Ala Ala Ala Pro Gly Thr Ala Pro Cys Ser
             180                 185                 190 cgc ggc agc tcc tgg agc gcg gac ctg gac aag tgc atg gac tgc gcg      624
Arg Gly Ser Ser Trp Ser Ala Asp Leu Asp Lys Cys Met Asp Cys Ala
         195                 200                 205 tct tgc agg gcg cga ccg cac agc gac ttc tgc ctg ggc tgc gct gca      672
Ser Cys Arg Ala Arg Pro His Ser Asp Phe Cys Leu Gly Cys Ala Ala
     210                 215                 220 gca gac aaa act cac aca tgt cca ccg tgc cca gca cct gaa ctc ctg      720
Ala Asp Lys Thr His Thr Cys Pro Pro Cys Pro Ala Pro Glu Leu Leu
225                 230                 235                 240 ggg gga ccg tca gtt ttc ctc ttc ccc cca aaa ccc aag gac acc ctc      768
Gly Gly Pro Ser Val Phe Leu Phe Pro Pro Lys Pro Lys Asp Thr Leu
                 245                 250                 255 atg atc tcc cgg acc cct gag gtc aca tgc gtg gtg gtg gac gtg agc      816
Met Ile Ser Arg Thr Pro Glu Val Thr Cys Val Val Val Asp Val Ser
             260                 265                 270 cac gaa gac cct gag gtc aag ttc aac tgg tac gtg gac ggc gtg gag      864
His Glu Asp Pro Glu Val Lys Phe Asn Trp Tyr Val Asp Gly Val Glu
         275                 280                 285 gtg cat aat gcc aag aca aag ccg cgg gag gag cag tac aac agc acg      912
Val His Asn Ala Lys Thr Lys Pro Arg Glu Glu Gln Tyr Asn Ser Thr
     290                 295                 300
```

```
tac cgt gtg gtc agc gtc ctc acc gtc ctg cac cag gac tgg ctg aat      960
Tyr Arg Val Val Ser Val Leu Thr Val Leu His Gln Asp Trp Leu Asn
305                 310                 315                 320 ggc aag gag tac aag tgc aag gtc tcc aac aaa gcc ctc cca gcc ccc     1008
Gly Lys Glu Tyr Lys Cys Lys Val Ser Asn Lys Ala Leu Pro Ala Pro
            325                 330                 335 atc gag aaa acc atc tcc aaa gcc aaa ggg cag ccc cga gaa cca cag     1056
Ile Glu Lys Thr Ile Ser Lys Ala Lys Gly Gln Pro Arg Glu Pro Gln
        340                 345                 350 gtg tac acc ctg ccc cca tcc cgg gat gag ctg acc aag aac cag gtc     1104
Val Tyr Thr Leu Pro Pro Ser Arg Asp Glu Leu Thr Lys Asn Gln Val
    355                 360                 365 agc ctg acc tgc ctg gtc aaa ggc ttc tat ccc agc gac atc gcc gtg     1152
Ser Leu Thr Cys Leu Val Lys Gly Phe Tyr Pro Ser Asp Ile Ala Val
370                 375                 380 gag tgg gag agc aat ggg cag ccg gag aac aac tac aag acc acg cct     1200
Glu Trp Glu Ser Asn Gly Gln Pro Glu Asn Asn Tyr Lys Thr Thr Pro
385                 390                 395                 400 ccc gtg ctg gac tcc gac ggc tcc ttc ttc ctc tac agc aag ctc acc     1248
Pro Val Leu Asp Ser Asp Gly Ser Phe Phe Leu Tyr Ser Lys Leu Thr
            405                 410                 415 gtg gac aag agc agg tgg cag cag ggg aac gtc ttc tca tgc tcc gtg     1296
Val Asp Lys Ser Arg Trp Gln Gln Gly Asn Val Phe Ser Cys Ser Val
        420                 425                 430 atg cat gag gct ctg cac aac cac tac acg cag aag agc ctc tcc ctg     1344
Met His Glu Ala Leu His Asn His Tyr Thr Gln Lys Ser Leu Ser Leu
    435                 440                 445 tct ccg ggt aaa taa                                                 1359
Ser Pro Gly Lys
450

<210> SEQ ID NO 29
<211> LENGTH: 452
<212> TYPE: PRT
<213> ORGANISM: Artificial sequence
<220> FEATURE:
<223> OTHER INFORMATION: Synthetic Construct

<400> SEQUENCE: 29

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Ala Pro Gly
    50                  55                  60

Thr Ala Pro Cys Ser Arg Gly Ser Ser Trp Ser Ala Asp Leu Asp Lys
65                  70                  75                  80

Cys Met Asp Cys Ala Ser Cys Arg Ala Arg Pro His Ser Asp Phe Cys
                85                  90                  95

Leu Gly Cys Ala Ala Ala Pro Gly Thr Ala Pro Cys Ser Arg Gly
            100                 105                 110

Ser Ser Trp Ser Ala Asp Leu Asp Lys Cys Met Asp Cys Ala Ser Cys
        115                 120                 125

Arg Ala Arg Pro His Ser Asp Phe Cys Leu Gly Cys Ala Ala Ala
    130                 135                 140

Pro Gly Thr Ala Pro Cys Ser Arg Gly Ser Ser Trp Ser Ala Asp Leu
145                 150                 155                 160
```

Asp Lys Cys Met Asp Cys Ala Ser Cys Arg Ala Arg Pro His Ser Asp
            165                 170                 175

Phe Cys Leu Gly Cys Ala Ala Ala Pro Gly Thr Ala Pro Cys Ser
        180                 185                 190

Arg Gly Ser Ser Trp Ser Ala Asp Leu Asp Lys Cys Met Asp Cys Ala
    195                 200                 205

Ser Cys Arg Ala Arg Pro His Ser Asp Phe Cys Leu Gly Cys Ala Ala
    210                 215                 220

Ala Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 30
<211> LENGTH: 876
<212> TYPE: DNA
<213> ORGANISM: Artificial sequence
<220> FEATURE:
<223> OTHER INFORMATION: TWEAKR 43mono-F4
<220> FEATURE:
<221> NAME/KEY: CDS
<222> LOCATION: (1)..(876)

<400> SEQUENCE: 30 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc      96
Gly Ser Thr Gly Ala Pro Gly Thr Ala Pro Cys Ser Arg Gly Ser Ser
            20                  25                  30

```
tgg agc gcg gac ctg gac aag tgc atg gac tgc gcg tct tgc agg gcg      144
Trp Ser Ala Asp Leu Asp Lys Cys Met Asp Cys Ala Ser Cys Arg Ala
         35                  40                  45 cga ccg cac agc gac ttc tgc ctg ggc tgc gct gca cct cct gcc          192
Arg Pro His Ser Asp Phe Cys Leu Gly Cys Ala Ala Pro Pro Ala
 50                  55                  60 gac aaa act cac aca tgt cca ccg tgc cca gca cct gaa ctc ctg ggg      240
Asp Lys Thr His Thr Cys Pro Pro Cys Pro Ala Pro Glu Leu Leu Gly
 65                  70                  75                  80 gga ccg tca gtt ttc ctc ttc ccc cca aaa ccc aag gac acc ctc atg      288
Gly Pro Ser Val Phe Leu Phe Pro Pro Lys Pro Lys Asp Thr Leu Met
                 85                  90                  95 atc tcc cgg acc cct gag gtc aca tgc gtg gtg gtg gac gtg agc cac      336
Ile Ser Arg Thr Pro Glu Val Thr Cys Val Val Val Asp Val Ser His
             100                 105                 110 gaa gac cct gag gtc aag ttc aac tgg tac gtg gac ggc gtg gag gtg      384
Glu Asp Pro Glu Val Lys Phe Asn Trp Tyr Val Asp Gly Val Glu Val
         115                 120                 125 cat aat gcc aag aca aag ccg cgg gag gag cag tac aac agc acg tac      432
His Asn Ala Lys Thr Lys Pro Arg Glu Glu Gln Tyr Asn Ser Thr Tyr
130                 135                 140 cgt gtg gtc agc gtc ctc acc gtc ctg cac cag gac tgg ctg aat ggc      480
Arg Val Val Ser Val Leu Thr Val Leu His Gln Asp Trp Leu Asn Gly
145                 150                 155                 160 aag gag tac aag tgc aag gtc tcc aac aaa gcc ctc cca gcc ccc atc      528
Lys Glu Tyr Lys Cys Lys Val Ser Asn Lys Ala Leu Pro Ala Pro Ile
                165                 170                 175 gag aaa acc atc tcc aaa gcc aaa ggg cag ccc cga gaa cca cag gtg      576
Glu Lys Thr Ile Ser Lys Ala Lys Gly Gln Pro Arg Glu Pro Gln Val
            180                 185                 190 tac acc ctg ccc cca tcc cgg gat gag ctg acc aag aac cag gtc agc      624
Tyr Thr Leu Pro Pro Ser Arg Asp Glu Leu Thr Lys Asn Gln Val Ser
        195                 200                 205 ctg acc tgc ctg gtc aaa ggc ttc tat ccc agc gac atc gcc gtg gag      672
Leu Thr Cys Leu Val Lys Gly Phe Tyr Pro Ser Asp Ile Ala Val Glu
    210                 215                 220 tgg gag agc aat ggg cag ccg gag aac aac tac aag acc acg cct ccc      720
Trp Glu Ser Asn Gly Gln Pro Glu Asn Asn Tyr Lys Thr Thr Pro Pro
225                 230                 235                 240 gtg ctg gac tcc gac ggc tcc ttc ttc ctc tac agc aag ctc acc gtg      768
Val Leu Asp Ser Asp Gly Ser Phe Phe Leu Tyr Ser Lys Leu Thr Val
                245                 250                 255 gac aag agc agg tgg cag cag ggg aac gtc ttc tca tgc tcc gtg atg      816
Asp Lys Ser Arg Trp Gln Gln Gly Asn Val Phe Ser Cys Ser Val Met
            260                 265                 270 cat gag gct ctg cac aac cac tac acg cag aag agc ctc tcc ctg tct      864
His Glu Ala Leu His Asn His Tyr Thr Gln Lys Ser Leu Ser Leu Ser
        275                 280                 285 ccg ggt aaa taa                                                      876
Pro Gly Lys
    290
```

<210> SEQ ID NO 31
<211> LENGTH: 291
<212> TYPE: PRT
<213> ORGANISM: Artificial sequence
<220> FEATURE:
<223> OTHER INFORMATION: Synthetic Construct

<400> SEQUENCE: 31

Met Glu Thr Asp Thr Leu Leu Leu Trp Val Leu Leu Leu Trp Val Pro

```
                      1               5                  10                 15
Gly Ser Thr Gly Ala Pro Gly Thr Ala Pro Cys Ser Arg Gly Ser Ser
                20                  25                 30

Trp Ser Ala Asp Leu Asp Lys Cys Met Asp Cys Ala Ser Cys Arg Ala
                35                  40                 45

Arg Pro His Ser Asp Phe Cys Leu Gly Cys Ala Ala Pro Pro Ala
    50                  55                  60

Asp Lys Thr His Thr Cys Pro Pro Cys Pro Ala Pro Glu Leu Leu Gly
65                  70                  75                 80

Gly Pro Ser Val Phe Leu Phe Pro Pro Lys Pro Lys Asp Thr Leu Met
                85                  90                 95

Ile Ser Arg Thr Pro Glu Val Thr Cys Val Val Val Asp Val Ser His
                100                 105                110

Glu Asp Pro Glu Val Lys Phe Asn Trp Tyr Val Asp Gly Val Glu Val
                115                 120                125

His Asn Ala Lys Thr Lys Pro Arg Glu Glu Gln Tyr Asn Ser Thr Tyr
    130                 135                 140

Arg Val Val Ser Val Leu Thr Val Leu His Gln Asp Trp Leu Asn Gly
145                 150                 155                160

Lys Glu Tyr Lys Cys Lys Val Ser Asn Lys Ala Leu Pro Ala Pro Ile
                165                 170                175

Glu Lys Thr Ile Ser Lys Ala Lys Gly Gln Pro Arg Glu Pro Gln Val
                180                 185                190

Tyr Thr Leu Pro Pro Ser Arg Asp Glu Leu Thr Lys Asn Gln Val Ser
                195                 200                205

Leu Thr Cys Leu Val Lys Gly Phe Tyr Pro Ser Asp Ile Ala Val Glu
    210                 215                 220

Trp Glu Ser Asn Gly Gln Pro Glu Asn Asn Tyr Lys Thr Thr Pro Pro
225                 230                 235                240

Val Leu Asp Ser Asp Gly Ser Phe Phe Leu Tyr Ser Lys Leu Thr Val
                245                 250                255

Asp Lys Ser Arg Trp Gln Gln Gly Asn Val Phe Ser Cys Ser Val Met
                260                 265                270

His Glu Ala Leu His Asn His Tyr Thr Gln Lys Ser Leu Ser Leu Ser
    275                 280                 285

Pro Gly Lys
    290

<210> SEQ ID NO 32
<211> LENGTH: 1008
<212> TYPE: DNA
<213> ORGANISM: Artificial sequence
<220> FEATURE:
<223> OTHER INFORMATION: TWEAKR 43dimer-F2
<220> FEATURE:
<221> NAME/KEY: CDS
<222> LOCATION: (1)..(1008)

<400> SEQUENCE: 32 atg gag aca gac aca ctc ctg cta tgg gta ctg ctg ctc tgg gtt cca       48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc       96
Gly Ser Thr Gly Ala Pro Gly Thr Ala Pro Cys Ser Arg Gly Ser Ser
                20                  25                  30 tgg agc gcg gac ctg gac aag tgc atg gac tgc gcg tct tgc agg gcg      144
Trp Ser Ala Asp Leu Asp Lys Cys Met Asp Cys Ala Ser Cys Arg Ala
```

-continued

```
                 35                  40                  45
cga ccg cac agc gac ttc tgc ctg ggc tgc gct gca gca cct cct gcc       192
Arg Pro His Ser Asp Phe Cys Leu Gly Cys Ala Ala Pro Pro Ala
         50                  55                  60 gca cca ggc acc gcc ccc tgc tcc cgc ggc agc tcc tgg agc gcg gac       240
Ala Pro Gly Thr Ala Pro Cys Ser Arg Gly Ser Ser Trp Ser Ala Asp
 65                  70                  75                  80 ctg gac aag tgc atg gac tgc gcg tct tgc agg gcg cga ccg cac agc       288
Leu Asp Lys Cys Met Asp Cys Ala Ser Cys Arg Ala Arg Pro His Ser
                 85                  90                  95 gac ttc tgc ctg ggc tgc gct gca gca cct cct gcc gac aaa act cac       336
Asp Phe Cys Leu Gly Cys Ala Ala Ala Pro Pro Ala Asp Lys Thr His
             100                 105                 110 aca tgt cca ccg tgc cca gca cct gaa ctc ctg ggg gga ccg tca gtt       384
Thr Cys Pro Pro Cys Pro Ala Pro Glu Leu Leu Gly Gly Pro Ser Val
             115                 120                 125 ttc ctc ttc ccc cca aaa ccc aag gac acc ctc atg atc tcc cgg acc       432
Phe Leu Phe Pro Pro Lys Pro Lys Asp Thr Leu Met Ile Ser Arg Thr
    130                 135                 140 cct gag gtc aca tgc gtg gtg gtg gac gtg agc cac gaa gac cct gag       480
Pro Glu Val Thr Cys Val Val Val Asp Val Ser His Glu Asp Pro Glu
145                 150                 155                 160 gtc aag ttc aac tgg tac gtg gac ggc gtg gag gtg cat aat gcc aag       528
Val Lys Phe Asn Trp Tyr Val Asp Gly Val Glu Val His Asn Ala Lys
                165                 170                 175 aca aag ccg cgg gag gag cag tac aac agc acg tac cgt gtg gtc agc       576
Thr Lys Pro Arg Glu Glu Gln Tyr Asn Ser Thr Tyr Arg Val Val Ser
            180                 185                 190 gtc ctc acc gtc ctg cac cag gac tgg ctg aat ggc aag gag tac aag       624
Val Leu Thr Val Leu His Gln Asp Trp Leu Asn Gly Lys Glu Tyr Lys
        195                 200                 205 tgc aag gtc tcc aac aaa gcc ctc cca gcc ccc atc gag aaa acc atc       672
Cys Lys Val Ser Asn Lys Ala Leu Pro Ala Pro Ile Glu Lys Thr Ile
    210                 215                 220 tcc aaa gcc aaa ggg cag ccc cga gaa cca cag gtg tac acc ctg ccc       720
Ser Lys Ala Lys Gly Gln Pro Arg Glu Pro Gln Val Tyr Thr Leu Pro
225                 230                 235                 240 cca tcc cgg gat gag ctg acc aag aac cag gtc agc ctg acc tgc ctg       768
Pro Ser Arg Asp Glu Leu Thr Lys Asn Gln Val Ser Leu Thr Cys Leu
                245                 250                 255 gtc aaa ggc ttc tat ccc agc gac atc gcc gtg gag tgg gag agc aat       816
Val Lys Gly Phe Tyr Pro Ser Asp Ile Ala Val Glu Trp Glu Ser Asn
            260                 265                 270 ggg cag ccg gag aac aac tac aag acc acg cct ccc gtg ctg gac tcc       864
Gly Gln Pro Glu Asn Asn Tyr Lys Thr Thr Pro Pro Val Leu Asp Ser
        275                 280                 285 gac ggc tcc ttc ttc ctc tac agc aag ctc acc gtg gac aag agc agg       912
Asp Gly Ser Phe Phe Leu Tyr Ser Lys Leu Thr Val Asp Lys Ser Arg
    290                 295                 300 tgg cag cag ggg aac gtc ttc tca tgc tcc gtg atg cat gag gct ctg       960
Trp Gln Gln Gly Asn Val Phe Ser Cys Ser Val Met His Glu Ala Leu
305                 310                 315                 320 cac aac cac tac acg cag aag agc ctc tcc ctg tct ccg ggt aaa taa      1008
His Asn His Tyr Thr Gln Lys Ser Leu Ser Leu Ser Pro Gly Lys
                325                 330                 335
```

<210> SEQ ID NO 33
<211> LENGTH: 335
<212> TYPE: PRT
<213> ORGANISM: Artificial sequence
<220> FEATURE:
<223> OTHER INFORMATION: Synthetic Construct

<400> SEQUENCE: 33

```
Met Glu Thr Asp Thr Leu Leu Leu Trp Val Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
            35                  40                  45

Arg Pro His Ser Asp Phe Cys Leu Gly Cys Ala Ala Pro Pro Ala
50                      55                  60

Ala Pro Gly Thr Ala Pro Cys Ser Arg Gly Ser Ser Trp Ser Ala Asp
65                  70                  75                  80

Leu Asp Lys Cys Met Asp Cys Ala Ser Cys Arg Ala Arg Pro His Ser
                85                  90                  95

Asp Phe Cys Leu Gly Cys Ala Ala Pro Pro Ala Asp Lys Thr His
                100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
                195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Asp Glu Leu Thr Lys Asn Gln Val Ser Leu Thr Cys Leu
            245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335
```

<210> SEQ ID NO 34
<211> LENGTH: 1140
<212> TYPE: DNA
<213> ORGANISM: Artificial
<220> FEATURE:
<223> OTHER INFORMATION: TWEAKR 43trimer-1
<220> FEATURE:
<221> NAME/KEY: CDS
<222> LOCATION: (1)..(1140)

```
<400> SEQUENCE: 34 atg gag aca gac aca ctc ctg cta tgg gta ctg ctg ctc tgg gtt cca    48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc    96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg   144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cct cct gcc   192
Arg Pro His Ser Asp Phe Cys Leu Gly Cys Ala Ala Ala Pro Pro Ala
    50                  55                  60 gca cca ggc acc gcc ccc tgc tcc cgc ggc agc tcc tgg agc gcg gac   240
Ala Pro Gly Thr Ala Pro Cys Ser Arg Gly Ser Ser Trp Ser Ala Asp
65                  70                  75                  80 ctg gac aag tgc atg gac tgc gcg tct tgc agg gcg cga ccg cac agc   288
Leu Asp Lys Cys Met Asp Cys Ala Ser Cys Arg Ala Arg Pro His Ser
                85                  90                  95 gac ttc tgc ctg ggc tgc gct gca gca cct cct gcc gca cca ggc acc   336
Asp Phe Cys Leu Gly Cys Ala Ala Ala Pro Pro Ala Ala Pro Gly Thr
            100                 105                 110 gcc ccc tgc tcc cgc ggc agc tcc tgg agc gcg gac ctg gac aag tgc   384
Ala Pro Cys Ser Arg Gly Ser Ser Trp Ser Ala Asp Leu Asp Lys Cys
        115                 120                 125 atg gac tgc gcg tct tgc agg gcg cga ccg cac agc gac ttc tgc ctg   432
Met Asp Cys Ala Ser Cys Arg Ala Arg Pro His Ser Asp Phe Cys Leu
    130                 135                 140 ggc tgc gct gca gca cct cct gcc gac aaa act cac aca tgt cca ccg   480
Gly Cys Ala Ala Ala Pro Pro Ala Asp Lys Thr His Thr Cys Pro Pro
145                 150                 155                 160 tgc cca gca cct gaa ctc ctg ggg gga ccg tca gtt ttc ctc ttc ccc   528
Cys Pro Ala Pro Glu Leu Leu Gly Gly Pro Ser Val Phe Leu Phe Pro
                165                 170                 175 cca aaa ccc aag gac acc ctc atg atc tcc cgg acc cct gag gtc aca   576
Pro Lys Pro Lys Asp Thr Leu Met Ile Ser Arg Thr Pro Glu Val Thr
            180                 185                 190 tgc gtg gtg gtg gac gtg agc cac gaa gac cct gag gtc aag ttc aac   624
Cys Val Val Val Asp Val Ser His Glu Asp Pro Glu Val Lys Phe Asn
        195                 200                 205 tgg tac gtg gac ggc gtg gag gtg cat aat gcc aag aca aag ccg cgg   672
Trp Tyr Val Asp Gly Val Glu Val His Asn Ala Lys Thr Lys Pro Arg
    210                 215                 220 gag gag cag tac aac agc acg tac cgt gtg gtc agc gtc ctc acc gtc   720
Glu Glu Gln Tyr Asn Ser Thr Tyr Arg Val Val Ser Val Leu Thr Val
225                 230                 235                 240 ctg cac cag gac tgg ctg aat ggc aag gag tac aag tgc aag gtc tcc   768
Leu His Gln Asp Trp Leu Asn Gly Lys Glu Tyr Lys Cys Lys Val Ser
                245                 250                 255 aac aaa gcc ctc cca gcc ccc atc gag aaa acc atc tcc aaa gcc aaa   816
Asn Lys Ala Leu Pro Ala Pro Ile Glu Lys Thr Ile Ser Lys Ala Lys
            260                 265                 270 ggg cag ccc cga gaa cca cag gtg tac acc ctg ccc cca tcc cgg gat   864
Gly Gln Pro Arg Glu Pro Gln Val Tyr Thr Leu Pro Pro Ser Arg Asp
        275                 280                 285 gag ctg acc aag aac cag gtc agc ctg acc tgc ctg gtc aaa ggc ttc   912
Glu Leu Thr Lys Asn Gln Val Ser Leu Thr Cys Leu Val Lys Gly Phe
    290                 295                 300 tat ccc agc gac atc gcc gtg gag tgg gag agc aat ggg cag ccg gag   960
```

```
Tyr Pro Ser Asp Ile Ala Val Glu Trp Glu Ser Asn Gly Gln Pro Glu
305                 310                 315                 320 aac aac tac aag acc acg cct ccc gtg ctg gac tcc gac ggc tcc ttc      1008
Asn Asn Tyr Lys Thr Thr Pro Pro Val Leu Asp Ser Asp Gly Ser Phe
                325                 330                 335 ttc ctc tac agc aag ctc acc gtg gac aag agc agg tgg cag cag ggg      1056
Phe Leu Tyr Ser Lys Leu Thr Val Asp Lys Ser Arg Trp Gln Gln Gly
            340                 345                 350 aac gtc ttc tca tgc tcc gtg atg cat gag gct ctg cac aac cac tac      1104
Asn Val Phe Ser Cys Ser Val Met His Glu Ala Leu His Asn His Tyr
        355                 360                 365 acg cag aag agc ctc tcc ctg tct ccg ggt aaa taa                      1140
Thr Gln Lys Ser Leu Ser Leu Ser Pro Gly Lys
370                 375

<210> SEQ ID NO 35
<211> LENGTH: 379
<212> TYPE: PRT
<213> ORGANISM: Artificial
<220> FEATURE:
<223> OTHER INFORMATION: Synthetic Construct

<400> SEQUENCE: 35

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Pro Pro Ala
    50                  55                  60

Ala Pro Gly Thr Ala Pro Cys Ser Arg Gly Ser Ser Trp Ser Ala Asp
65                  70                  75                  80

Leu Asp Lys Cys Met Asp Cys Ala Ser Cys Arg Ala Arg Pro His Ser
                85                  90                  95

Asp Phe Cys Leu Gly Cys Ala Ala Pro Ala Ala Pro Gly Thr
            100                 105                 110

Ala Pro Cys Ser Arg Gly Ser Ser Trp Ser Ala Asp Leu Asp Lys Cys
        115                 120                 125

Met Asp Cys Ala Ser Cys Arg Ala Arg Pro His Ser Asp Phe Cys Leu
    130                 135                 140

Gly Cys Ala Ala Ala Pro Pro Ala Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270
```

```
Gly Gln Pro Arg Glu Pro Gln Val Tyr Thr Leu Pro Pro Ser Arg Asp
            275                 280                 285

Glu Leu Thr Lys Asn Gln Val Ser Leu Thr Cys Leu Val Lys Gly Phe
        290                 295                 300

Tyr Pro Ser Asp Ile Ala Val Glu Trp Glu Ser Asn Gly Gln Pro Glu
305                 310                 315                 320

Asn Asn Tyr Lys Thr Thr Pro Pro Val Leu Asp Ser Asp Gly Ser Phe
                325                 330                 335

Phe Leu Tyr Ser Lys Leu Thr Val Asp Lys Ser Arg Trp Gln Gln Gly
            340                 345                 350

Asn Val Phe Ser Cys Ser Val Met His Glu Ala Leu His Asn His Tyr
        355                 360                 365

Thr Gln Lys Ser Leu Ser Leu Ser Pro Gly Lys
    370                 375

<210> SEQ ID NO 36
<211> LENGTH: 1272
<212> TYPE: DNA
<213> ORGANISM: Artificial sequence
<220> FEATURE:
<223> OTHER INFORMATION: TWEAKR 43quad-2
<220> FEATURE:
<221> NAME/KEY: CDS
<222> LOCATION: (1)..(1272)

<400> SEQUENCE: 36 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                  10                  15 ggt tcc acc ggt gca cca ggc acc gcc ccc tgc tcc cgc ggc agc tcc      96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg     144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cct cct gcc     192
Arg Pro His Ser Asp Phe Cys Leu Gly Cys Ala Ala Ala Pro Pro Ala
    50                  55                  60 gca cca ggc acc gcc ccc tgc tcc cgc ggc agc tcc tgg agc gcg gac     240
Ala Pro Gly Thr Ala Pro Cys Ser Arg Gly Ser Ser Trp Ser Ala Asp
65                  70                  75                  80 ctg gac aag tgc atg gac tgc gcg tct tgc agg gcg cga ccg cac agc     288
Leu Asp Lys Cys Met Asp Cys Ala Ser Cys Arg Ala Arg Pro His Ser
                85                  90                  95 gac ttc tgc ctg ggc tgc gct gca gca cct cct gcc gca cca ggc acc     336
Asp Phe Cys Leu Gly Cys Ala Ala Ala Pro Pro Ala Ala Pro Gly Thr
            100                 105                 110 gcc ccc tgc tcc cgc ggc agc tcc tgg agc gcg gac ctg gac aag tgc     384
Ala Pro Cys Ser Arg Gly Ser Ser Trp Ser Ala Asp Leu Asp Lys Cys
        115                 120                 125 atg gac tgc gcg tct tgc agg gcg cga ccg cac agc gac ttc tgc ctg     432
Met Asp Cys Ala Ser Cys Arg Ala Arg Pro His Ser Asp Phe Cys Leu
    130                 135                 140 ggc tgc gct gca gca cct cct gcc gca cca ggc acc gcc ccc tgc tcc     480
Gly Cys Ala Ala Ala Pro Pro Ala Ala Pro Gly Thr Ala Pro Cys Ser
145                 150                 155                 160 cgc ggc agc tcc tgg agc gcg gac ctg gac aag tgc atg gac tgc gcg     528
Arg Gly Ser Ser Trp Ser Ala Asp Leu Asp Lys Cys Met Asp Cys Ala
                165                 170                 175
```

```
tct tgc agg gcg cga ccg cac agc gac ttc tgc ctg ggc tgc gct gca      576
Ser Cys Arg Ala Arg Pro His Ser Asp Phe Cys Leu Gly Cys Ala Ala
        180                 185                 190 gca cct cct gcc gac aaa act cac aca tgt cca ccg tgc cca gca cct      624
Ala Pro Pro Ala Asp Lys Thr His Thr Cys Pro Pro Cys Pro Ala Pro
        195                 200                 205 gaa ctc ctg ggg gga ccg tca gtt ttc ctc ttc ccc cca aaa ccc aag      672
Glu Leu Leu Gly Gly Pro Ser Val Phe Leu Phe Pro Pro Lys Pro Lys
    210                 215                 220 gac acc ctc atg atc tcc cgg acc cct gag gtc aca tgc gtg gtg gtg      720
Asp Thr Leu Met Ile Ser Arg Thr Pro Glu Val Thr Cys Val Val Val
225                 230                 235                 240 gac gtg agc cac gaa gac cct gag gtc aag ttc aac tgg tac gtg gac      768
Asp Val Ser His Glu Asp Pro Glu Val Lys Phe Asn Trp Tyr Val Asp
                245                 250                 255 ggc gtg gag gtg cat aat gcc aag aca aag ccg cgg gag gag cag tac      816
Gly Val Glu Val His Asn Ala Lys Thr Lys Pro Arg Glu Glu Gln Tyr
            260                 265                 270 aac agc acg tac cgt gtg gtc agc gtc ctc acc gtc ctg cac cag gac      864
Asn Ser Thr Tyr Arg Val Val Ser Val Leu Thr Val Leu His Gln Asp
        275                 280                 285 tgg ctg aat ggc aag gag tac aag tgc aag gtc tcc aac aaa gcc ctc      912
Trp Leu Asn Gly Lys Glu Tyr Lys Cys Lys Val Ser Asn Lys Ala Leu
    290                 295                 300 cca gcc ccc atc gag aaa acc atc tcc aaa gcc aaa ggg cag ccc cga      960
Pro Ala Pro Ile Glu Lys Thr Ile Ser Lys Ala Lys Gly Gln Pro Arg
305                 310                 315                 320 gaa cca cag gtg tac acc ctg ccc cca tcc cgg gat gag ctg acc aag     1008
Glu Pro Gln Val Tyr Thr Leu Pro Pro Ser Arg Asp Glu Leu Thr Lys
                325                 330                 335 aac cag gtc agc ctg acc tgc ctg gtc aaa ggc ttc tat ccc agc gac     1056
Asn Gln Val Ser Leu Thr Cys Leu Val Lys Gly Phe Tyr Pro Ser Asp
            340                 345                 350 atc gcc gtg gag tgg gag agc aat ggg cag ccg gag aac aac tac aag     1104
Ile Ala Val Glu Trp Glu Ser Asn Gly Gln Pro Glu Asn Asn Tyr Lys
        355                 360                 365 acc acg cct ccc gtg ctg gac tcc gac ggc tcc ttc ttc ctc tac agc     1152
Thr Thr Pro Pro Val Leu Asp Ser Asp Gly Ser Phe Phe Leu Tyr Ser
    370                 375                 380 aag ctc acc gtg gac aag agc agg tgg cag cag ggg aac gtc ttc tca     1200
Lys Leu Thr Val Asp Lys Ser Arg Trp Gln Gln Gly Asn Val Phe Ser
385                 390                 395                 400 tgc tcc gtg atg cat gag gct ctg cac aac cac tac acg cag aag agc     1248
Cys Ser Val Met His Glu Ala Leu His Asn His Tyr Thr Gln Lys Ser
                405                 410                 415 ctc tcc ctg tct ccg ggt aaa taa                                     1272
Leu Ser Leu Ser Pro Gly Lys
            420

<210> SEQ ID NO 37
<211> LENGTH: 423
<212> TYPE: PRT
<213> ORGANISM: Artificial sequence
<220> FEATURE:
<223> OTHER INFORMATION: Synthetic Construct

<400> SEQUENCE: 37

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30
```

-continued

```
Trp Ser Ala Asp Leu Asp Lys Cys Met Asp Cys Ala Ser Cys Arg Ala
             35                  40                  45

Arg Pro His Ser Asp Phe Cys Leu Gly Cys Ala Ala Ala Pro Pro Ala
     50                  55                  60

Ala Pro Gly Thr Ala Pro Cys Ser Arg Gly Ser Ser Trp Ser Ala Asp
 65                  70                  75                  80

Leu Asp Lys Cys Met Asp Cys Ala Ser Cys Arg Ala Arg Pro His Ser
                 85                  90                  95

Asp Phe Cys Leu Gly Cys Ala Ala Ala Pro Ala Ala Pro Gly Thr
             100                 105                 110

Ala Pro Cys Ser Arg Gly Ser Ser Trp Ser Ala Asp Leu Asp Lys Cys
         115                 120                 125

Met Asp Cys Ala Ser Cys Arg Ala Arg Pro His Ser Asp Phe Cys Leu
     130                 135                 140

Gly Cys Ala Ala Ala Pro Pro Ala Ala Pro Gly Thr Ala Pro Cys Ser
145                 150                 155                 160

Arg Gly Ser Ser Trp Ser Ala Asp Leu Asp Lys Cys Met Asp Cys Ala
                 165                 170                 175

Ser Cys Arg Ala Arg Pro His Ser Asp Phe Cys Leu Gly Cys Ala Ala
             180                 185                 190

Ala Pro Pro Ala Asp Lys Thr His Thr Cys Pro Pro Cys Pro Ala Pro
         195                 200                 205

Glu Leu Leu Gly Gly Pro Ser Val Phe Leu Phe Pro Pro Lys Pro Lys
     210                 215                 220

Asp Thr Leu Met Ile Ser Arg Thr Pro Glu Val Thr Cys Val Val Val
225                 230                 235                 240

Asp Val Ser His Glu Asp Pro Glu Val Lys Phe Asn Trp Tyr Val Asp
                 245                 250                 255

Gly Val Glu Val His Asn Ala Lys Thr Lys Pro Arg Glu Glu Gln Tyr
             260                 265                 270

Asn Ser Thr Tyr Arg Val Val Ser Val Leu Thr Val Leu His Gln Asp
         275                 280                 285

Trp Leu Asn Gly Lys Glu Tyr Lys Cys Lys Val Ser Asn Lys Ala Leu
     290                 295                 300

Pro Ala Pro Ile Glu Lys Thr Ile Ser Lys Ala Lys Gly Gln Pro Arg
305                 310                 315                 320

Glu Pro Gln Val Tyr Thr Leu Pro Pro Ser Arg Asp Glu Leu Thr Lys
                 325                 330                 335

Asn Gln Val Ser Leu Thr Cys Leu Val Lys Gly Phe Tyr Pro Ser Asp
             340                 345                 350

Ile Ala Val Glu Trp Glu Ser Asn Gly Gln Pro Glu Asn Asn Tyr Lys
         355                 360                 365

Thr Thr Pro Pro Val Leu Asp Ser Asp Gly Ser Phe Phe Leu Tyr Ser
     370                 375                 380

Lys Leu Thr Val Asp Lys Ser Arg Trp Gln Gln Gly Asn Val Phe Ser
385                 390                 395                 400

Cys Ser Val Met His Glu Ala Leu His Asn His Tyr Thr Gln Lys Ser
                 405                 410                 415

Leu Ser Leu Ser Pro Gly Lys
             420

<210> SEQ ID NO 38
<211> LENGTH: 1404
```

```
<212> TYPE: DNA
<213> ORGANISM: Artificial sequence
<220> FEATURE:
<223> OTHER INFORMATION: TWEAKR 43quint-3
<220> FEATURE:
<221> NAME/KEY: CDS
<222> LOCATION: (1)..(1404)

<400> SEQUENCE: 38 atg gag aca gac aca ctc ctg cta tgg gta ctg ctg ctc tgg gtt cca        48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc        96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg       144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cct cct gcc       192
Arg Pro His Ser Asp Phe Cys Leu Gly Cys Ala Ala Ala Pro Pro Ala
    50                  55                  60 gca cca ggc acc gcc ccc tgc tcc cgc ggc agc tcc tgg agc gcg gac       240
Ala Pro Gly Thr Ala Pro Cys Ser Arg Gly Ser Ser Trp Ser Ala Asp
65                  70                  75                  80 ctg gac aag tgc atg gac tgc gcg tct tgc agg gcg cga ccg cac agc       288
Leu Asp Lys Cys Met Asp Cys Ala Ser Cys Arg Ala Arg Pro His Ser
                85                  90                  95 gac ttc tgc ctg ggc tgc gct gca gca cct cct gcc gca cca ggc acc       336
Asp Phe Cys Leu Gly Cys Ala Ala Ala Pro Pro Ala Ala Pro Gly Thr
            100                 105                 110 gcc ccc tgc tcc cgc ggc agc tcc tgg agc gcg gac ctg gac aag tgc       384
Ala Pro Cys Ser Arg Gly Ser Ser Trp Ser Ala Asp Leu Asp Lys Cys
        115                 120                 125 atg gac tgc gcg tct tgc agg gcg cga ccg cac agc gac ttc tgc ctg       432
Met Asp Cys Ala Ser Cys Arg Ala Arg Pro His Ser Asp Phe Cys Leu
    130                 135                 140 ggc tgc gct gca gca cct cct gcc gca cca ggc acc gcc ccc tgc tcc       480
Gly Cys Ala Ala Ala Pro Pro Ala Ala Pro Gly Thr Ala Pro Cys Ser
145                 150                 155                 160 cgc ggc agc tcc tgg agc gcg gac ctg gac aag tgc atg gac tgc gcg       528
Arg Gly Ser Ser Trp Ser Ala Asp Leu Asp Lys Cys Met Asp Cys Ala
                165                 170                 175 tct tgc agg gcg cga ccg cac agc gac ttc tgc ctg ggc tgc gct gca       576
Ser Cys Arg Ala Arg Pro His Ser Asp Phe Cys Leu Gly Cys Ala Ala
            180                 185                 190 gca cct cct gcc gca cca ggc acc gcc ccc tgc tcc cgc ggc agc tcc       624
Ala Pro Pro Ala Ala Pro Gly Thr Ala Pro Cys Ser Arg Gly Ser Ser
        195                 200                 205 tgg agc gcg gac ctg gac aag tgc atg gac tgc gcg tct tgc agg gcg       672
Trp Ser Ala Asp Leu Asp Lys Cys Met Asp Cys Ala Ser Cys Arg Ala
    210                 215                 220 cga ccg cac agc gac ttc tgc ctg ggc tgc gct gca gca cct cct gcc       720
Arg Pro His Ser Asp Phe Cys Leu Gly Cys Ala Ala Ala Pro Pro Ala
225                 230                 235                 240 gac aaa act cac aca tgt cca ccg tgc cca gca cct gaa ctc ctg ggg       768
Asp Lys Thr His Thr Cys Pro Pro Cys Pro Ala Pro Glu Leu Leu Gly
                245                 250                 255 gga ccg tca gtt ttc ctc ttc ccc cca aaa ccc aag gac acc ctc atg       816
Gly Pro Ser Val Phe Leu Phe Pro Pro Lys Pro Lys Asp Thr Leu Met
            260                 265                 270 atc tcc cgg acc cct gag gtc aca tgc gtg gtg gtg gac gtg agc cac       864
```

```
Ile Ser Arg Thr Pro Glu Val Thr Cys Val Val Val Asp Val Ser His
        275                 280                 285 gaa gac cct gag gtc aag ttc aac tgg tac gtg gac ggc gtg gag gtg     912
Glu Asp Pro Glu Val Lys Phe Asn Trp Tyr Val Asp Gly Val Glu Val
        290                 295                 300 cat aat gcc aag aca aag ccg cgg gag gag cag tac aac agc acg tac     960
His Asn Ala Lys Thr Lys Pro Arg Glu Glu Gln Tyr Asn Ser Thr Tyr
305                 310                 315                 320 cgt gtg gtc agc gtc ctc acc gtc ctg cac cag gac tgg ctg aat ggc    1008
Arg Val Val Ser Val Leu Thr Val Leu His Gln Asp Trp Leu Asn Gly
                325                 330                 335 aag gag tac aag tgc aag gtc tcc aac aaa gcc ctc cca gcc ccc atc    1056
Lys Glu Tyr Lys Cys Lys Val Ser Asn Lys Ala Leu Pro Ala Pro Ile
340                 345                 350 gag aaa acc atc tcc aaa gcc aaa ggg cag ccc cga gaa cca cag gtg    1104
Glu Lys Thr Ile Ser Lys Ala Lys Gly Gln Pro Arg Glu Pro Gln Val
        355                 360                 365 tac acc ctg ccc cca tcc cgg gat gag ctg acc aag aac cag gtc agc    1152
Tyr Thr Leu Pro Pro Ser Arg Asp Glu Leu Thr Lys Asn Gln Val Ser
        370                 375                 380 ctg acc tgc ctg gtc aaa ggc ttc tat ccc agc gac atc gcc gtg gag    1200
Leu Thr Cys Leu Val Lys Gly Phe Tyr Pro Ser Asp Ile Ala Val Glu
385                 390                 395                 400 tgg gag agc aat ggg cag ccg gag aac aac tac aag acc acg cct ccc    1248
Trp Glu Ser Asn Gly Gln Pro Glu Asn Asn Tyr Lys Thr Thr Pro Pro
                405                 410                 415 gtg ctg gac tcc gac ggc tcc ttc ttc ctc tac agc aag ctc acc gtg    1296
Val Leu Asp Ser Asp Gly Ser Phe Phe Leu Tyr Ser Lys Leu Thr Val
                420                 425                 430 gac aag agc agg tgg cag cag ggg aac gtc ttc tca tgc tcc gtg atg    1344
Asp Lys Ser Arg Trp Gln Gln Gly Asn Val Phe Ser Cys Ser Val Met
                435                 440                 445 cat gag gct ctg cac aac cac tac acg cag aag agc ctc tcc ctg tct    1392
His Glu Ala Leu His Asn His Tyr Thr Gln Lys Ser Leu Ser Leu Ser
        450                 455                 460 ccg ggt aaa taa                                                    1404
Pro Gly Lys
465
```

<210> SEQ ID NO 39
<211> LENGTH: 467
<212> TYPE: PRT
<213> ORGANISM: Artificial sequence
<220> FEATURE:
<223> OTHER INFORMATION: Synthetic Construct

<400> SEQUENCE: 39

```
Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
                20                  25                  30

Trp Ser Ala Asp Leu Asp Lys Cys Met Asp Cys Ala Ser Cys Arg Ala
            35                  40                  45

Arg Pro His Ser Asp Phe Cys Leu Gly Cys Ala Ala Ala Pro Pro Ala
        50                  55                  60

Ala Pro Gly Thr Ala Pro Cys Ser Arg Gly Ser Ser Trp Ser Ala Asp
65                  70                  75                  80

Leu Asp Lys Cys Met Asp Cys Ala Ser Cys Arg Ala Arg Pro His Ser
                85                  90                  95
```

```
Asp Phe Cys Leu Gly Cys Ala Ala Ala Pro Ala Ala Pro Gly Thr
                100                 105                 110
Ala Pro Cys Ser Arg Gly Ser Ser Trp Ser Ala Asp Leu Asp Lys Cys
        115                 120                 125
Met Asp Cys Ala Ser Cys Arg Ala Arg Pro His Ser Asp Phe Cys Leu
    130                 135                 140
Gly Cys Ala Ala Ala Pro Pro Ala Ala Pro Gly Thr Ala Pro Cys Ser
145                 150                 155                 160
Arg Gly Ser Ser Trp Ser Ala Asp Leu Asp Lys Cys Met Asp Cys Ala
                165                 170                 175
Ser Cys Arg Ala Arg Pro His Ser Asp Phe Cys Leu Gly Cys Ala Ala
            180                 185                 190
Ala Pro Pro Ala Ala Pro Gly Thr Ala Pro Cys Ser Arg Gly Ser Ser
        195                 200                 205
Trp Ser Ala Asp Leu Asp Lys Cys Met Asp Cys Ala Ser Cys Arg Ala
    210                 215                 220
Arg Pro His Ser Asp Phe Cys Leu Gly Cys Ala Ala Ala Pro Pro Ala
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
        275                 280                 285
Glu Asp Pro Glu Val Lys Phe Asn Trp Tyr Val Asp Gly Val Glu Val
    290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
        355                 360                 365
Tyr Thr Leu Pro Pro Ser Arg Asp Glu Leu Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
        435                 440                 445
His Glu Ala Leu His Asn His Tyr Thr Gln Lys Ser Leu Ser Leu Ser
    450                 455                 460
Pro Gly Lys
465

<210> SEQ ID NO 40
<211> LENGTH: 1536
<212> TYPE: DNA
<213> ORGANISM: Artificial sequence
<220> FEATURE:
<223> OTHER INFORMATION: TWEAKR 43hex-1
```

```
<220> FEATURE:
<221> NAME/KEY: CDS
<222> LOCATION: (1)..(1536)

<400> SEQUENCE: 40 atg gag aca gac aca ctc ctg cta tgg gta ctg ctg ctc tgg gtt cca     48
Met Glu Thr Asp Thr Leu Leu Leu Trp Val Leu Leu Leu Trp Val Pro
1               5                   10                  15 ggt tcc acc ggt gca cca ggc acc gcc ccc tgc tcc cgc ggc agc tcc     96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg    144
Trp Ser Ala Asp Leu Asp Lys Cys Met Asp Cys Ala Ser Cys Arg Ala
        35                  40                  45 cga ccg cac agc gac ttc tgc ctg ggc tgc gct gca gca cct cct gcc    192
Arg Pro His Ser Asp Phe Cys Leu Gly Cys Ala Ala Ala Pro Pro Ala
    50                  55                  60 gca cca ggc acc gcc ccc tgc tcc cgc ggc agc tcc tgg agc gcg gac    240
Ala Pro Gly Thr Ala Pro Cys Ser Arg Gly Ser Ser Trp Ser Ala Asp
65                  70                  75                  80 ctg gac aag tgc atg gac tgc gcg tct tgc agg gcg cga ccg cac agc    288
Leu Asp Lys Cys Met Asp Cys Ala Ser Cys Arg Ala Arg Pro His Ser
                85                  90                  95 gac ttc tgc ctg ggc tgc gct gca gca cct cct gcc gca cca ggc acc    336
Asp Phe Cys Leu Gly Cys Ala Ala Ala Pro Pro Ala Ala Pro Gly Thr
            100                 105                 110 gcc ccc tgc tcc cgc ggc agc tcc tgg agc gcg gac ctg gac aag tgc    384
Ala Pro Cys Ser Arg Gly Ser Ser Trp Ser Ala Asp Leu Asp Lys Cys
        115                 120                 125 atg gac tgc gcg tct tgc agg gcg cga ccg cac agc gac ttc tgc ctg    432
Met Asp Cys Ala Ser Cys Arg Ala Arg Pro His Ser Asp Phe Cys Leu
    130                 135                 140 ggc tgc gct gca gca cct cct gcc gca cca ggc acc gcc ccc tgc tcc    480
Gly Cys Ala Ala Ala Pro Pro Ala Ala Pro Gly Thr Ala Pro Cys Ser
145                 150                 155                 160 cgc ggc agc tcc tgg agc gcg gac ctg gac aag tgc atg gac tgc gcg    528
Arg Gly Ser Ser Trp Ser Ala Asp Leu Asp Lys Cys Met Asp Cys Ala
                165                 170                 175 tct tgc agg gcg cga ccg cac agc gac ttc tgc ctg ggc tgc gct gca    576
Ser Cys Arg Ala Arg Pro His Ser Asp Phe Cys Leu Gly Cys Ala Ala
            180                 185                 190 gca cct cct gcc gca cca ggc acc gcc ccc tgc tcc cgc ggc agc tcc    624
Ala Pro Pro Ala Ala Pro Gly Thr Ala Pro Cys Ser Arg Gly Ser Ser
        195                 200                 205 tgg agc gcg gac ctg gac aag tgc atg gac tgc gcg tct tgc agg gcg    672
Trp Ser Ala Asp Leu Asp Lys Cys Met Asp Cys Ala Ser Cys Arg Ala
    210                 215                 220 cga ccg cac agc gac ttc tgc ctg ggc tgc gct gca gca cct cct gcc    720
Arg Pro His Ser Asp Phe Cys Leu Gly Cys Ala Ala Ala Pro Pro Ala
225                 230                 235                 240 gca cca ggc acc gcc ccc tgc tcc cgc ggc agc tcc tgg agc gcg gac    768
Ala Pro Gly Thr Ala Pro Cys Ser Arg Gly Ser Ser Trp Ser Ala Asp
                245                 250                 255 ctg gac aag tgc atg gac tgc gcg tct tgc agg gcg cga ccg cac agc    816
Leu Asp Lys Cys Met Asp Cys Ala Ser Cys Arg Ala Arg Pro His Ser
            260                 265                 270 gac ttc tgc ctg ggc tgc gct gca gca cct cct gcc gac aaa act cac    864
Asp Phe Cys Leu Gly Cys Ala Ala Ala Pro Pro Ala Asp Lys Thr His
        275                 280                 285 aca tgt cca ccg tgc cca gca cct gaa ctc ctg ggg gga ccg tca gtt    912
```

```
              Thr Cys Pro Cys Pro Ala Pro Glu Leu Leu Gly Pro Ser Val
                  290                 295                 300 ttc ctc ttc ccc cca aaa ccc aag gac acc ctc atg atc tcc cgg acc      960
Phe Leu Phe Pro Pro Lys Pro Lys Asp Thr Leu Met Ile Ser Arg Thr
305                 310                 315                 320 cct gag gtc aca tgc gtg gtg gtg gac gtg agc cac gaa gac cct gag     1008
Pro Glu Val Thr Cys Val Val Val Asp Val Ser His Glu Asp Pro Glu
                325                 330                 335 gtc aag ttc aac tgg tac gtg gac ggc gtg gag gtg cat aat gcc aag     1056
Val Lys Phe Asn Trp Tyr Val Asp Gly Val Glu Val His Asn Ala Lys
            340                 345                 350 aca aag ccg cgg gag gag cag tac aac agc acg tac cgt gtg gtc agc     1104
Thr Lys Pro Arg Glu Glu Gln Tyr Asn Ser Thr Tyr Arg Val Val Ser
        355                 360                 365 gtc ctc acc gtc ctg cac cag gac tgg ctg aat ggc aag gag tac aag     1152
Val Leu Thr Val Leu His Gln Asp Trp Leu Asn Gly Lys Glu Tyr Lys
    370                 375                 380 tgc aag gtc tcc aac aaa gcc ctc cca gcc ccc atc gag aaa acc atc     1200
Cys Lys Val Ser Asn Lys Ala Leu Pro Ala Pro Ile Glu Lys Thr Ile
385                 390                 395                 400 tcc aaa gcc aaa ggg cag ccc cga gaa cca cag gtg tac acc ctg ccc     1248
Ser Lys Ala Lys Gly Gln Pro Arg Glu Pro Gln Val Tyr Thr Leu Pro
                405                 410                 415 cca tcc cgg gat gag ctg acc aag aac cag gtc agc ctg acc tgc ctg     1296
Pro Ser Arg Asp Glu Leu Thr Lys Asn Gln Val Ser Leu Thr Cys Leu
                420                 425                 430 gtc aaa ggc ttc tat ccc agc gac atc gcc gtg gag tgg gag agc aat     1344
Val Lys Gly Phe Tyr Pro Ser Asp Ile Ala Val Glu Trp Glu Ser Asn
            435                 440                 445 ggg cag ccg gag aac aac tac aag acc acg cct ccc gtg ctg gac tcc     1392
Gly Gln Pro Glu Asn Asn Tyr Lys Thr Thr Pro Pro Val Leu Asp Ser
        450                 455                 460 gac ggc tcc ttc ttc ctc tac agc aag ctc acc gtg gac aag agc agg     1440
Asp Gly Ser Phe Phe Leu Tyr Ser Lys Leu Thr Val Asp Lys Ser Arg
465                 470                 475                 480 tgg cag cag ggg aac gtc ttc tca tgc tcc gtg atg cat gag gct ctg     1488
Trp Gln Gln Gly Asn Val Phe Ser Cys Ser Val Met His Glu Ala Leu
                485                 490                 495 cac aac cac tac acg cag aag agc ctc tcc ctg tct ccg ggt aaa taa    1536
His Asn His Tyr Thr Gln Lys Ser Leu Ser Leu Ser Pro Gly Lys
                500                 505                 510

<210> SEQ ID NO 41
<211> LENGTH: 511
<212> TYPE: PRT
<213> ORGANISM: Artificial sequence
<220> FEATURE:
<223> OTHER INFORMATION: Synthetic Construct

<400> SEQUENCE: 41

Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
                20                  25                  30

Trp Ser Ala Asp Leu Asp Lys Cys Met Asp Cys Ala Ser Cys Arg Ala
            35                  40                  45

Arg Pro His Ser Asp Phe Cys Leu Gly Cys Ala Ala Ala Pro Pro Ala
        50                  55                  60

Ala Pro Gly Thr Ala Pro Cys Ser Arg Gly Ser Ser Trp Ser Ala Asp
65                  70                  75                  80
```

-continued

```
Leu Asp Lys Cys Met Asp Cys Ala Ser Cys Arg Ala Arg Pro His Ser
                85                  90                  95
Asp Phe Cys Leu Gly Cys Ala Ala Ala Pro Ala Ala Pro Gly Thr
            100                 105                 110
Ala Pro Cys Ser Arg Gly Ser Ser Trp Ser Ala Asp Leu Asp Lys Cys
        115                 120                 125
Met Asp Cys Ala Ser Cys Arg Ala Arg Pro His Ser Asp Phe Cys Leu
    130                 135                 140
Gly Cys Ala Ala Ala Pro Pro Ala Ala Pro Gly Thr Ala Pro Cys Ser
145                 150                 155                 160
Arg Gly Ser Ser Trp Ser Ala Asp Leu Asp Lys Cys Met Asp Cys Ala
                165                 170                 175
Ser Cys Arg Ala Arg Pro His Ser Asp Phe Cys Leu Gly Cys Ala Ala
            180                 185                 190
Ala Pro Pro Ala Pro Gly Thr Ala Pro Cys Ser Arg Gly Ser Ser
        195                 200                 205
Trp Ser Ala Asp Leu Asp Lys Cys Met Asp Cys Ala Ser Cys Arg Ala
    210                 215                 220
Arg Pro His Ser Asp Phe Cys Leu Gly Cys Ala Ala Ala Pro Pro Ala
225                 230                 235                 240
Ala Pro Gly Thr Ala Pro Cys Ser Arg Gly Ser Ser Trp Ser Ala Asp
                245                 250                 255
Leu Asp Lys Cys Met Asp Cys Ala Ser Cys Arg Ala Arg Pro His Ser
            260                 265                 270
Asp Phe Cys Leu Gly Cys Ala Ala Ala Pro Pro Ala Asp Lys Thr His
        275                 280                 285
Thr Cys Pro Pro Cys Pro Ala Pro Glu Leu Leu Gly Pro Ser Val
    290                 295                 300
Phe Leu Phe Pro Pro Lys Pro Lys Asp Thr Leu Met Ile Ser Arg Thr
305                 310                 315                 320
Pro Glu Val Thr Cys Val Val Asp Val Ser His Glu Asp Pro Glu
                325                 330                 335
Val Lys Phe Asn Trp Tyr Val Asp Gly Val Glu Val His Asn Ala Lys
            340                 345                 350
Thr Lys Pro Arg Glu Glu Gln Tyr Asn Ser Thr Tyr Arg Val Val Ser
        355                 360                 365
Val Leu Thr Val Leu His Gln Asp Trp Leu Asn Gly Lys Glu Tyr Lys
    370                 375                 380
Cys Lys Val Ser Asn Lys Ala Leu Pro Ala Pro Ile Glu Lys Thr Ile
385                 390                 395                 400
Ser Lys Ala Lys Gly Gln Pro Arg Glu Pro Gln Val Tyr Thr Leu Pro
                405                 410                 415
Pro Ser Arg Asp Glu Leu Thr Lys Asn Gln Val Ser Leu Thr Cys Leu
            420                 425                 430
Val Lys Gly Phe Tyr Pro Ser Asp Ile Ala Val Glu Trp Glu Ser Asn
        435                 440                 445
Gly Gln Pro Glu Asn Asn Tyr Lys Thr Thr Pro Pro Val Leu Asp Ser
    450                 455                 460
Asp Gly Ser Phe Phe Leu Tyr Ser Lys Leu Thr Val Asp Lys Ser Arg
465                 470                 475                 480
Trp Gln Gln Gly Asn Val Phe Ser Cys Ser Val Met His Glu Ala Leu
                485                 490                 495
```

```
His Asn His Tyr Thr Gln Lys Ser Leu Ser Leu Ser Pro Gly Lys
                500                 505                 510

<210> SEQ ID NO 42
<211> LENGTH: 1668
<212> TYPE: DNA
<213> ORGANISM: Artificial sequence
<220> FEATURE:
<223> OTHER INFORMATION: TWEAKR 43-sept-1
<220> FEATURE:
<221> NAME/KEY: CDS
<222> LOCATION: (1)..(1668)

<400> SEQUENCE: 42 atg gag aca gac aca ctc ctg cta tgg gta ctg ctc tgg gtt cca        48
Met Glu Thr Asp Thr Leu Leu Leu Trp Val Leu Leu Trp Val Pro
1               5                   10                  15 ggt tcc acc ggt gca cca ggc acc gcc ccc tgc tcc cgc ggc agc tcc    96
Gly Ser Thr Gly Ala Pro Gly Thr Ala Pro Cys Ser Arg Gly Ser Ser
            20                  25                  30 tgg agc gcg gac ctg gac aag tgc atg gac tgc gcg tct tgc agg gcg   144
Trp Ser Ala Asp Leu Asp Lys Cys Met Asp Cys Ala Ser Cys Arg Ala
        35                  40                  45 cga ccg cac agc gac ttc tgc ctg ggc tgc gct gca cct cct gcc       192
Arg Pro His Ser Asp Phe Cys Leu Gly Cys Ala Ala Pro Pro Ala
    50                  55                  60 gca cca ggc acc gcc ccc tgc tcc cgc ggc agc tcc tgg agc gcg gac   240
Ala Pro Gly Thr Ala Pro Cys Ser Arg Gly Ser Ser Trp Ser Ala Asp
65                  70                  75                  80 ctg gac aag tgc atg gac tgc gcg tct tgc agg gcg cga ccg cac agc   288
Leu Asp Lys Cys Met Asp Cys Ala Ser Cys Arg Ala Arg Pro His Ser
                85                  90                  95 gac ttc tgc ctg ggc tgc gct gca gca cct cct gcc gca cca ggc acc   336
Asp Phe Cys Leu Gly Cys Ala Ala Ala Pro Pro Ala Ala Pro Gly Thr
            100                 105                 110 gcc ccc tgc tcc cgc ggc agc tcc tgg agc gcg gac ctg gac aag tgc   384
Ala Pro Cys Ser Arg Gly Ser Ser Trp Ser Ala Asp Leu Asp Lys Cys
        115                 120                 125 atg gac tgc gcg tct tgc agg gcg cga ccg cac agc gac ttc tgc ctg   432
Met Asp Cys Ala Ser Cys Arg Ala Arg Pro His Ser Asp Phe Cys Leu
    130                 135                 140 ggc tgc gct gca gca cct cct gcc gca cca ggc acc gcc ccc tgc tcc   480
Gly Cys Ala Ala Ala Pro Pro Ala Ala Pro Gly Thr Ala Pro Cys Ser
145                 150                 155                 160 cgc ggc agc tcc tgg agc gcg gac ctg gac aag tgc atg gac tgc gcg   528
Arg Gly Ser Ser Trp Ser Ala Asp Leu Asp Lys Cys Met Asp Cys Ala
                165                 170                 175 tct tgc agg gcg cga ccg cac agc gac ttc tgc ctg ggc tgc gct gca   576
Ser Cys Arg Ala Arg Pro His Ser Asp Phe Cys Leu Gly Cys Ala Ala
            180                 185                 190 gca cct cct gcc gca cca ggc acc gcc ccc tgc tcc cgc ggc agc tcc   624
Ala Pro Pro Ala Ala Pro Gly Thr Ala Pro Cys Ser Arg Gly Ser Ser
        195                 200                 205 tgg agc gcg gac ctg gac aag tgc atg gac tgc gcg tct tgc agg gcg   672
Trp Ser Ala Asp Leu Asp Lys Cys Met Asp Cys Ala Ser Cys Arg Ala
    210                 215                 220 cga ccg cac agc gac ttc tgc ctg ggc tgc gct gca gca cct cct gcc   720
Arg Pro His Ser Asp Phe Cys Leu Gly Cys Ala Ala Ala Pro Pro Ala
225                 230                 235                 240 gca cca ggc acc gcc ccc tgc tcc cgc ggc agc tcc tgg agc gcg gac   768
Ala Pro Gly Thr Ala Pro Cys Ser Arg Gly Ser Ser Trp Ser Ala Asp
                245                 250                 255
```

```
ctg gac aag tgc atg gac tgc gcg tct tgc agg gcg cga ccg cac agc      816
Leu Asp Lys Cys Met Asp Cys Ala Ser Cys Arg Ala Arg Pro His Ser
        260                 265                 270 gac ttc tgc ctg ggc tgc gct gca gca cct cct gcc gca cca ggc acc      864
Asp Phe Cys Leu Gly Cys Ala Ala Ala Pro Pro Ala Ala Pro Gly Thr
            275                 280                 285 gcc ccc tgc tcc cgc ggc agc tcc tgg agc gcg gac ctg gac aag tgc      912
Ala Pro Cys Ser Arg Gly Ser Ser Trp Ser Ala Asp Leu Asp Lys Cys
        290                 295                 300 atg gac tgc gcg tct tgc agg gcg cga ccg cac agc gac ttc tgc ctg      960
Met Asp Cys Ala Ser Cys Arg Ala Arg Pro His Ser Asp Phe Cys Leu
305                 310                 315                 320 ggc tgc gct gca gca cct cct gcc gac aaa act cac aca tgt cca ccg     1008
Gly Cys Ala Ala Ala Pro Pro Ala Asp Lys Thr His Thr Cys Pro Pro
                325                 330                 335 tgc cca gca cct gaa ctc ctg ggg gga ccg tca gtt ttc ctc ttc ccc     1056
Cys Pro Ala Pro Glu Leu Leu Gly Gly Pro Ser Val Phe Leu Phe Pro
            340                 345                 350 cca aaa ccc aag gac acc ctc atg atc tcc cgg acc cct gag gtc aca     1104
Pro Lys Pro Lys Asp Thr Leu Met Ile Ser Arg Thr Pro Glu Val Thr
        355                 360                 365 tgc gtg gtg gtg gac gtg agc cac gaa gac cct gag gtc aag ttc aac     1152
Cys Val Val Val Asp Val Ser His Glu Asp Pro Glu Val Lys Phe Asn
370                 375                 380 tgg tac gtg gac ggc gtg gag gtg cat aat gcc aag aca aag ccg cgg     1200
Trp Tyr Val Asp Gly Val Glu Val His Asn Ala Lys Thr Lys Pro Arg
385                 390                 395                 400 gag gag cag tac aac agc acg tac cgt gtg gtc agc gtc ctc acc gtc     1248
Glu Glu Gln Tyr Asn Ser Thr Tyr Arg Val Val Ser Val Leu Thr Val
                405                 410                 415 ctg cac cag gac tgg ctg aat ggc aag gag tac aag tgc aag gtc tcc     1296
Leu His Gln Asp Trp Leu Asn Gly Lys Glu Tyr Lys Cys Lys Val Ser
            420                 425                 430 aac aaa gcc ctc cca gcc ccc atc gag aaa acc atc tcc aaa gcc aaa     1344
Asn Lys Ala Leu Pro Ala Pro Ile Glu Lys Thr Ile Ser Lys Ala Lys
        435                 440                 445 ggg cag ccc cga gaa cca cag gtg tac acc ctg ccc cca tcc cgg gat     1392
Gly Gln Pro Arg Glu Pro Gln Val Tyr Thr Leu Pro Pro Ser Arg Asp
450                 455                 460 gag ctg acc aag aac cag gtc agc ctg acc tgc ctg gtc aaa ggc ttc     1440
Glu Leu Thr Lys Asn Gln Val Ser Leu Thr Cys Leu Val Lys Gly Phe
465                 470                 475                 480 tat ccc agc gac atc gcc gtg gag tgg gag agc aat ggg cag ccg gag     1488
Tyr Pro Ser Asp Ile Ala Val Glu Trp Glu Ser Asn Gly Gln Pro Glu
                485                 490                 495 aac aac tac aag acc acg cct ccc gtg ctg gac tcc gac ggc tcc ttc     1536
Asn Asn Tyr Lys Thr Thr Pro Pro Val Leu Asp Ser Asp Gly Ser Phe
            500                 505                 510 ttc ctc tac agc aag ctc acc gtg gac aag agc agg tgg cag cag ggg     1584
Phe Leu Tyr Ser Lys Leu Thr Val Asp Lys Ser Arg Trp Gln Gln Gly
        515                 520                 525 aac gtc ttc tca tgc tcc gtg atg cat gag gct ctg cac aac cac tac     1632
Asn Val Phe Ser Cys Ser Val Met His Glu Ala Leu His Asn His Tyr
530                 535                 540 acg cag aag agc ctc tcc ctg tct ccg ggt aaa taa                     1668
Thr Gln Lys Ser Leu Ser Leu Ser Pro Gly Lys
545                 550                 555
```

<210> SEQ ID NO 43

<211> LENGTH: 555
<212> TYPE: PRT
<213> ORGANISM: Artificial sequence
<220> FEATURE:
<223> OTHER INFORMATION: Synthetic Construct

<400> SEQUENCE: 43

```
Met Glu Thr Asp Thr Leu Leu Leu Trp Val Leu Leu Leu Trp Val Pro
1               5                   10                  15

Gly Ser Thr Gly Ala Pro Gly Thr Ala Pro Cys Ser Arg Gly Ser Ser
            20                  25                  30

Trp Ser Ala Asp Leu Asp Lys Cys Met Asp Cys Ala Ser Cys Arg Ala
        35                  40                  45

Arg Pro His Ser Asp Phe Cys Leu Gly Cys Ala Ala Pro Pro Ala
    50                  55                  60

Ala Pro Gly Thr Ala Pro Cys Ser Arg Gly Ser Ser Trp Ser Ala Asp
65                  70                  75                  80

Leu Asp Lys Cys Met Asp Cys Ala Ser Cys Arg Ala Arg Pro His Ser
                85                  90                  95

Asp Phe Cys Leu Gly Cys Ala Ala Ala Pro Pro Ala Ala Pro Gly Thr
            100                 105                 110

Ala Pro Cys Ser Arg Gly Ser Ser Trp Ser Ala Asp Leu Asp Lys Cys
        115                 120                 125

Met Asp Cys Ala Ser Cys Arg Ala Arg Pro His Ser Asp Phe Cys Leu
    130                 135                 140

Gly Cys Ala Ala Ala Pro Pro Ala Ala Pro Gly Thr Ala Pro Cys Ser
145                 150                 155                 160

Arg Gly Ser Ser Trp Ser Ala Asp Leu Asp Lys Cys Met Asp Cys Ala
                165                 170                 175

Ser Cys Arg Ala Arg Pro His Ser Asp Phe Cys Leu Gly Cys Ala Ala
            180                 185                 190

Ala Pro Pro Ala Ala Pro Gly Thr Ala Pro Cys Ser Arg Gly Ser Ser
        195                 200                 205

Trp Ser Ala Asp Leu Asp Lys Cys Met Asp Cys Ala Ser Cys Arg Ala
    210                 215                 220

Arg Pro His Ser Asp Phe Cys Leu Gly Cys Ala Ala Ala Pro Pro Ala
225                 230                 235                 240

Ala Pro Gly Thr Ala Pro Cys Ser Arg Gly Ser Ser Trp Ser Ala Asp
                245                 250                 255

Leu Asp Lys Cys Met Asp Cys Ala Ser Cys Arg Ala Arg Pro His Ser
            260                 265                 270

Asp Phe Cys Leu Gly Cys Ala Ala Ala Pro Pro Ala Ala Pro Gly Thr
        275                 280                 285

Ala Pro Cys Ser Arg Gly Ser Ser Trp Ser Ala Asp Leu Asp Lys Cys
    290                 295                 300

Met Asp Cys Ala Ser Cys Arg Ala Arg Pro His Ser Asp Phe Cys Leu
305                 310                 315                 320

Gly Cys Ala Ala Ala Pro Pro Ala Asp Lys Thr His Thr Cys Pro Pro
                325                 330                 335

Cys Pro Ala Pro Glu Leu Leu Gly Gly Pro Ser Val Phe Leu Phe Pro
            340                 345                 350

Pro Lys Pro Lys Asp Thr Leu Met Ile Ser Arg Thr Pro Glu Val Thr
        355                 360                 365

Cys Val Val Val Asp Val Ser His Glu Asp Pro Glu Val Lys Phe Asn
    370                 375                 380
```

```
Trp Tyr Val Asp Gly Val Glu Val His Asn Ala Lys Thr Lys Pro Arg
385                 390                 395                 400

Glu Glu Gln Tyr Asn Ser Thr Tyr Arg Val Val Ser Val Leu Thr Val
                405                 410                 415

Leu His Gln Asp Trp Leu Asn Gly Lys Glu Tyr Lys Cys Lys Val Ser
                420                 425                 430

Asn Lys Ala Leu Pro Ala Pro Ile Glu Lys Thr Ile Ser Lys Ala Lys
                435                 440                 445

Gly Gln Pro Arg Glu Pro Gln Val Tyr Thr Leu Pro Pro Ser Arg Asp
                450                 455                 460

Glu Leu Thr Lys Asn Gln Val Ser Leu Thr Cys Leu Val Lys Gly Phe
465                 470                 475                 480

Tyr Pro Ser Asp Ile Ala Val Glu Trp Glu Ser Asn Gly Gln Pro Glu
                485                 490                 495

Asn Asn Tyr Lys Thr Thr Pro Pro Val Leu Asp Ser Asp Gly Ser Phe
                500                 505                 510

Phe Leu Tyr Ser Lys Leu Thr Val Asp Lys Ser Arg Trp Gln Gln Gly
                515                 520                 525

Asn Val Phe Ser Cys Ser Val Met His Glu Ala Leu His Asn His Tyr
                530                 535                 540

Thr Gln Lys Ser Leu Ser Leu Ser Pro Gly Lys
545                 550                 555

<210> SEQ ID NO 44
<211> LENGTH: 282
<212> TYPE: PRT
<213> ORGANISM: Artificial Sequence
<220> FEATURE:
<223> OTHER INFORMATION: huTWEAKr 28-76:gly5:Fc

<400> SEQUENCE: 44

Met Glu Gln Ala Pro Gly Thr Ala Pro Cys Ser Arg Gly Ser Ser Trp
1               5                   10                  15

Ser Ala Asp Leu Asp Lys Cys Met Asp Cys Ala Ser Cys Arg Ala Arg
                20                  25                  30

Pro His Ser Asp Phe Cys Leu Gly Cys Ala Ala Ala Pro Pro Ala Pro
                35                  40                  45

Phe Arg Gly Gly Gly Gly Gly Asp Lys Thr His Thr Cys Pro Pro Cys
                50                  55                  60

Pro Ala Pro Glu Leu Leu Gly Gly Pro Ser Val Phe Leu Phe Pro Pro
65                  70                  75                  80

Lys Pro Lys Asp Thr Leu Met Ile Ser Arg Thr Pro Glu Val Thr Cys
                85                  90                  95

Val Val Val Asp Val Ser His Glu Asp Pro Glu Val Lys Phe Asn Trp
                100                 105                 110

Tyr Val Asp Gly Val Glu Val His Asn Ala Lys Thr Lys Pro Arg Glu
                115                 120                 125

Glu Gln Tyr Asn Ser Thr Tyr Arg Val Val Ser Val Leu Thr Val Leu
130                 135                 140

His Gln Asp Trp Leu Asn Gly Lys Glu Tyr Lys Cys Lys Val Ser Asn
145                 150                 155                 160

Lys Ala Leu Pro Ala Pro Ile Glu Lys Thr Ile Ser Lys Ala Lys Gly
                165                 170                 175

Gln Pro Arg Glu Pro Gln Val Tyr Thr Leu Pro Pro Ser Arg Asp Glu
                180                 185                 190
```

```
Leu Thr Lys Asn Gln Val Ser Leu Thr Cys Leu Val Lys Gly Phe Tyr
        195                 200                 205

Pro Ser Asp Ile Ala Val Glu Trp Glu Ser Asn Gly Gln Pro Glu Asn
        210                 215                 220

Asn Tyr Lys Thr Thr Pro Pro Val Leu Asp Ser Asp Gly Ser Phe Phe
225                 230                 235                 240

Leu Tyr Ser Lys Leu Thr Val Asp Lys Ser Arg Trp Gln Gln Gly Asn
                245                 250                 255

Val Phe Ser Cys Ser Val Met His Glu Ala Leu His Asn His Tyr Thr
                260                 265                 270

Gln Lys Ser Leu Ser Leu Ser Pro Gly Lys
        275                 280

<210> SEQ ID NO 45
<211> LENGTH: 5
<212> TYPE: PRT
<213> ORGANISM: Artificial sequence
<220> FEATURE:
<223> OTHER INFORMATION: linker

<400> SEQUENCE: 45

Gly Gly Gly Gly Gly
1               5
```

COMPOSITIONS AND METHODS RELATING TO MULTIMERIC AND OLIGOMERIC SOLUBLE FRAGMENTS OF THE TWEAK RECEPTOR

This application claims the benefit of U.S. provisional application 60/490,036, filed Jul. 24, 2003, the disclosure of which is incorporated by reference.

BACKGROUND OF THE INVENTION

Angiogenesis is a multi-step developmental process that results in the formation of new blood vessels off of existing vessels. This spatially and temporally regulated process involves loosening of matrix contacts and support cell interactions in the existing vessels by proteases, followed by coordinated movement, morphological alteration, and proliferation of the smooth muscle and endothelial cells of the existing vessel. The nascent cells then extend into the target tissue followed by cell-cell interactions in which the endothelial cells form tubes that the smooth muscle cells surround. In a coordinated fashion, extracellular matrix proteins of the vessel are secreted and peri-endothelial support cells are recruited to support and maintain structural integrity (see, e.g., Daniel et al., Ann. Rev. Physiol. 2000(62):649, 2000). Angiogenesis plays important roles in both normal and pathological physiology.

Under normal physiological conditions, angiogenesis is involved in fetal and embryonic development, wound healing, organ regeneration, and female reproductive remodeling processes including formation of the endometrium, corpus luteum, and placenta. Angiogenesis is stringently regulated under normal conditions, especially in adult animals, and perturbation of the regulatory controls can lead to pathological angiogenesis.

Pathological angiogenesis has been implicated in the manifestation and/or progression of inflammatory diseases, certain eye disorders, and cancer. In particular, several lines of evidence support the concept that angiogenesis is essential for the growth and persistence of solid tumors and their metastases (see, e.g., Folkman, N. Engl. J. Med. 285:1182, 1971; Folkman et al., Nature 339:58, 1989; Kim et al., Nature 362:841, 1993; Hori et al., Cancer Res., 51:6180, 1991). Angiogenesis inhibitors are therefore useful for the prevention (e.g., treatment of premalignant conditions), intervention (e.g., treatment of small tumors), and regression (e.g., treatment of large tumors) of cancers (see, e.g., Bergers et al., Science 284:808, 1999).

There is a need for additional compositions and methods of modulating angiogenesis for the prevention, abrogation, and mitigation of disease.

The TWEAK protein, which has also been called TREPA and Apo3L, is a member of the tumor necrosis factor (TNF) family and is expressed in a wide variety of human tissues (Chicheportiche et al., J. Biol. Chem., 272(51):32401, 1997; see also Wiley, PCT Publication No. WO 98/35061, 13 Aug. 1998). Like most TNF family members, TWEAK is a Type II membrane protein with an extracellular C-terminal domain. Although TWEAK was originally described as a weak inducer of apoptosis, this induction of cell death was later shown to be indirect (Schneider et al., Eur. J. Immunol. 29:1785, 1999).

Lynch et al. demonstrated that TWEAK directly induces endothelial cell proliferation and angiogenesis (J. Biol. Chem., 274(13):8455, 1999). Picomolar concentrations of recombinant soluble TWEAK induce proliferation in multiple endothelial cell lines and in aortic smooth muscle cells, and reduce the requirement for serum and growth factors in culture. Moreover, TWEAK induces a strong angiogenic response in a rat corneal pocket assay. Since TNF family members initiate biological responses by signaling through members of the TNF receptor family, there has been great interest in identifying and characterizing the TWEAK receptor.

Marsters et al. reported that TWEAK binds to and signals through a death-domain containing receptor known variously as DR3, Apo3, WSL-1, TRAMP, or LARD (Marsters et al., Current Biology 8(9):525, 1998). Schneider et al., however, showed that TWEAK binds to and signals in Kym-1 cells but that Kym-1 cells do not express the receptor DR3 (Schneider et al., Eur. J. Immunol. 29:1785, 1999). Wiley subsequently identified the primary TWEAK receptor and described certain soluble fragments and variants of it that antagonize the wild-type TWEAK receptor (PCT Pub. No. WO 01/45730).

Because TWEAK induces angiogenesis in vivo, there is a particular need for antagonists of the major functional TWEAK receptor. Such TWEAK receptor antagonists would be useful for reducing angiogenesis and treating human diseases, including cancers and inflammatory diseases.

SUMMARY OF THE INVENTION

The present invention is based upon the identification and characterization of polypeptides comprising multimeric soluble fragments of the major functional TWEAK receptor (TWEAKR) and an oligomerization domain. Surprisingly, these polypeptides have a higher binding affinity for TWEAK and/or are better competitors for TWEAK binding than would be expected from the TWEAK binding and competition properties of polypeptides comprising soluble monomeric TWEAKR fragments and an oligomerization domain or comprising soluble multimeric TWEAKR fragments without an oligomerization domain.

The invention provides, for example, compositions and methods for inhibiting angiogenesis in a mammal in need of such treatment comprising administering a therapeutically effective amount of a composition comprising a TWEAK receptor antagonist. The composition preferably comprises a pharmaceutically acceptable carrier and the mammal is preferably a human.

In one aspect, the present invention provides a polypeptide comprising a first soluble fragment of a TWEAK receptor, a second soluble fragment of a TWEAK receptor, and an oligomerization domain, wherein said polypeptide binds to TWEAK, and said first soluble fragment consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In one embodiment, said first soluble fragment consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment and said second soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment and said second soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment and said second soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a third soluble fragment of a TWEAK receptor. In another embodiment, said first soluble fragment, second soluble fragment, and third soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, and third soluble fragment each independently consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, and third soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a fourth soluble fragment of a TWEAK receptor. In another embodiment, said first soluble fragment, second soluble fragment, third soluble fragment, and fourth soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, and fourth soluble fragment each independently consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, and fourth soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a fifth soluble fragment of a TWEAK receptor. In another embodiment, said first soluble fragment, second soluble fragment, third soluble fragment, fourth soluble fragment, and fifth soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, and fifth soluble fragment each independently consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, and fifth soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a sixth soluble fragment of a TWEAK receptor. In another embodiment, said first soluble fragment, second soluble fragment, third soluble fragment, fourth soluble fragment, fifth soluble fragment, and sixth soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, fifth soluble fragment, and sixth soluble fragment each independently consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, fifth soluble fragment, and sixth soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a seventh soluble fragment of a TWEAK receptor. In another embodiment, said first soluble fragment, second soluble fragment, third soluble fragment, fourth soluble fragment, fifth soluble fragment, sixth soluble fragment, and seventh soluble fragment each independently consists of a sequence that is at least 90% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, fifth soluble fragment, sixth soluble fragment, and seventh soluble fragment each independently consists of a sequence that is at least 95% identical to a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7. In another embodiment, said first soluble fragment, second soluble fragment, third soluble fragment, fourth soluble fragment, fifth soluble fragment, sixth soluble fragment, and seventh soluble fragment each independently consists of a sequence selected from the group consisting of: residues 29 through 70 of the amino acid sequence of SEQ ID NO:7; residues 28 through 79 of the amino acid sequence of SEQ ID NO:7; residues 30 through 73 of the amino acid sequence of SEQ ID NO:7; and residues 30 through 70 of the amino acid sequence of SEQ ID NO:7.

In another embodiment, said polypeptide comprises a linker. In another embodiment, said linker joins said first soluble TWEAKR fragment and said second soluble TWEAKR fragment. In another embodiment, said linker joins said second soluble TWEAKR fragment and said oligomerization domain. In another embodiment, said polypeptide comprises a first linker and a second linker, wherein said first linker joins said first soluble TWEAKR fragment and said second soluble TWEAKR fragment, and said second linker joins said second soluble TWEAKR fragment and said oligomerization domain. In another embodiment, said linker comprises the amino acid sequence GGGGG (SEQ ID NO:45).

In another embodiment, said first soluble fragment and said second soluble fragment are joined together without an intervening polypeptide sequence. In another embodiment, said first soluble fragment and said oligomerization domain are joined together without an intervening polypeptide sequence. In another embodiment, said first soluble fragment, said second soluble fragment, and said oligomerization domain are joined together, without an intervening polypeptide sequence, in a linear and contiguous polypeptide.

In another embodiment, said oligomerization domain is N-terminal to said first soluble TWEAKR fragment and to said second soluble TWEAKR fragment. In another embodiment, said oligomerization domain is C-terminal to said first soluble TWEAKR fragment and to said second soluble TWEAKR fragment. In another embodiment, said oligomerization domain comprises a leucine zipper. In another embodiment, said oligomerization domain comprises a fragment of an antibody. In another embodiment, said fragment of an antibody comprises an Fc domain.

In another embodiment, said polypeptide comprises a sequence that is at least 90% identical to a sequence selected from the group consisting of: SEQ ID NO:9; SEQ ID NO:11; SEQ ID NO:13; SEQ ID NO:15; SEQ ID NO:17; SEQ ID NO:18; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; and SEQ ID NO:44. In another embodiment, said polypeptide comprises a sequence that is at least 95% identical to a sequence selected from the group consisting of: SEQ ID NO:9; SEQ ID NO:11; SEQ ID NO:13; SEQ ID NO:15; SEQ ID NO:17; SEQ ID NO:18; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; and SEQ ID NO:44. In another embodiment, said polypeptide comprises a sequence selected from the group consisting of: SEQ ID NO:9; SEQ ID NO:11; SEQ ID NO:13; SEQ ID NO:15; SEQ ID NO:17; SEQ ID NO:18; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; and SEQ ID NO:44.

In another aspect, the present invention provides a protein comprising a first said polypeptide and a second said polypeptide, wherein said first and second polypeptides are oligomerized to each other. In another embodiment, the amino acid sequence of said first polypeptide is identical to the amino acid sequence of said second polypeptide. In another embodiment, the amino acid sequence of said first polypeptide is not identical to the amino acid sequence of said second polypeptide.

In another aspect, the present invention provides a method of inhibiting a TWEAK receptor in a subject comprising administering to said subject said polypeptide.

In another aspect, the present invention provides a method of inhibiting angiogenesis in a subject comprising administering to said subject a therapeutically-effective amount of a composition comprising said polypeptide. In another embodiment, said composition further comprises a pharmaceutically acceptable carrier. In another embodiment, said subject is a mammal. In another embodiment, said mammal is a human. In another embodiment, said subject has a disease or condition mediated or exacerbated by angiogenesis. In another embodiment, said disease or condition is characterized by ocular neovascularization. In another embodiment, said disease or condition is a solid tumor. In another embodiment, said method further comprises treating said subject with radiation. In another embodiment, said method further comprises treating said subject with a second chemotherapeutic agent. In another embodiment, said second chemotherapeutic agent is selected from the group consisting of: an alkylating agent, an antimetabolite, a vinca alkaloid, a plant-derived chemotherapeutic, a nitrosourea, an antitumor antibiotic, an antitumor enzyme, a topoisomerase inhibitor, a platinum analog, an adrenocortical suppressant, a hormone, a hormone agonist, a hormone antagonist, an antibody, an immunotherapeutic, a blood cell factor, a radiotherapeutic, and a biological response modifier. In another embodiment, said second chemotherapeutic agent is selected from the group consisting of cisplatin, cyclophosphamide, mechlorethamine, melphalan, bleomycin, carboplatin, fluorouracil, 5-fluorodeoxyuridine, methotrexate, taxol, asparaginase, vincristine, vinblastine, a lymphokine, a cytokine, an interleukin, an interferon, alpha interferon, beta interferon, delta interferon, TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone. In another embodiment, said disease or condition is an inflammatory disease or condition. In another embodiment, said method further comprises treating said subject with a second therapeutic agent. In another embodiment, said second therapeutic agent inhibits a cytokine or a cytokine receptor that promotes inflammation. In another embodiment, said second therapeutic agent comprises a soluble fragment of said cytokine receptor, an antibody that binds said cytokine, or an antibody that binds said cytokine receptor. In another embodiment, said second therapeutic agent activates a receptor that inhibits inflammation. In another embodiment, said second therapeutic agent is selected from the group consisting of Flt3 ligand, CD40 ligand, interleukin-2, an interleukin-4 antagonist, an IL-13 antagonist, interleukin-12, 4-1BB ligand, an anti-4-1BB antibody, a TNF antagonist, a TNF receptor antagonist, TRAIL, a CD148 agonist, a VEGF antagonist, a VEGF receptor antagonist, an IgE antagonist, and a Tek antagonist.

In another aspect, the present invention provides a nucleic acid, or its complement, comprising a sequence that encodes said polypeptide. In another embodiment, said nucleic acid, or its complement, hybridizes under moderately stringent hybridization conditions to a second nucleic acid, and said second nucleic acid comprises a sequence selected from the group consisting of: SEQ ID NO:10; SEQ ID NO:12; SEQ ID NO:14; SEQ ID NO:16; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; SEQ ID NO:40; and SEQ ID NO:42. In another embodiment, said nucleic acid, or its complement, comprises a sequence that is at least 90% identical to a sequence selected from the group consisting of: SEQ ID NO:10; SEQ ID NO:12; SEQ ID NO:14; SEQ ID NO:16; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; SEQ ID NO:40; and SEQ ID NO:42. In another embodiment, said nucleic acid, or its complement, comprises a sequence that is at least 95% identical to a sequence selected from the group consisting of: SEQ ID NO:10; SEQ ID NO:12; SEQ ID NO:14; SEQ ID NO:16; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; SEQ ID NO:40; and SEQ ID NO:42. In another embodiment, said nucleic acid, or its complement, comprises a sequence selected from the group consisting of: SEQ ID NO:10; SEQ ID NO:12; SEQ ID NO:14; SEQ ID NO:16; SEQ ID NO:20; SEQ ID NO:22; SEQ ID NO:24; SEQ ID NO:26; SEQ ID NO:28; SEQ ID NO:30; SEQ ID NO:32; SEQ ID NO:34; SEQ ID NO:36; SEQ ID NO:38; SEQ ID NO:40; and SEQ ID NO:42. In another embodiment, said nucleic acid encodes a polypeptide sequence selected from the group consisting of: SEQ ID NO:9; SEQ ID NO:11; SEQ ID NO:13; SEQ ID NO:15; SEQ ID NO:17; SEQ ID NO:18; SEQ ID NO:19; SEQ ID NO:21; SEQ ID NO:23; SEQ ID NO:25; SEQ ID NO:27; SEQ ID NO:29; SEQ ID NO:31; SEQ ID NO:33; SEQ ID NO:35; SEQ ID NO:37; SEQ ID NO:39; SEQ ID NO:41; SEQ ID NO:43; and SEQ ID NO:44.

In another aspect, the present invention provides a vector comprising said nucleic acid. In another embodiment, said vector is an expression vector.

In another aspect, the present invention provides a host cell comprising said nucleic acid.

In another aspect, the present invention provides a method of producing a polypeptide comprising culturing said host cell under conditions promoting expression of said polypeptide.

BRIEF DESCRIPTION OF THE DRAWINGS

FIG. 1 shows a sequence alignment of the human and murine TWEAK receptor polypeptide sequences. The top sequence is the murine TWEAK receptor polypeptide (SEQ ID NO:5), and the bottom sequence is the human TWEAK receptor polypeptide (SEQ ID NO:4).

DETAILED DESCRIPTION OF THE INVENTION

Figure 2:
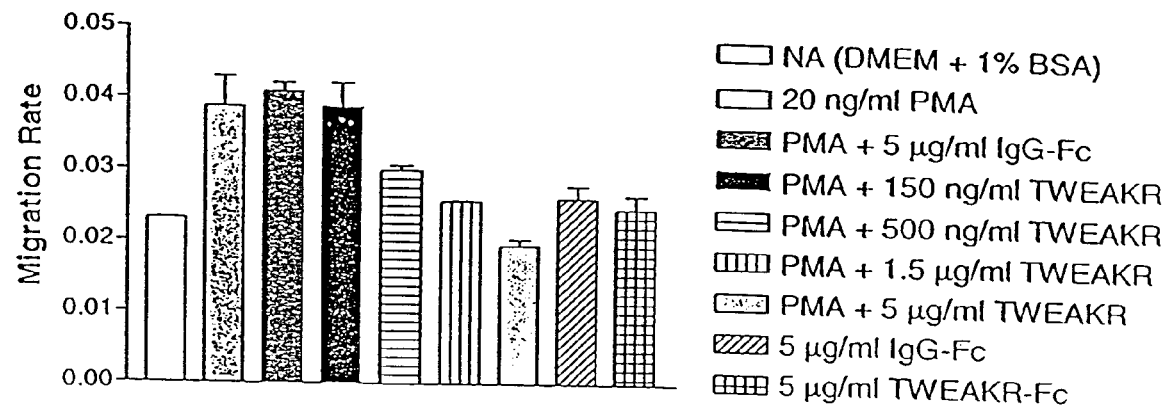
FIG. 2 shows the effect of TWEAKR-Fc on PMA-induced HRMEC wound closure.

The present invention provides compositions and methods relating to polypeptides comprising multimers of soluble fragments of TWEAKR and an oligomerization domain.

Abbreviations and Terminology Used in the Specification

"4-1BB" and "4-1BB ligand" (4-1BB-L) are polypeptides described, inter alia, in U.S. Pat. No. 5,674,704, including soluble forms thereof.

"bFGF" is basic fibroblast growth factor.

"BSA" is bovine serum albumin.

"CD40 ligand" (CD40L) is a polypeptide described, inter alia, in U.S. Pat. No. 5,716,805, including soluble forms thereof.

"CHO" is a Chinese hamster ovary cell line.

"DMEM" is Dulbecco's Modified eagle Medium, a commercially available cell culture medium.

"ELISA" is Enzyme-Linked Immunosorbent Assay.

"Flt3L" is Flt3 ligand, a polypeptide described, inter alia, in U.S. Pat. No. 5,554,512, including soluble forms thereof.

"HRMEC" are primary human renal microvascular endothelial cells.

"HUVEC" is a line of human umbilical vein endothelial cells.

"PBS" is phosphate buffered saline.

"PMA" is phorbol 12-myristate-13-acetate.

"RTKS" are receptor tyrosine kinases.

"Tek," which has also been called Tie2 and ork, is an RTK that is predominantly expressed in vascular endothelium. The molecular cloning of human Tek (ork) has been described by Ziegler, U.S. Pat. No. 5,447,860. "Tek antagonists" are described, inter alia, in Cerretti et al., PCT Publication No. WO 00/75323, 14 Dec. 2000.

"TNFR" is a tumor necrosis factor receptor, including soluble forms thereof. "TNFR/Fc" is a tumor necrosis factor receptor-Fc fusion polypeptide.

"TRAIL" is TNF-related apoptosis-inducing ligand, a type II transmembrane polypeptide in the TNF family described, inter alia, in U.S. Pat. No. 5,763,223, including soluble forms thereof.

"VEGF" is vascular endothelial growth factor, also known as VPF or vascular permeability factor.

Soluble TWEAK Receptor Polypeptides

Native human TWEAK receptor cDNA has the sequence SEQ ID NO:3, which encodes a 129 residue polypeptide (SEQ ID NO:4). Examination of the DNA sequence predicts a polypeptide having an approximately 78 amino acid extracellular domain (residues 1-78 of SEQ ID NO:4, including the signal peptide), an approximately 23 amino acid transmembrane domain (residues 79-101 of SEQ ID NO:4), and an approximately 28 amino acid intracellular domain (residues 102-129 of SEQ ID NO:4). The TWEAK receptor sequence has also been reported by Kato et al., PCT Publication No. WO 98/55508, 10 Dec. 1998 and by Incyte, PCT Publication No. WO 99/61471, 02 Dec. 1999. As used herein, "TWEAKR" includes polypeptides having these sequences, and in particular comprising amino acids 28-79 of SEQ ID NO:7, as well as naturally occurring variants thereof.

In one aspect of the invention, a polypeptide comprising a soluble TWEAK receptor fragment and an oligomerization domain is used as a TWEAKR antagonist to inhibit angiogenesis and/or to inhibit the binding of TWEAK ligand to TWEAKR.

Soluble polypeptides are capable of being secreted from the cells in which they are expressed. The use of soluble forms of polypeptides is advantageous for certain applications. Purification of the polypeptides from recombinant host cells is facilitated since the polypeptides are secreted, and soluble proteins are generally suited for parenteral administration. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. Soluble polypeptides may be prepared by any of a number of conventional techniques. A DNA sequence encoding a desired soluble polypeptide may be subcloned into an expression vector for production of the polypeptide, or the desired encoding DNA fragment may be chemically synthesized.

Soluble TWEAKR polypeptides comprise all or part of the TWEAKR extracellular domain, but generally lack the transmembrane domain or a fragment thereof that would cause retention of the polypeptide at the cell surface. Soluble polypeptides may include part of the transmembrane domain or all or part of the cytoplasmic domain as long as the polypeptide is secreted from the cell in which it is produced. Soluble TWEAKR polypeptides advantageously comprise a native or heterologous signal peptide when initially synthesized, to promote secretion from the cell, but the signal sequence is cleaved upon secretion. The term "TWEAKR extracellular domain" is intended to encompass all or part of the native TWEAKR extracellular domain, as well as related forms including but not limited to: (a) fragments, (b) variants, (c) derivatives, and (d) fusion polypeptides. The ability of these related forms to inhibit angiogenesis or other TWEAKR-mediated responses may be determined in vitro or in vivo, using methods such as those exemplified below or using other assays known in the art. Examples of soluble TWEAKR polypeptides are provided below.

Multimeric soluble TWEAKR fragments are dimers, trimers, tetramers, pentamers, hexamers, heptamers, octamers, nonamers, decamers, or higher multimers of a soluble fragment of TWEAKR. Multimers may be linked together by any means known in the art. For example, they can be part of a continuous polypeptide chain, wherein each monomer can be linked to its neighboring monomer(s) directly via peptide bond(s), or indirectly, through one or more intervening amino acids and peptide bonds, e.g., through a linker. Multimers also can be joined to each other by, for example, other types of covalent bonds, e.g., by disulfide bonds formed between cysteine residues on different soluble TWEAKR polypeptides.

Oligomerization domains are polypeptides that cause polypeptides comprising them to oligomerize, i.e., to form covalent and/or non-covalent associations with another polypeptide comprising a corresponding oligomerization domain. Thus, two or more polypeptides are "oligomerized" if they are bound to each other via their oligomerization domains. Any oligomerization domain known in the art can be used. Examples include leucine zippers and certain polypeptides derived from antibodies, e.g., Fc domains, as described in more detail below. The polypeptides in an oligomer can have identical polypeptide sequences, similar polypeptide sequences, or different polypeptide sequences. In particular embodiments, the oligimerized polypeptides of the present invention comprise from four to fourteen soluble TWEAKR fragments.

In some embodiments, a polypeptide comprising a multimeric soluble TWEAKR fragment and an oligmerization domain is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al. (Proc. Natl. Acad. Sci. USA 88:10535, 1991); Byrn et al. (Nature 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a TWEAKR-Fc oligomer comprising two polypeptides, each polypeptide comprising two soluble TWEAKR fragments and an Fc domain (diTWEAKR-Fc). A polynucleotide encoding the diTWEAKR-Fc polypeptide is inserted into an appropriate expression vector. diTWEAKR-Fc polypeptides are expressed in host cells transformed with the recombinant expression vector, and allowed to assemble much like antibody molecules, whereupon interchain disulfide bonds form between the Fc moieties to yield tetravalent soluble TWEAKR. The term "Fc polypeptide" as used herein includes native and mutein forms of polypeptides derived from the Fc region of an antibody. Truncated forms of such polypeptides containing the hinge region that promotes dimerization are also included.

One suitable Fc polypeptide, described in PCT application WO 93/10151, is a single chain polypeptide extending from the N-terminal hinge region to the native C-terminus of the Fc region of a human IgG1 antibody. Another useful Fc polypeptide is the Fc mutein described in U.S. Pat. 5,457,035 and by Baum et al., EMBO J. 13:3992, 1994. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. Fusion polypeptides comprising Fc moieties, and multimers formed therefrom, offer an advantage of facile purification by affinity chromatography over Protein A or Protein G columns, and Fc fusion polypeptides may provide a longer in vivo half life, which is useful in therapeutic applications, than unmodified polypeptides.

In other embodiments, a multimeric soluble TWEAKR fragment may be substituted for the variable portion of an antibody heavy or light chain. If fusion proteins are made with both heavy and light chains of an antibody, it is possible to form a soluble TWEAKR oligomer with eight or more soluble TWEAKR fragments.

In another embodiment, the oligomerization domain comprises a leucine zipper domain. Leucine zipper domains are peptides that promote oligomerization of the proteins in which they are found. Leucine zippers were originally identified in several DNA-binding proteins (Landschulz et al., Science 240:1759, 1988), and have since been found in a variety of different proteins. Among the known leucine zippers are naturally occurring peptides and derivatives thereof that dimerize or trimerize. Examples of leucine zipper domains suitable for producing soluble multimeric proteins are described in PCT application WO 94/10308, and the leucine zipper derived from lung surfactant protein D (SPD) described in Hoppe et al. FEBS Lett. 344:191, 1994. The use of a modified leucine zipper that allows for stable trimerization of a heterologous protein fused thereto is described in Fanslow et al., Semin. Immunol. 6:267, 1994. Recombinant fusion proteins comprising a soluble TWEAKR polypeptide fused to a leucine zipper peptide are expressed in suitable host cells, and the soluble TWEAKR multimer that forms is recovered from the culture supernatant.

Alternatively, the polypeptides of the invention comprise peptide linkers (spacers). A linker is a sequence of one or more amino acids whose amino terminal end is peptide bonded to a first polypeptide and whose carboxy terminal end is peptide bonded to a second polypeptide such that the first polypeptide, the linker, and the second polypeptide form a contiguous sequence of amino acids. Such a linker is said to "join" the first polypeptide and the second polypeptide, in contrast to a first polypeptide and a second polypeptide that are joined together without an intervening polypeptide sequence (i. e., without a linker). Among the suitable peptide linkers are those described in U.S. Pat. Nos. 4,751,180, 4,935, 233, and 5,073,627. A DNA sequence encoding a desired peptide linker may be inserted between, and in the same reading frame as, for example, the DNA sequences encoding TWEAKR fragments, and/or between the polynucleotide sequences encoding the TWEAKR fragments and the oligomerization domain, using conventional techniques known in the art. For example, a chemically synthesized oligonucleotide encoding the linker may be ligated between sequences encoding soluble TWEAKR fragments. In particular embodiments, a polypeptide of the invention comprises from two to four soluble TWEAKR fragments, separated by peptide linkers, and an oligomerization domain.

The present invention encompasses the use of various forms of oligomerized soluble TWEAKR multimers that inhibit angiogenesis and/or other TWEAKR-mediated responses. The term "oligomerized soluble TWEAKR multimer" is intended to encompass oligomerized multimers containing all or part of the native TWEAKR extracellular domain, as well as related forms including, but not limited to, oligomerized multimers of, fragments, variants, derivatives, and fusion polypeptides of soluble TWEAKR. The ability of these related forms to inhibit angiogenesis or other TWEAKR-mediated responses may be determined in vitro or in vivo, using methods such as those exemplified in the examples or using other assays known in the art.

Among the polypeptides, multimers and oligomers useful in practicing the present invention are polypeptides comprising TWEAKR variants that retain the ability to bind ligand and/or inhibit angiogenesis or other TWEAKR-mediated responses. Such TWEAKR variants include polypeptides that are substantially homologous to native TWEAKR, but which have an amino acid sequence different from that of a native TWEAKR because of one or more deletions, insertions or substitutions. Particular embodiments include, but are not limited to, TWEAKR polypeptides that comprise from one to ten deletions, insertions or substitutions of amino acid residues, when compared to a native TWEAKR sequence. Included as variants of TWEAKR polypeptides are those variants that are naturally occurring, such as allelic forms and alternatively spliced forms, as well as variants that have been constructed by modifying the amino acid sequence of a TWEAKR polypeptide or the nucleotide sequence of a nucleic acid encoding a TWEAKR polypeptide.

Generally, substitutions for one or more amino acids present in the native polypeptide should be made conservatively. Examples of conservative substitutions include substitution of amino acids outside of the active domain(s), and substitution of amino acids that do not alter the secondary and/or tertiary structure of TWEAKR. Additional examples include substituting one aliphatic residue for another, such as Ile, Val, Leu, or Ala for one another, or substitutions of one polar residue for another, such as between Lys and Arg; Glu and Asp; or Gln and Asn, or substitutions of one aromatic residue for another, such as Phe, Trp, or Tyr for one another. Other such conservative substitutions, for example, substitutions of entire regions having similar hydrophobicity characteristics, are known in the art.

In some preferred embodiments the TWEAKR variant is at least about 70% identical in amino acid sequence to the amino acid sequence of native TWEAKR; in some preferred embodiments the TWEAKR variant is at least about 80% identical in amino acid sequence to the amino acid sequence of native TWEAKR. In some more preferred embodiments the TWEAKR variant is at least about 90% identical in amino acid sequence to the amino acid sequence of native TWEAKR; in some more preferred embodiments the TWEAKR variant is at least about 95% identical in amino acid sequence to the amino acid sequence of native TWEAKR. In some most preferred embodiments the TWEAKR variant is at least about 98% identical in amino acid sequence to the amino acid sequence of native TWEAKR; in some most preferred embodiments the TWEAKR variant is at least about 99% identical in amino acid sequence to the amino acid sequence of native TWEAKR. Percent identity, in the case of both polypeptides and nucleic acids, may be determined by visual inspection. Percent identity may also be determined using the alignment method of Needleman and Wunsch (J. Mol. Biol. 48:443, 1970) as revised by Smith and Waterman (Adv. Appl. Math 2:482, 1981. Preferably, percent identity is determined by using a computer program, for example, the GAP computer program version 10.x available from the Genetics Computer Group (GCG; Madison, Wis., see also Devereux et al., *Nucl Acids Res.* 12:387, 1984). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353-358, 1979 for amino acids; (2) a penalty of 30 (amino acids) or 50 (nucleotides) for each gap and an additional 1 (amino acids) or 3 (nucleotides) penalty for each symbol in each gap; (3) no penalty for end gaps; and (4) no maximum penalty for long gaps. Other programs used by one skilled in the art of sequence comparison may also be used. For fragments of TWEAKR, the percent identity is calculated based on that portion of TWEAKR that is present in the fragment.

The present invention further encompasses the use of soluble TWEAKR polypeptides with or without associated native-pattern glycosylation. TWEAKR expressed in yeast or mammalian expression systems (e.g., COS-1 or COS-7 cells) may be similar to or significantly different from a native TWEAKR polypeptide in molecular weight and glycosylation pattern, depending upon the choice of expression system. Expression of TWEAKR polypeptides in bacterial expression systems, such as *E. coli*, provides non-glycosylated molecules. Different host cells may also process polypeptides differentially, resulting in heterogeneous mixtures of polypeptides with variable N- or C-termini.

The primary amino acid structure of soluble TWEAKR polypeptides may be modified to create derivatives by forming covalent or aggregative conjugates with other chemical moieties, such as glycosyl groups, lipids, phosphate, acetyl groups and the like. Covalent derivatives of TWEAKR may be prepared by linking particular functional groups to TWEAKR amino acid side chains or at the N-terminus or C-terminus of a TWEAKR polypeptide.

Fusion polypeptides of soluble TWEAKR that are useful in practicing the invention also include covalent or aggregative conjugates of a TWEAKR polypeptide with other polypeptides added to provide novel polyfunctional entities.

Recombinant Production of TWEAK Receptor Polypeptides

TWEAKR polypeptides, including soluble TWEAKR polypeptides, fragments, and fusion polypeptides, used in the present invention may be prepared using a recombinant expression system. Host cells transformed with a recombinant expression vector ("recombinant host cells") encoding the TWEAKR polypeptide are cultured under conditions that promote expression of TWEAKR and the TWEAKR is recovered. TWEAKR polypeptides can also be produced in transgenic plants or animals, or by chemical synthesis.

The invention encompasses nucleic acid molecules encoding the TWEAKR polypeptides used in the invention, including: (a) nucleic acids that encode residues 28-79 of SEQ ID NO:7 and fragments thereof that bind TWEAK; (b) nucleic acids that are at least 70%, 80%, 90%, 95%, 98%, or 99% identical to a nucleic acid of (a), and which encode a polypeptide capable of binding TWEAK; and (c) nucleic acids that hybridize at moderate stringency to a nucleic acid of (a), and which encode a polypeptide capable of binding TWEAK.

Due to degeneracy of the genetic code, there can be considerable variation in nucleotide sequences encoding the same amino acid sequence. Included as embodiments of the invention are nucleic acid sequences capable of hybridizing under moderately stringent conditions (e.g., prewashing solution of 5×SSC, 0.5% SDS, 1.0 mM EDTA (pH 8.0) and hybridization conditions of 50° C., 5×SSC, overnight) to DNA sequences encoding TWEAKR. The skilled artisan can determine additional combinations of salt and temperature that constitute moderate hybridization stringency (see also, Sambrook, *Molecular Cloning: A Laboratory Manual*, Cold Spring Harbor Laboratory Press, 1989; Maniatis, *Molecular Cloning: A Laboratory Manual*, Cold Spring Harbor Laboratory Press, 1982; and Ausubel, *Current Protocols in Molecular Biology*, Wiley and Sons, 1989 and later versions, which are incorporated herein by reference). Conditions of higher stringency include higher temperatures for hybridization and post-hybridization washes, and/or lower salt concentration. Percent identity of nucleic acids may be determined using the methods described above for polypeptides, i.e., by methods including visual inspection and the use of computer programs such as GAP.

Any suitable expression system may be employed for the production of recombinant TWEAKR. Recombinant expression vectors include DNA encoding a TWEAKR polypeptide operably linked to suitable transcriptional and translational regulatory nucleotide sequences, such as those derived from a mammalian, microbial, viral, or insect gene. Nucleotide sequences are operably linked when the regulatory sequence functionally relates to the TWEAKR DNA sequence. Thus, a promoter nucleotide sequence is operably linked to a TWEAKR DNA sequence if the promoter nucleotide sequence controls the transcription of the TWEAKR DNA sequence. Examples of regulatory sequences include transcriptional promoters, operators, or enhancers, an mRNA ribosomal binding site, and appropriate sequences which control transcription and translation initiation and termination. A sequence encoding an appropriate signal peptide (native or heterologous) can be incorporated into expression vectors. A DNA sequence for a signal peptide (referred to by a variety of names including secretory leader, leader peptide, or leader) may be fused in frame to the TWEAKR sequence so that the TWEAKR polypeptide is initially translated as a fusion protein comprising the signal peptide. A signal peptide that is functional in the intended host cells promotes extracellular secretion of the TWEAKR polypeptide. The signal peptide is cleaved from the TWEAKR polypeptide upon secretion of TWEAKR from the cell.

Suitable host cells for expression of TWEAKR polypeptides include prokaryotes, yeast and higher eukaryotic cells, including insect and mammalian cells. Appropriate cloning and expression vectors for use with bacterial, fungal, yeast, insect, and mammalian cellular hosts are described, for example, in Pouwels et al. *Cloning Vectors: A Laboratory Manual*, Elsevier, New York, 1985.

Prokaryotes include gram negative or gram positive organisms, for example, *E. coli* or *Bacilli*. Suitable prokaryotic host cells for transformation include, for example, *E. coli*, *Bacillus subtilis*, *Salmonella typhimurium*, and various other species within the genera *Pseudomonas, Streptomyces*, and *Staphylococcus*. In a prokaryotic host cell, such as *E. coli*, TWEAKR polypeptides may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker gene(s). A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a TWEAKR DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., Nature 275:615, 1978; Goeddel et al., Nature 281:544, 1979), tryptophan (trp) promoter system (Goeddel et al., Nucl. Acids Res. 8:4057, 1980; EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage λ $P_L$ promoter and a cI857ts thermolabile repressor sequence. Plasmid vectors available from the American Type Culture Collection which incorporate derivatives of the λ $P_L$ promoter include plasmid pHUB2 (resident in *E. coli* strain JMB9, ATCC 37092) and pPLc28 (resident in *E. coli* RR1, ATCC 53082).

TWEAKR polypeptides may also be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, 1980) or other glycolytic enzymes (Hess et al., J. Adv. Enzyme Reg. 7:149, 1968; Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (J. Biol. Chem. 258:2674, 1982) and Beier et al. (Nature 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of recombinant polypeptides. The α-factor leader sequence is often inserted between the promoter sequence and the structural gene sequence. See, e.g., Kurjan et al., Cell 30:933, 1982; Bitter et al., Proc. Natl. Acad. Sci. USA 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., Proc. Natl. Acad. Sci. USA 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/ml adenine and 20 μg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Derepression of the ADH2 promoter occurs when glucose is exhausted from the medium.

Insect host cell culture systems also may be employed to express recombinant TWEAKR polypeptides, including soluble TWEAKR polypeptides. Bacculovirus systems for production of heterologous polypeptides in insect cells are reviewed by Luckow and Summers, Bio/Technology 6:47, 1988.

Mammalian cells are particularly preferred for use as host cells. Examples of suitable mammalian host cell lines include the COS-7 line of monkey kidney cells (ATCC CRL 1651)

(Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991). For the production of therapeutic polypeptides it is particularly advantageous to use a mammalian host cell line which has been adapted to grow in media that does not contain animal proteins.

Established methods for introducing DNA into mammalian cells have been described (Kaufman, R. J., *Large Scale Mammalian Cell Culture*, 1990, pp. 15-69). Additional protocols using commercially available reagents, such as Lipofectamine (Gibco/BRL) or Lipofectamine-Plus, can be used to transfect cells (Felgner et al., Proc. Natl. Acad. Sci. USA 84:7413, 1987). In addition, electroporation can be used to transfect mammalian cells using conventional procedures, such as those in Sambrook et al. *Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., Meth. in Enzymology 185:487, 1990, describes several selection schemes, such as dihydrofolate reductase (DHFR) resistance. A suitable host strain for DHFR selection can be CHO strain DX-B11, which is deficient in DHFR (Urlaub and Chasin, Proc. Natl. Acad. Sci. USA 77:4216, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273:113, 1978; Kaufman, Meth. in Enzymology, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534) and the tripartite leader (TPL) and VA gene RNAs from Adenovirus 2 (Gingeras et al., J. Biol. Chem. 257:13475, 1982). The internal ribosome entry site (IRES) sequences of viral origin allows dicistronic mRNAs to be translated efficiently (Oh and Sarnow, Current Opinion in Genetics and Development 3:295, 1993; Ramesh et al., Nucleic Acids Research 24:2697, 1996). Expression of a heterologous cDNA as part of a dicistronic mRNA followed by the gene for a selectable marker (e.g. DHFR) has been shown to improve transfectability of the host and expression of the heterologous cDNA (Kaufman, Meth. in Enzymology, 1990). Exemplary expression vectors that employ dicistronic mRNAs are pTR-DC/GFP described by Mosser et al., Biotechniques 22:150, 1997, and p2A5I described by Morris et al., *Animal Cell Technology*, 1997, pp. 529-534.

A useful high expression vector, pCAVNOT, has been described by Mosley et al., Cell 59:335, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are known in the art.

Regarding signal peptides that may be employed in producing TWEAKR polypeptides, the native TWEAKR signal peptide may used or it may be replaced by a heterologous signal peptide or leader sequence, if desired. The choice of signal peptide or leader may depend on factors such as the type of host cells in which the recombinant TWEAKR is to be produced. Examples of heterologous signal peptides that are functional in mammalian host cells include the signal sequence for interleukin-7 (IL-7) described in U.S. Pat. No. 4,965,195, the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Using the techniques of recombinant DNA including mutagenesis and the polymerase chain reaction (PCR), the skilled artisan can produce DNA sequences that encode TWEAKR polypeptides comprising various additions or substitutions of amino acid residues or sequences, or deletions of terminal or internal residues or sequences, including TWEAKR fragments, variants, derivatives, and fusion polypeptides.

Transgenic animals, including mice, goats, sheep, and pigs, and transgenic plants, including tobacco, tomato, legumes, grasses, and grains, may also be used as bioreactors for the production of TWEAKR polypeptides, including soluble TWEAKR polypeptides. In the case of transgenic animals, it is particularly advantageous to construct a chimeric DNA including a TWEAKR coding sequence operably linked to cis-acting regulatory sequences that promote expression of the soluble TWEAKR in milk and/or other body fluids (see, e.g., U.S. Pat. No. 5,843,705; U.S. Pat. No. 5,880,327). In the case of transgenic plants it is particularly advantageous to produce TWEAKR in a particular cell type, tissue, or organ (see, e.g., U.S. Pat. No. 5,639,947; U.S. Pat. No. 5,889,189).

The skilled artisan will recognize that the procedure for purifying expressed soluble TWEAKR polypeptides will vary according to the host system employed, and whether or not the recombinant polypeptide is secreted. Soluble TWEAKR polypeptides may be purified using methods known in the art, including one or more concentration, salting-out, ion exchange, hydrophobic interaction, affinity purification, HPLC, or size exclusion chromatography steps. Fusion polypeptides comprising Fc moieties (and multimers formed therefrom) offer the advantage of facile purification by affinity chromatography over Protein A or Protein G columns.

Methods of Treatment

Described below are methods and compositions employing the TWEAK receptor or ligand, or the genes encoding the TWEAK receptor or ligand, to promote or suppress angiogenesis in a target tissue or group of cells. The terms "treat," "treating," "treatment," "therapy," "therapeutic," and the like are intended to include preventative therapy, prophylactic therapy, ameliorative therapy, and curative therapy.

The disclosed polypeptides, compositions, and methods are used to inhibit angiogenesis or other TWEAKR-mediated responses in a mammal in need of such treatment. The term "TWEAKR-mediated response" includes any cellular, physiological, or other biological response that is caused at least in part by the binding of TWEAK ligand to TWEAKR, or which may be inhibited or suppressed, in whole or in part, by blocking TWEAK from binding to TWEAKR. The treatment is advantageously administered in order to prevent the onset or the recurrence of a disease or condition mediated by angiogenesis, or to treat a mammal that has a disease or condition mediated by angiogenesis. Diseases and conditions mediated by angiogenesis include but are not limited to ocular disorders, malignant and metastatic conditions, and inflammatory diseases.

Among the ocular disorders that can be treated according to the present invention are eye diseases characterized by ocular neovascularization including, but not limited to, diabetic retinopathy (a major complication of diabetes), retinopathy of prematurity (this devastating eye condition, that frequently leads to chronic vision problems and carries a high risk of blindness, is a severe complication during the care of premature infants), neovascular glaucoma, retinoblastoma, retrolental fibroplasia, rubeosis, uveitis, macular degeneration, and corneal graft neovascularization. Other eye inflammatory diseases, ocular tumors, and diseases associated with choroidal or iris neovascularization can also be treated according to the present invention.

The present invention can also be used to treat malignant and metastatic conditions such as solid tumors. Solid tumors include both primary and metastatic sarcomas and carcinomas.

The present invention can also be used to treat inflammatory diseases including, but not limited to, arthritis, rheumatism, and psoriasis.

Other diseases and conditions that can be treated according to the present invention include benign tumors and preneoplastic conditions, myocardial angiogenesis, hemophilic joints, scleroderma, vascular adhesions, atherosclerotic plaque neovascularization, telangiectasia, and wound granulation.

Disease states that are angiogenic-dependent include coronary or peripheral atherosclerosis and ischemia of any tissue or organ, including the heart, liver, brain, and the like. These types of diseases can be treated by compositions that promote angiogenesis.

The methods according to the present invention can be tested in in vivo animal models to confirm the desired prophylactic or therapeutic activity, as well as to determine the optimal therapeutic dosage, prior to administration to humans.

The amount of a particular TWEAKR antagonist that will be effective in a particular method of treatment depends upon age, type and severity of the condition to be treated, body weight, desired duration of treatment, method of administration, and other parameters. Effective dosages are determined by a physician or other qualified medical professional. Typical effective dosages are about 0.01 mg/kg to about 100 mg/kg body weight. In some preferred embodiments the dosage is about 0.1-50 mg/kg; in some preferred embodiments the dosage is about 0.5-10 mg/kg. The dosage for local administration is typically lower than for systemic administration. In some embodiments a single administration is sufficient; in some embodiments the TWEAKR antagonist is administered as multiple doses over one or more days.

The TWEAKR antagonists are typically administered in the form of a pharmaceutical composition comprising one or more pharmacologically acceptable carriers. Pharmaceutically acceptable carriers include diluents, fillers, adjuvants, excipients, and vehicles which are pharmaceutically acceptable for the route of administration, and may be aqueous or oleaginous suspensions formulated using suitable dispersing, wetting, and suspending agents.

Pharmaceutically acceptable carriers are generally sterile and free of pyrogenic agents, and may include water, oils, solvents, salts, sugars and other carbohydrates, emulsifying agents, buffering agents, antimicrobial agents, and chelating agents. The particular pharmaceutically acceptable carrier and the ratio of active compound to carrier are determined by the solubility and chemical properties of the composition, the mode of administration, and standard pharmaceutical practice.

The compositions as described herein may be contained in a vial, bottle, tube, syringe inhaler or other container for single or multiple administrations. Such containers may be made of glass or a polymer material such as polypropylene, polyethylene, or polyvinylchloride, for example. Preferred containers may include a seal, or other closure system, such as a rubber stopper that may be penetrated by a needle in order to withdraw a single dose and then re-seal upon removal of the needle. All such containers for injectable liquids, lyophilized formulations, reconstituted lyophilized formulations or reconstitutable powders for injection known in the art or for the administration of aerosolized compositions are contemplated for use in the presently disclosed compositions and methods.

The TWEAKR antagonists are administered to the patient in a manner appropriate to the indication. Thus, for example, a TWEAKR antagonist, or a pharmaceutical composition thereof, may be administered by intravenous, transdermal, intradermal, intraperitoneal, intramuscular, intranasal, epidural, oral, topical, subcutaneous, intracavity, sustained release from implants, peristaltic routes, or by any other suitable technique. Parenteral administration is preferred.

In certain embodiments of the claimed invention, the treatment further comprises treating the mammal with one or more additional chemotherapeutic agents. The additional chemotherapeutic agent(s) may be administered prior to, concurrently with, or following the administration of the TWEAKR antagonist. The use of more than one chemotherapeutic agent is particularly advantageous when the mammal that is being treated has a solid tumor. In some embodiments of the claimed invention, the treatment further comprises treating the mammal with radiation. Radiation, including brachytherapy and teletherapy, may be administered prior to, concurrently with, or following the administration of the second chemotherapeutic agent(s) and/or TWEAKR antagonist.

When the mammal that is being treated has a solid tumor, the method preferably includes the administration of, in addition to a TWEAKR antagonist, one or more chemotherapeutic agents selected from the group consisting of alkylating agents, antimetabolites, vinca alkaloids and other plant-derived chemotherapeutics, nitrosoureas, antitumor antibiotics, antitumor enzymes, topoisomerase inhibitors, platinum analogs, adrenocortical suppressants, hormones, hormone agonists and antagonists, antibodies, immunotherapeutics, blood cell factors, radiotherapeutics, and biological response modifiers.

In some preferred embodiments the method includes administration of, in addition to a TWEAKR antagonist, one or more chemotherapeutic agents selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons (including alpha, beta, or delta), and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone.

In some preferred embodiments the method includes administration of, in addition to a TWEAKR antagonist, one or more chemotherapeutic agents, including various soluble forms thereof, selected from the group consisting of Flt3 ligand, CD40 ligand, interleukin-2, interleukin-12, 4-1BB ligand, anti4-1BB antibodies, TNF antagonists and TNF receptor antagonists, TRAIL, VEGF antagonists, VEGF receptor (including VEGF-R1 and VEGF-R2, also known as Flt1 and Flk1 or KDR) antagonists, Tek antagonists, and CD148 (also referred to as DEP-1, ECRTP, and PTPRJ, see Takahashi et al., J. Am. Soc. Nephrol. 10:2135-45, 1999) agonists. In some preferred embodiments the TWEAKR antagonists of the invention are used as a component of, or in combination with, "metronomic therapy," such as that described by Browder et al. and Klement et aL (Cancer Research 60:1878, 2000; J. Clin. Invest. 105(8):R15, 2000; see also Barinaga, Science 288:245, 2000).

The polypeptides, compositions, and methods of the present invention may be used as a first line treatment, for the treatment of residual disease following primary therapy, or as an adjunct to other therapies including chemotherapy, surgery, radiation, and other therapeutic methods known in the art.

When the nucleic acid sequences of the present invention are delivered according to the methods disclosed herein, it is advantageous to use a delivery mechanism so that the sequences will be incorporated into a cell for expression. Delivery systems that may advantageously be employed in the contemplated methods include the use of, for example, viral delivery systems such as retroviral and adenoviral vectors, as well as non-viral delivery systems. Such delivery systems are well known by those skilled in the art.

Methods of Screening

The TWEAK receptor as described herein may be used in a variety of methods of screening to isolate, for example, TWEAKR agonists and antagonists. TWEAKR agonists are compounds that promote the biological activity of TWEAKR and TWEAKR antagonists are compounds that inhibit the biological activity of TWEAKR. Compounds identified via the following screening assays can be used in compositions and methods for modulating angiogenesis to treat a variety of disease states. The present invention provides methods of screening for compounds that (1) modulate TWEAK receptor or ligand gene expression in a target tissue or cell, (2) modulate the TWEAK receptor-ligand interaction to regulate angiogenesis; (3) bind to the TWEAK receptor or ligand to influence angiogenesis; or (4) interfere with or regulate the bound TWEAK receptor-ligand complex's influence on downstream events such as angiogenesis.

The present invention contemplates the use of assays that are designed to identify compounds that modulate the activity of a TWEAK receptor or ligand gene (i.e., modulate the level of TWEAK gene expression and/or modulate the level of TWEAK gene product activity). Assays may additionally be utilized that identify compounds that bind to TWEAK gene regulatory sequences (e.g., promoter sequences; see e.g., Platt, 1994, J. Biol. Chem. 269, 28558-28562), and that may modulate the level of TWEAK gene expression.

Such an assay may involve, for example, the use of a control system, in which transcription and translation of the TWEAK receptor or ligand gene occurs, in comparison to a system including a test compounds suspected of influencing normal transcription or translation of a TWEAK gene. For example, one could determine the rate of TWEAK receptor RNA produced by cardiac cells, and use this to determine if a test compound influences that rate. To assess the influence of a test compound suspected to influence this normal rate of transcription, one would first determine the rate of TWEAK receptor RNA production in a cardiac cell culture by, for example, Northern Blotting. One could then administer the test compound to a cardiac cell culture under otherwise identical conditions as the control culture. Then the rate of TWEAK receptor RNA in the culture treated with the test compound could be determined by, for example, Northern Blotting, and compared to the rate of TWEAK receptor RNA produced by the control culture cells. An increase in the TWEAK receptor RNA in the cells contacted with the test compound relative to control cells is indicative of a stimulator of TWEAK receptor gene transcription and/or translation in cardiac cells, while a decrease is indicative of an inhibitor of TWEAK receptor gene transcription and/or translation in cardiac cells.

There are a variety of other methods that can be used to determine the level of TWEAK receptor or ligand gene expression as well, and may further be used in assays to determine the influence of a test compound on the level of TWEAK receptor or ligand gene expression. For example, RNA from a cell type or tissue known, or suspected, to express the TWEAK receptor or ligand gene, such as cardiac, may be isolated and tested utilizing hybridization or PCR techniques. The isolated cells can be derived from cell culture or from a patient. The analysis of cells taken from culture may be a necessary step in the assessment of cells to be used as part of a cell-based gene therapy technique or, alternatively, to test the effect of compounds on the expression of the TWEAK receptor or ligand gene. Such analyses may reveal both quantitative and qualitative aspects of the expression pattern of the TWEAK receptor or ligand gene, including activation or inactivation of TWEAK receptor or ligand gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the TWEAK receptor or ligand gene nucleic acid segments described above. The preferred lengths of such nucleic acid reagents are at least 9-30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such TWEAK receptor or ligand gene expression assays "in situ", i.e., directly upon tissue sections (fixed and/or frozen) of patient tissue obtained from biopsies or resections, such that no nucleic acid purification is necessary. TWEAK receptor or ligand gene nucleic acid segments described above can be used as probes and/or primers for such in situ procedures (see, for example, Nuovo, G. J., 1992, "PCR In Situ Hybridization: Protocols And Applications", Raven Press, N.Y.).

Compounds identified via assays such as those described herein may be useful, for example, in modulating angiogenesis influenced by the TWEAK receptor-ligand interaction. Such methods of stimulating or inhibiting TWEAK-influenced angiogenesis are discussed herein.

Alternatively, assay systems may be designed to identify compounds capable of binding the TWEAK receptor or ligand polypeptide of the invention and thereby influencing angiogenesis resulting from this interaction. Compounds identified may be useful, for example, in modulating the vascularization of target tissues or cells, may be utilized in screens for identifying compounds that disrupt normal TWEAK receptor-ligand interactions, or may in themselves disrupt such interactions.

The principle of the assays used to identify compounds that bind to the TWEAK receptor or ligand involves preparing a reaction mixture of the TWEAK receptor or ligand and the test compound under conditions and for a time sufficient to allow the two components to interact and bind, thus forming a complex that can be removed and/or detected in the reaction mixture. These assays can be conducted in a variety of ways. For example, one method to conduct such an assay screening for compounds that bind to the TWEAK receptor, would involve anchoring the TWEAK receptor or the test substance onto a solid phase and detecting TWEAK receptor/test compound complexes anchored on the solid phase at the end of the reaction. In one embodiment of such a method, the TWEAK receptor may be anchored onto a solid surface, and the test compound, which is not anchored, may be labeled, either directly or indirectly. Alternatively, these same methods could be used to screen for test compounds that bind to the TWEAK ligand rather than receptor.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for the TWEAK receptor or ligand or the test compound to anchor any complexes formed in solution, and a labeled antibody specific for the other component of the possible complex to detect anchored complexes.

Those compounds identified as binding agents for either the TWEAK receptor or the TWEAK ligand may further be assessed for their ability to interfere with TWEAK receptor-ligand interaction, as described below, and thereby suppress or promote angiogenesis resulting from TWEAK receptor-ligand interaction. Such compounds may then be used therapeutically to stimulate or inhibit angiogenesis.

The TWEAK receptor and ligand polypeptides of the present invention may also be used in a screening assay to identify compounds and small molecules which specifically interact with the disclosed TWEAK receptor or ligand to either inhibit (antagonize) or enhance (agonize) interaction between these molecules. Thus, for example, polypeptides of the invention may be used to identify antagonists and agonists from cells, cell-free preparations, chemical libraries, and natural product mixtures. The antagonists and agonists may be natural or modified substrates, ligands, enzymes, receptors, etc. of the polypeptides of the instant invention, or may be structural or functional mimetics of the polypeptides. Potential antagonists of the TWEAK receptor-ligand interaction of the instant invention may include small molecules, peptides, and antibodies that bind to and occupy a binding site of the polypeptides, causing them to be unavailable to interact and therefore preventing their normal ability to modulate angiogenesis. Other potential antagonists are antisense molecules which may hybridize to mRNA in vivo and block translation of the mRNA into the polypeptides of the instant invention. Potential agonists include small molecules, peptides and antibodies which bind to the instant TWEAK polypeptides and influence angiogenesis as caused by the disclosed interactions of the TWEAK polypeptides of the instant invention.

Small molecule agonists and antagonists are usually less than 10K molecular weight and may possess a number of physiochemical and pharmacological properties that enhance cell penetration, resist degradation and prolong their physiological half-lives. (Gibbs, "Pharmaceutical Research in Molecular Oncology," *Cell*, Vol. 79, (1994).) Antibodies, which include intact molecules as well as fragments such as Fab and F(ab')2 fragments, may be used to bind to and inhibit the polypeptides of the instant invention by blocking the commencement of a signaling cascade. It is preferable that the antibodies are humanized, and more preferable that the antibodies are human. The antibodies of the present invention may be prepared by any of a variety of well-known methods.

Specific screening methods are known in the art and many are extensively incorporated in high throughput test systems so that large numbers of test compounds can be screened within a short amount of time. The assays can be performed in a variety of formats, including protein-protein binding assays, biochemical screening assays, immunoassays, cell based assays, etc. These assay formats are well known in the art. The screening assays of the present invention are amenable to screening of chemical libraries and are suitable for the identification of small molecule drug candidates, antibodies, peptides and other antagonists and agonists.

One embodiment of a method for identifying molecules which antagonize or inhibit TWEAK receptor-ligand interaction involves adding a candidate molecule to a medium which contains cells that express the polypeptides of the instant invention; changing the conditions of said medium so that, but for the presence of the candidate molecule, the polypeptides would interact; and observing the binding and inhibition of angiogenesis. Binding of the TWEAK receptor and ligand can be determined according to competitive binding assays outlined above, and well known in the art. The angiogenic effect of this binding can be determined via cell proliferation assays such as, for example, cell density assays, or other cell proliferation assays that are also well-known in the art. The activity of the cells contacted with the candidate molecule may then be compared with the identical cells which were not contacted and agonists and antagonists of the TWEAK polypeptide interactions of the instant invention may be identified. The measurement of biological activity may be performed by a number of well-known methods such as measuring the amount of protein present (e.g. an ELISA) or of the protein's activity. A decrease in biological stimulation or activation would indicate an antagonist. An increase would indicate an agonist.

Screening assays can further be designed to find molecules that mimic the biological activity resulting from the TWEAK polypeptide interactions of the instant invention. Molecules which mimic the biological activity of a polypeptide may be useful for enhancing the biological activity of the polypeptide. To identify compounds for therapeutically active agents that mimic the biological activity of a polypeptide, it must first be determined whether a candidate molecule binds to the polypeptide. A binding candidate molecule is then added to a biological assay to determine its biological effects. The biological effects of the candidate molecule are then compared to those of the polypeptide.

Additionally, complex formation within reaction mixtures containing the test compound and normal TWEAK receptor or ligand gene protein may also be compared to complex formation within reaction mixtures containing the test compound and a mutant TWEAK receptor or ligand gene protein. This comparison may be important in those cases wherein it is desirable to identify compounds that disrupt interactions of mutant but not normal TWEAK receptor or ligand gene proteins.

The assay for compounds that interfere with the interaction of the TWEAK receptor or ligand gene products and binding partners can be conducted in a heterogeneous or homogeneous format. Heterogeneous assays involve anchoring either the TWEAK receptor or ligand gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the TWEAK receptor or ligand gene products and the binding partners, e.g., by competition, can be identified by conducting the reaction in the presence of the test substance; i.e., by adding the test substance to the reaction mixture prior to or simultaneously with the TWEAK receptor and ligand gene products. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the TWEAK receptor or ligand gene product, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the TWEAK receptor or ligand gene product and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the TWEAK receptor or ligand gene product is prepared in which either the TWEAK receptor or ligand gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt TWEAK receptor or ligand gene product interaction can be identified.

In a particular embodiment, the TWEAK receptor or ligand gene product can be prepared for immobilization using recombinant DNA techniques. For example, the TWEAK receptor or ligand coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-TWEAK receptor or ligand fusion protein can be anchored to glutathione-agarose beads. The TWEAK receptor or ligand gene product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the TWEAK receptor and ligand gene products can be detected by measuring the amount of radioactivity that remains associated with the glutathione-agarose beads. A successful inhibition of the interaction by the test compound will result in a decrease in measured radioactivity.

Alternatively, a GST-TWEAK receptor gene fusion protein and TWEAK ligand gene product (or vice versa) can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the TWEAK receptor-ligand gene product interaction can be detected by adding the labeled antibody and measuring the radioactivity associated with the beads.

In another embodiment of the invention, these same techniques can be employed using peptide fragments that correspond to the binding domains of the TWEAK receptor and/or ligand protein, in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized.

For example, and not by way of limitation, a TWEAK receptor or ligand gene product can be anchored to a solid material as described, above, in this Section by making a GST-TWEAK receptor or ligand fusion protein and allowing it to bind to glutathione agarose beads. The interactive binding partner obtained can be labeled with a radioactive isotope, such as <35> S, and cleaved with a proteolytic enzyme such as trypsin. Cleavage products can then be added to the anchored GST-TWEAK receptor fusion protein or TWEAK ligand fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

The TWEAK receptor-ligand interactions of the invention, in vivo, initiate a cascade of events that either stimulate or suppress angiogenesis in a target group of cell or tissue. Molecules, such as nucleic acid molecules, proteins, or small molecules may, in turn, influence this cascade. Compounds that disrupt the TWEAK receptor-ligand interaction effects in this way may be useful in regulating angiogenesis.

The basic principle of the assay systems used to identify compounds that interfere with the angiogenic or anti-angiogenic effect of TWEAK receptor-ligand interaction involves preparing a reaction mixture containing the TWEAK receptor and ligand under conditions and for a time sufficient to allow the two to interact and bind, thus forming a complex. In order to test a compound for inhibitory activity of the effect of this interaction, the reaction mixture is prepared in the presence and absence of the test compound. The test compound may be initially included in the reaction mixture, or may be added at a time subsequent to the addition of the TWEAK receptor-ligand complex. Control reaction mixtures are incubated without the test compound or with a placebo. The inhibition or potentiation of any effect of the TWEAK complex on vascularization is then detected. Normal angiogenic response in the control reaction, but not in the reaction mixture containing the test compound, indicates that the compound interferes with the cascade of events initiated by the TWEAK receptor-ligand interaction. Enhanced angiogenesis in the test compounds-containing culture indicates a stimulator of the TWEAK receptor-ligand complex effect.

The following examples are intended to illustrate particular embodiments and do not to limit the scope of the invention.

EXAMPLE 1

This example presents the cloning and identification of the TWEAK Receptor.

Expression Cloning of TWEAK Receptor cDNA

To clone TWEAK Receptor cDNA, an expression vector encoding a growth hormone leader, a leucine zipper multimerization domain, and the C-terminal extracellular domain of human TWEAK (see Chicheportiche et al., J. Biol. Chem. 272(51):32401, 1997) was constructed. This expression vector, which was named pDC409-LZ-TWEAK, comprised the DNA sequence SEQ ID NO:1 and encoded the polypeptide SEQ ID NO:2. pDC409-LZ-TWEAK conditioned supernatants were produced by transient transfection into CV1-EBNA cells. These supernatants were incubated with magnetic beads coated with polyclonal goat anti-mouse antibody that had previously been incubated with a mouse monoclonal antibody against the leucine zipper. Control beads were produced by mixing the coated beads with supernatants from cells transfected with empty vector.

A monolayer of COS cells grown in a T175 flask was transfected with 15 µg of DNA pools of complexity of 100,000 from a HUVEC cDNA expression library. After 2 days these cells were lifted from the flask, and incubated in 1.5 mls of binding media plus 5% non-fat dried milk for 3 hours at 4 degrees C. on a rotator wheel. Cells were pre-cleared by adding control beads and rotated at 4 degrees C. for an additional 45 minutes after which bead bound cells were removed with a magnet. Pre-clearing was repeated 2-3 times, then TWEAK coated beads were added to the cells and rotated 30 minutes at 4 degrees C. Cells binding the TWEAK beads were separated by use of a magnet and washed 4× in PBS. Plasmid DNA was extracted from these cells by lysing in 0.1% SDS, and electroporating the supernatants in DH101B cells. Colonies were grown overnight on ampicilin selective media. Transformants were pooled and used as a source of plasmid DNA for a further round of panning. After 2 rounds of panning, positive clones were picked from the resulting pool based on their ability to bind TWEAK using a slide binding protocol like that described in Part B, below.

The human TWEAK receptor (also called TWEAKR) cDNA was determined to have the sequence SEQ ID NO:3, which encodes a 129 residue polypeptide (SEQ ID NO:4). Examination of the sequence predicts a polypeptide having an approximately 78 amino acid extracellular domain (residues 1-78 of SEQ ID NO:4, including the signal peptide), an approximately 23 amino acid transmembrane domain (residues 79-101 of SEQ ID NO:4), and an approximately 28 amino acid intracellular domain (residues 102-129 of SEQ ID NO:4). TWEAKR is the smallest known TNF receptor family member. It has a single cysteine-rich repeat region in the extracellular domain, as compared to the 3-4 repeats of other TNF receptor family members. The TWEAKR polypeptide was previously described as a transmembrane protein encoded by a human liver cDNA clone (WO 98/55508, see also WO 99/61471), but had not been identified as the TWEAK receptor. A murine homolog, the FGF-inducible Fn14 (Meighan-Mantha et al., J. Biol. Chem. 274(46):33166, 1999), is approximately 82% identical to the human protein, as shown by the alignment in FIG. 1.

The newly identified TWEAK receptor was tested side by side with DR3 (which had been identified as the TWEAK receptor by Marsters et al., Current Biology 8:525, 1998) for the ability to bind to TWEAK.

B. The TWEAK Receptor Binds to TWEAK

Slides of COS cells were transfected with expression vectors containing TWEAKR, DR3, or vector without insert (control). After two days the cells were incubated with concentrated supernatants from CV-1 cells transfected with a vector encoding the leucine zipper TWEAK extracellular domain fusion protein. One hour later the cells were washed and probed with an I-125 labeled antibody against the leucine-zipper domain. The slides were washed, fixed, and autoradiography was performed using x-ray film. The TWEAKR transfected cells bound significant amounts of TWEAK. TWEAK did not bind to the cells transfected with DR3 or the control cells. This experiment confirmed that the TWEAKR polypeptide identified in part A above, rather than DR3, is the major receptor for TWEAK. After discovery of the functional TWEAK receptor, other investigators also reported that DR3 is not the major receptor for TWEAK (Kaptein et al., FEBS Lett., 485(2-3): 135, 2000. The TWEAK-TWEAKR binding interaction was further characterized by Scatchard analysis.

CV-1 cells were transfected with human full length TWEAK and mixed 1:30 with Raji cells, which do not express TWEAK. The cells were incubated with serial dilutions of 125-I labeled human TWEAK receptor-Fc for 2 hours at 4 degrees Celsius. Free and bound probe was separated by microfuging the samples through a phalate oil mixture in plastic tubes. Supernatants and pellets were gamma-counted. Scatchard analyses of TWEAK ligand binding the TWEAK receptor showed a binding affinity constant (Ka) of approximately $4.5 \times 10^8 \, M^{-1}$.

C. The TWEAK Receptor is Strongly Expressed in Cardiac Tissue

To determine the expression pattern of the TWEAK receptor, Northern blot analyses were performed. Human multiple tissue northern blots were purchased from Clontech (Palo Alto, Calif.) and probed with P-32 labeled random primed DNA from the TWEAK receptor coding region. The blots were washed and autoradiography was performed using x-ray film. Results showed that in the adult TWEAKR is strongly expressed in heart, placenta, and some skeletal muscle samples. Strong expression in heart tissue further supports the utility of TWEAKR in the diagnosis and treatment of cardiac disease. In contrast to the adult, the fetal tissues expressed TWEAKR more ubiquitously; TWEAKR transcripts were seen in the lung and liver.

EXAMPLE 2

This example presents the recombinant production of soluble TWEAK Receptor Fc (TWEAKR-Fc) fusion polypeptides.

To construct a nucleic acid encoding the TWEAKR extracellular domain fused to Fc, a nucleic acid encoding the N-terminal 79 amino acids from TWEAKR, including the leader (signal peptide), was joined to a nucleic acid encoding an Fc portion from human IgG1. Sequences for this construct are shown as SEQ ID NO:6 (nucleic acid) and SEQ ID NO:7 (amino acid). In SEQ ID NO:7, residues 1-27 are the predicted signal peptide (predicted to be cleaved upon secretion from the cell; the actual cleavage site was identified by N-terminal sequence analysis, see below), residues 28-79 are from the cysteine-rich TWEAKR extracellular domain, residues 80-81 are from a BglII cloning site, and the remainder is the Fc portion. Upon insertion into a mammalian expression vector, and expression in and secretion from a mammalian host cells, this construct produced a polypeptide designated TWEAKR-Fc. N-terminal sequence analysis determined that the secreted polypeptide designated TWEAKR-Fc had an N-terminus corresponding to residue 28 (Glu) of SEQ ID NO:7. Anti-angiogenic activity of TWEAKR-Fc was demonstrated using assays such as those described in the following examples. An analogous Fc-fusion construct was prepared using the murine TWEAKR extracellular domain.

EXAMPLE 3

This example presents a planar endothelial cell migration (wound closure) assay useful for measuring the activity of TWEAK receptor antagonists. In this assay, endothelial cell migration is measured as the rate of closure of a circular wound in a cultured cell monolayer. The rate of wound closure is linear, and is dynamically regulated by agents that stimulate and inhibit angiogenesis in vivo.

Primary human renal microvascular endothelial cells, HRMEC, were isolated, cultured, and used at the third passage after thawing, as described in Martin et al., In vitro Cell Dev Biol 33:261, 1997. Replicate circular lesions, "wounds," (600-800 micron diameter) were generated in confluent HRMEC monolayers using a silicon-tipped drill press. At the time of wounding the medium (DMEM+1% BSA) was supplemented with 20 ng/ml PMA (phorbol-12-myristate-13-acetate), EGF (4 ng/ml), and 0.150 to 5 µg/ml TWEAKR-Fc, or a combination of 40 ng/ml EGF and 0.150 to 5 µg/ml TWEAKR-Fc. The residual wound area was measured as a function of time (0-12 hours) using a microscope and image analysis software (Bioquant, Nashville, Tenn.). The relative migration rate was calculated for each agent and combination of agents by linear regression of residual wound area plotted over time. The results are shown in FIGS. 2-3.

Figure 3:
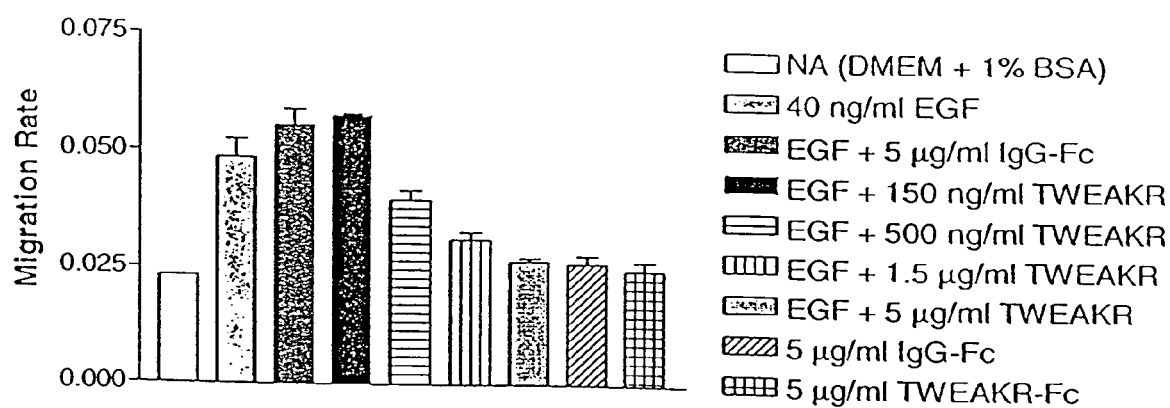
FIG. 3 shows the effect of TWEAKR-Fc on EGF-induced HRMEC wound closure.

Compared to huIgG or media+BSA, TWEAKR-Fc inhibited PMA-induced endothelial migration in a dose responsive manner, reducing the rate of migration to unstimulated levels at 5 µg/ml (FIG. 2). Neither huIgG nor TWEAKR-Fc inhibited basal (uninduced) migration. When HRMEC migration was induced by EGF, TWEAKR-Fc inhibited endothelial migration in a dose-dependent manner, reducing the rate of migration to unstimulated levels at 5 µg/ml (FIG. 3).

EXAMPLE 4

This example presents a mouse corneal pocket assay useful for measuring the activity of TWEAK receptor antagonists. In this assay, agents to be tested for angiogenic or anti-angiogenic activity are immobilized in a slow release form in a hydron pellet, which is implanted into micropockets created in the corneal epithelium of anesthetized mice. Vascularization is measured as the appearance, density, and extent of vessel ingrowth from the vascularized corneal limbus into the normally avascular cornea.

Hydron pellets, as described in Kenyon et al., Invest Opthamol. & Visual Science 37:1625, 1996, incorporated sucralfate with bFGF (90 ng/pellet), bFGF and IgG (14 µg/pellet, control), or bFGF and TWEAKR-Fc (14 µg). The pellets were surgically implanted into corneal stromal micropockets created by micro-dissection 1 mm medial to the lateral corneal limbus of 6-8 week old male C57BL mice. After five days, at the peak of neovascular response to bFGF, the corneas were photographed, using a Zeiss slit lamp, at an incipient angle of 35-50° from the polar axis in the meridian containing the pellet. Images were digitized and processed by subtractive color filters (ADOBE® PHOTOSHOP® 4.0) to delineate established microvessels by hemoglobin content. Image analysis software (Bioquant, Nashville, Tenn.) was used to calculate the fraction of the corneal image that was vascularized, the vessel density within the vascularized area, and the vessel density within the total cornea.

As shown in Table 1, TWEAKR-Fc (100 pmol) inhibited bFGF (3 pmol)-induced corneal angiogenesis, reducing the vascular density to 50% of that induced by FGF alone or FGF+IgG.

TABLE 1

Effect of TWEAKR-Fc on FGF-induced Angiogenesis in the Mouse Corneal Pocket Assay

| Treatment | Greater than 50% Reduction in Number and Length of Vessels n/total n (%) |
| --- | --- |
| FGF alone | 0/2 (0%) |
| FGF + IgG | 0/2 (0%) |
| FGF + TWEAKR-Fc | 6/9 (67%) |

EXAMPLE 5

This example presents an endothelial cell proliferation assay useful for measuring the activity of a TWEAK receptor antagonist. In this assay, endothelial cell proliferation is measured after 4 days of cell growth in microtiter wells using a cell labeling molecule called calcein AM. Esterases expressed by the cells cleave the calcein and cause it to fluoresce when excited at 485 nm. Uncleaved calcein does not fluoresce. The amount of fluorescence is directly related to the number of endothelial cells in the culture well. Endothelial cell proliferation is often regulated by agents that stimulate and/or inhibit angiogenesis in vivo.

Primary HUVEC (human umbilical vein endothelial cells) were obtained from a commercial source (Clonetics, Walkersville, Md.), cultured, and used at passage 2 to 7. Replicate cultures were set up by adding 3000 HUVEC to each microtiter well in endothelial cell basal media (EBM, an endothelial cell basal media that contains no growth factors or serum and is based on the media formulations developed by Dr. Richard Ham at the University of Colorado, Clonetics) plus 0.05% FBS (fetal bovine serum). At the time of culture initiation FGF-2 (fibroblast growth factor-2, 10 ng/ml) or human TWEAK (100 ng/ml) was added to the cultures in the presence of human IgG (huIgG, control) or human TWEAKR-Fc at concentrations ranging from 0.08 µg/ml to 20 µg/ml (0.25 to 20 µg/ml for TWEAK-induced and 0.08 to 6.7 µg/ml for FGF-2-induced). The HUVEC containing cultures were incubated for 4 days at 37 degrees C., 5% $CO_2$. On the fourth day of culture 4 µM calcein-AM was added to the cultures and 2 hours later the wells were evaluated for fluorescence. The results, expressed as the average fluorescence (485-530 nm) counts for replicate wells plus or minus the SEM, are shown in FIGS. 4 and 5.

Figure 4:
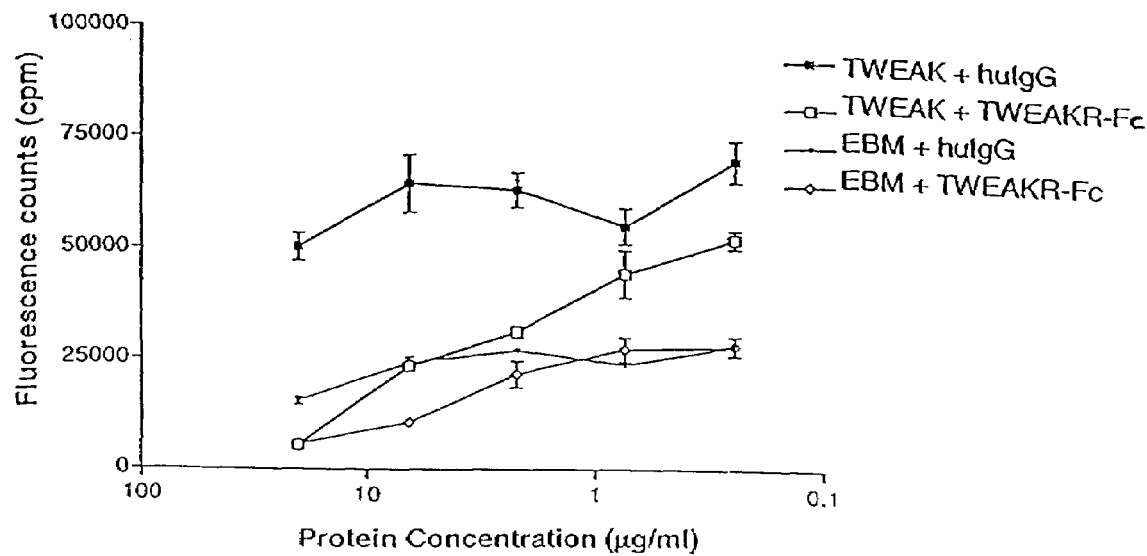
FIG. 4 shows the effect of human TWEAKR-Fc on TWEAK-induced (100 ng/ml) HUVEC proliferation.
Figure 5:
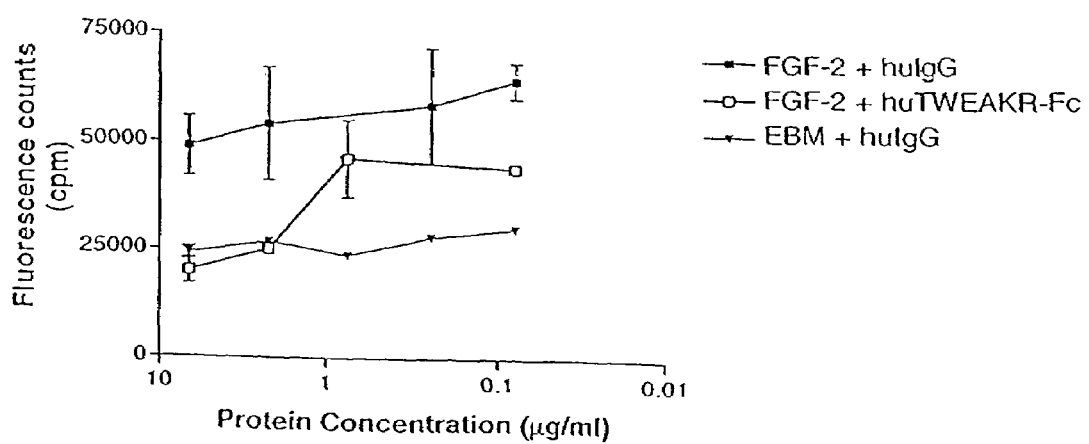
FIG. 5 shows the effect of human TWEAKR-Fc on FGF-2-induced (10 ng/ml) HUVEC proliferation.

TWEAKR-Fc specifically inhibited TWEAK-induced HUVEC proliferation in a dose-dependent manner when compared to huIgG which did not effect TWEAK-induced proliferation (FIG. 4). In addition, TWEAKR-Fc inhibited the basal proliferation of HUVEC observed during culture in EBM plus 0.05% FBS, as compared to huIgG which did not. Interestingly, TWEAKR-Fc also inhibited FGF-2 mediated HUVEC proliferation at concentrations of greater than 2 µg/ml, as compared to huIgG which did not effect the FGF-2 induced HUVEC proliferative response (FIG. 5). These results show that TWEAKR-Fc inhibits HUVEC proliferation induced by the addition of exogenous recombinant human TWEAK. That TWEAKR-Fc partially inhibits serum-induced HUVEC-proliferation indicates HUVEC produce endogenous TWEAK that promotes growth/survival of the EC (endothelial cell) via the TWEAKR. TWEAKR-Fc attenuation of FGF-2 induced proliferation indicates that at least part of the EC response to FGF-2 is dependent on endogenous TWEAK/TWEAKR interaction.

EXAMPLE 6

This example presents a murine cardiac ischemia/engraftment model useful for measuring the activity of aTWEAK receptor antagonist.

Survival of heterotopically transplanted cardiac tissue from one mouse donor to the ear skin of another genetically similar mouse requires adequate neovascularization by the transplanted heart and the surrounding tissue, to promote survival and energy for cardiac muscle function. Inadequate vasculature at the site of transplant causes excessive ischemia to the heart, tissue damage, and failure of the tissue to engraft. Agents that antagonize factors involved in endothelial cell migration and vessel formation can decrease angiogenesis at the site of transplant, thereby limiting graft tissue function and ultimately engraftment itself. A murine heterotopic cardiac isograft model is used to demonstrate the effects of TWEAKR antagonists, including antibodies and TWEAKR-Fc, on neovascularization.

Female BALB/c (≈12 weeks of age) recipients are given neonatal heart grafts from donor mice of the same strain. The donor heart tissue is grafted into the left ear pinnae of the recipient on day 0 and the mice are divided into two groups. The control group receives human IgG (Hu IgG) while the other group receives the TWEAKR antagonist, both intraperitoneally. The treatments are continued for five consecutive days. The functionality of the grafts is determined by monitoring visible pulsatile activity on days 7 and 14 post-engraftment. The inhibition of functional engraftment, as a function of the dose of TWEAKR antagonist, is determined. The histology of the transplanted hearts is examined is order to visualize the effects of the TWEAKR antagonist on edema at the site of transplant and host and donor tissue vasculature (using, e.g., Factor VIII staining).

EXAMPLE 7

This example presents a method of treating tumors with a TWEAK receptor antagonist.

TWEAKR antagonists are tested in animal models of solid tumors. The effect of the TWEAKR antagonists is determined by measuring tumor frequency and tumor growth.

EXAMPLE 8

This example presents an ELISA-based assay useful for determining the binding properties of TWEAK binding molecules, for example, monomeric and multimeric TWEAKR- Fc oligomers. For this example, huTWEAKR:Fc (SEQ ID NO:7), di-TWEAKR:Fc (SEQ ID NO:11), tri-TWEAKR:Fc (SEQ ID NO:13) and TWEAKR:DR5:Fc (SEQ ID NO:9) were used.

Ninety-six well LINBRO®/TITERTEK™ enzyme immunoassay plates (ICN Biochemicals, Aurora, Ohio) were coated with TWEAKR:Fc (SEQ ID NO:7) at a concentration of 1 mg/ml in PBS, 50 µl/well, plate sealer applied, and incubated overnight at 4° C. Each well was washed three times with PBST (PBS+0.1% TWEEN 20; 200 µl/well, then incubated for one hour at 37° C. in PBST+3% nonfat dry milk (NFDM).

In separate reactions, FLAG-tagged TWEAK (TWEAK-FLAG) was pre-incubated with each of the above TWEAKR polypeptides at ambient temperature for 30 min., in DMEM+ 0.5% low Ig serum, in 96 well U-bottom plates at a final concentration of TWEAK-FLAG of 50 ng/ml and a final concentration of each TWEAKR polypeptide of from 9,000 to 4 ng/ml, in 3-fold serial dilutions.

The EIA plate was again washed three times with PBST+ 3% NFDM. 50 µl/well of ligand/receptor mixture was added, incubated at ambient temperature for 30 min., then washed three times with PBST+3% NFDM.

FLAG-M2 biotinylated antibody, diluted 1:500 in PBST+ 3% NFDM, was added at 50 µl/well, incubated for 45 min. at ambient temperature, and washed three times with PBST+3% NFDM.

SA-HRP, diluted 1:2000 in PBST+3% NFDM, was added at 50 µl/well, then incubated for 45 min. at ambient temperature.

The plates were washed five times, 100 µl/well 3,3',5,5'-tetramethylbenzidine (TMB) was added, and the plates were incubated at ambient temperature for 5-20 minutes.

The reaction was stopped with 50 µl/well of 1M $H_3PO_4$ and absorbances read at $A_{450/570}$.

Figure 6:
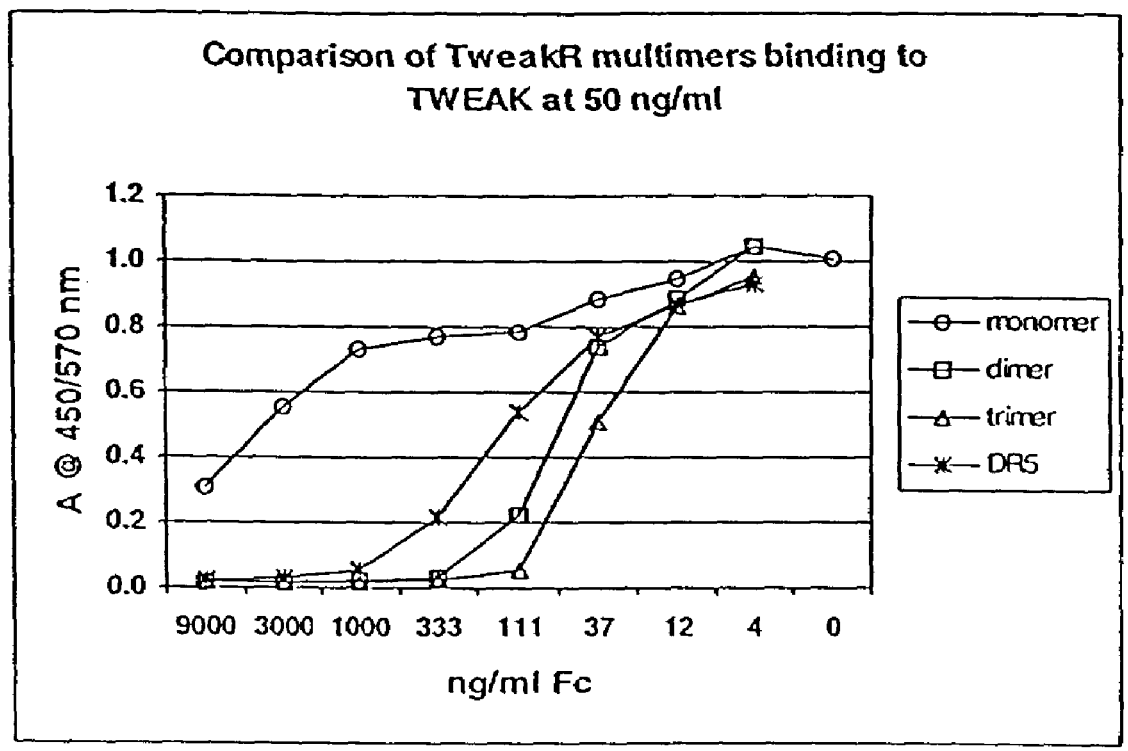
FIG. 6 shows the binding of TWEAKR:Fc (SEQ ID NO:7; "monomer"), TWEAKR:DR5:Fc (SEQ ID NO:9, "DR5"), di-TWEAKR:Fc (SEQ ID NO:11, "dimer"), and tri-TWEAKR:Fc (SEQ ID NO:13, "trimer") to TWEAK-FLAG in an ELISA binding assay.

As shown in FIG. 6, TWEAKR:Fc showed the weakest binding, followed by TWEAKR:DR5:Fc, then di-TWEAKR:Fc (SEQ ID NO:11), then tri-TWEAKR:Fc (SEQ ID NO:13). Thus, the more soluble TWEAKR domains the fusion protein comprised, the stronger it bound to TWEAK. Moreover, the increase in binding was more than additive, as shown by the difference in binding between TWEAKR:Fc and di-TWEAKR:Fc.

EXAMPLE 9

This example presents a competition binding assay using Europium labeled TWEAKR:Fc useful for determining the binding properties of TWEAK binding molecules, for example, monomeric and multimeric TWEAKR-Fc oligomers. For this example, huTWEAKR:Fc (SEQ ID NO:7), di-TWEAKR:Fc (SEQ ID NO:11), tri-TWEAKR:Fc (SEQ ID NO:13) and TWEAKR:DR5:Fc (SEQ ID NO:9) were used.

M2 anti-flag antibody was diluted to a concentration of 4 µg/ml in 0.1M $NaHCO_3$. 100 µl/well was used to coat 96 well flat bottom plates. Plate sealer was applied and the plates were incubated at 4° C. overnight.

Each well was washed five times with PBST (PBS+0.1% TWEEN 20), then 200 µl/well of PBST+3% NFDM was added. The plates were incubated for one hour at 37° C., then washed five times with PBST.

FLAG-TWEAK was diluted to 50 ng/ml in PBS and added to 100µl/well. The plates were incubated at ambient temperature, with shaking, for one hour. The plates were washed five more times in PBST.

Unlabeled and europium labeled receptors were pre-mixed in 96 well U-bottom plates, diluted in PBST+3% NFDM to a final concentration of 35ng/ml for europium-labled TWEAKR, three fold dilutions of unlabeled receptors, to final concentrations of 9000-12ng/ml.

To each well was added 100µl of pre-mixed receptors. Plates were incubated for one hour at ambient temperature with shaking, then washed ten times as before. 100µl/well of enhancement solution (Perkin Elmer, 1244-105) was added and the plates were incubated for five minutes with shaking. Absorbances were read at $A_{615}$ on a Wallac plate reader.

Figure 7:
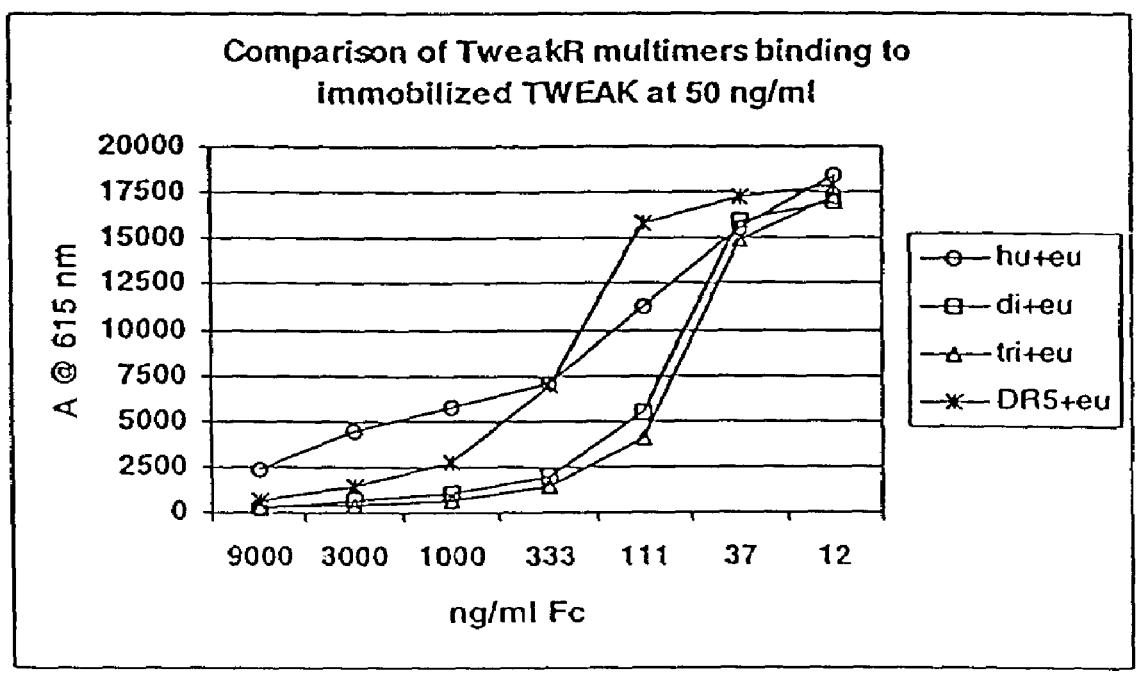
FIG. 7 shows the ability of TWEAKR:Fc (SEQ ID NO:7; "hu+eu"), TWEAKR:DR5:Fc (SEQ ID NO:9, "DR5+eu"), di-TWEAKR:Fc (SEQ ID NO:11, "di+eu"), and tri-TWEAKR:Fc (SEQ ID NO:13, "tri+eu") to compete with europium labeled TWEAKR for binding to TWEAK in a competition binding assay.

As shown in FIG. 7, monomeric TWEAKR showed the poorest ability to compete with europium labeled TWEAKR:Fc for binding to TWEAK, followed by dimeric TWEAKR and trimeric TWEAKR.

EXAMPLE 10

This example presents an ELISA-style assay useful for determining the binding properties of TWEAK binding molecules, for example, monomeric and multimeric TWEAKR-Fc oligomers.

TWEAKR:Gly5:Fc (SEQ ID NO:15) is a fusion protein comprising an N-terminal methionine residue, residues 29 through 70 of the TWEAK receptor, five glycine residues, and an Fc fragment-derived peptide. TWEAKR:1KPEG:Fc (SEQ ID NO:17) is a fusion protein comprising an N-terminal methionine residue, residues 29 through 70 of the TWEAK receptor, a linker, and an Fc fragment-derived peptide. TWEAKR:1KPEG:TWEAKR:Gly5:Fc (SEQ ID NO:18) is a fusion protein comprising an N-terminal methionine residue, residues 29 through 70 of the TWEAK receptor, a linker, residues 29 through 70 of the TWEAK receptor, five glycine residues, and an Fc fragment-derived peptide. TWEAKR:Gly5:TWEAKR:Gly5:Fc (SEQ ID NO:19) is a fusion protein comprising an N-terminal methionine residue, residues 29 through 70 of the TWEAK receptor, five glycine residues, residues 29 through 70 of the TWEAK receptor, five glycine residues, and an Fc fragment-derived peptide.

Figure 8:
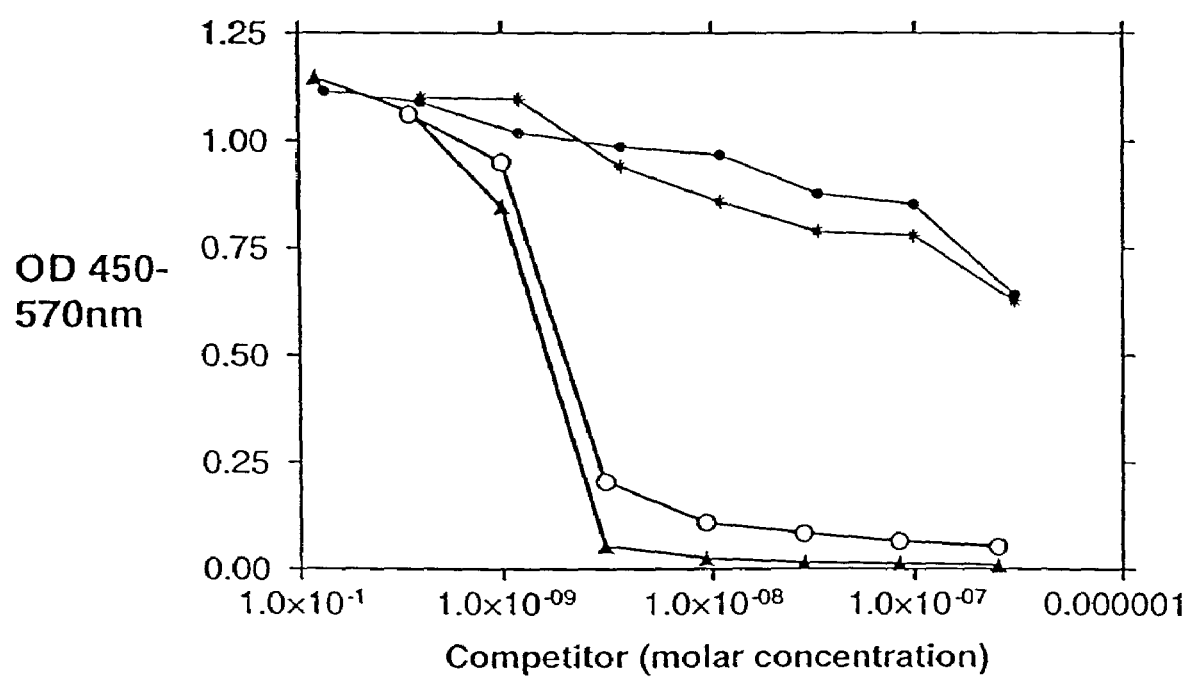
FIG. 8 shows the binding of TWEAKR:Gly5:Fc (SEQ ID NO:15; black circles), TWEAKR:1KPEG:Fc (SEQ ID NO:17, asterisks), TWEAKR:1KPEG:TWEAKR:Gly5:Fc (SEQ ID NO:18; black triangles), and TWEAKR:Gly5:TWEAKR:Gly5:Fc (SEQ ID NO:19; white circles) to TWEAK using an ELISA-style assay.
Figure 9:
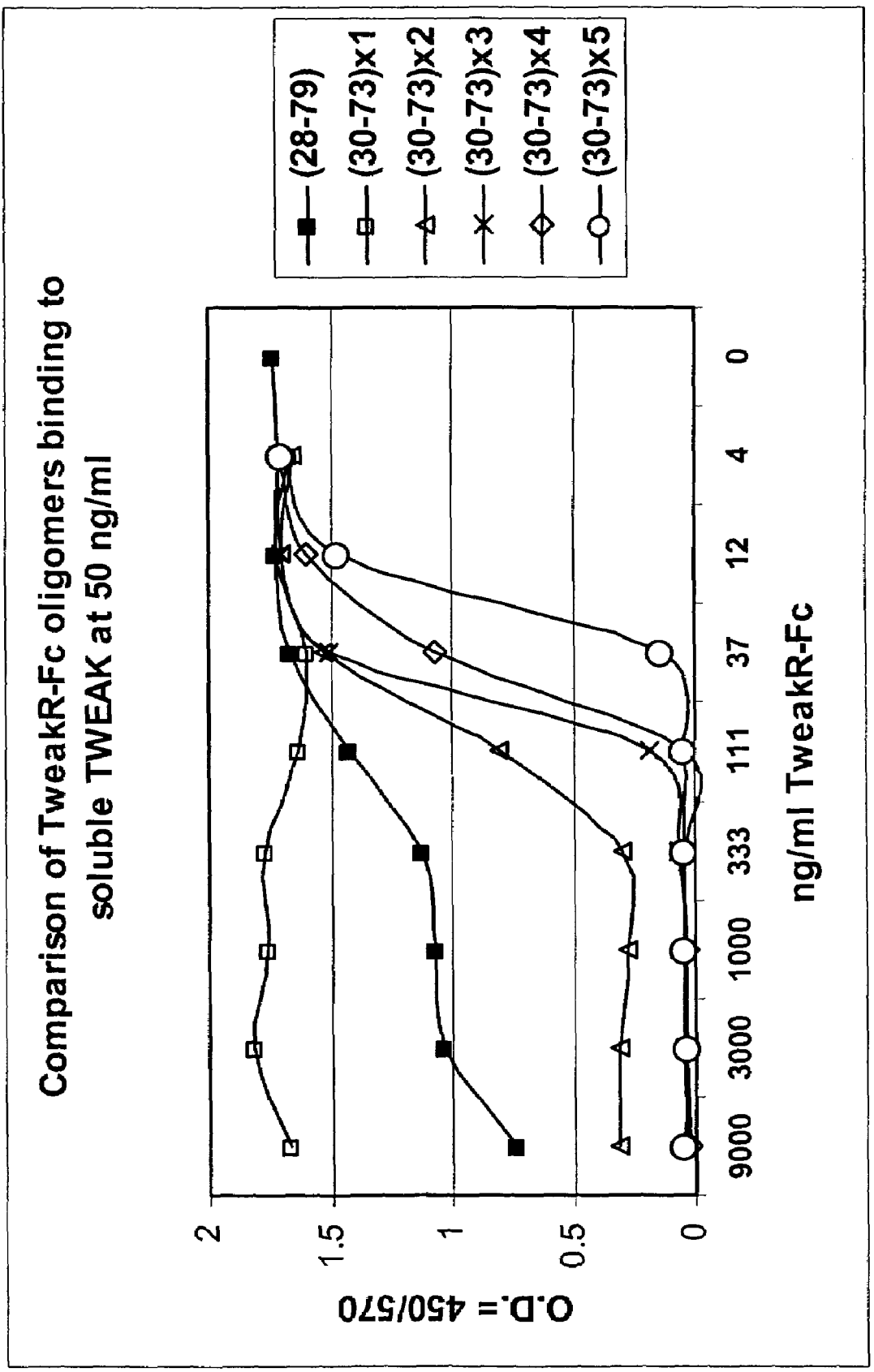
FIG. 9 shows a comparison of TweakR-Fc oligomers binding to soluble TWEAK at 50 ng/ml using huTWEAKR:Fc (SEQ ID NO:7) (black squares), TWEAKR 43 monomer (SEQ ID NO:31) (white squares), TWEAKR 43 dimer (SEQ ID NO:33) (white triangles), TWEAKR 43 trimer (SEQ ID NO:35) (crosses), TWEAKR 43 tetramer (SEQ ID NO:37) (white diamonds), and TWEAKR 43 pentamer (SEQ ID NO:39) (white circles).
Figure 10:
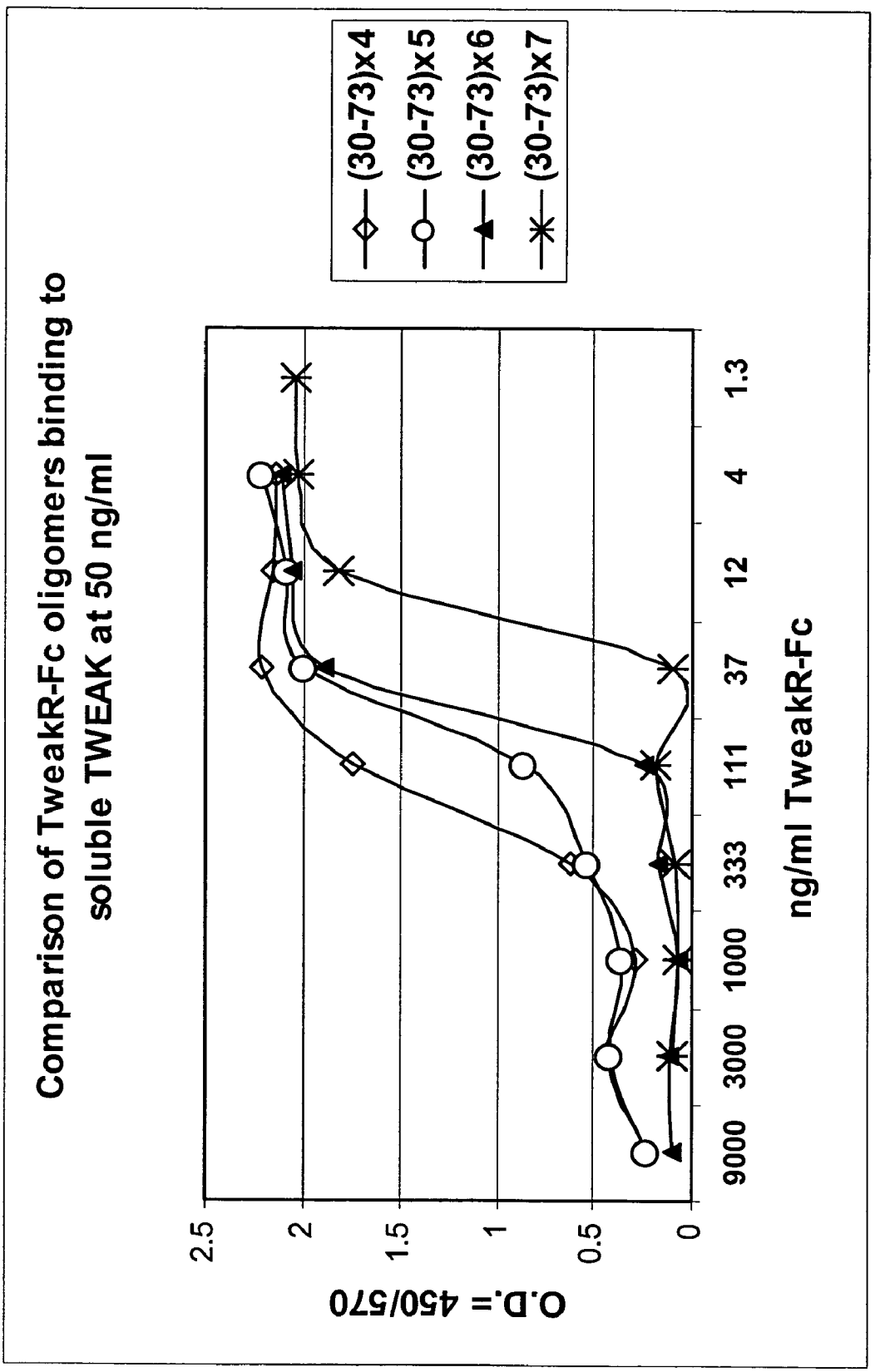
FIG. 10 shows a comparison of TweakR-Fc oligomers binding to soluble TWEAK at 50 ng/ml using TWEAKR 43 tetramer (SEQ ID NO:37) (white diamonds), TWEAKR 43 pentamer (SEQ ID NO:39) (white circles), TWEAKR 43 hexamer (SEQ ID NO:41) (white triangles), and TWEAKR 43 heptamer (SEQ ID NO:43) (asterisks).
Figure 11:
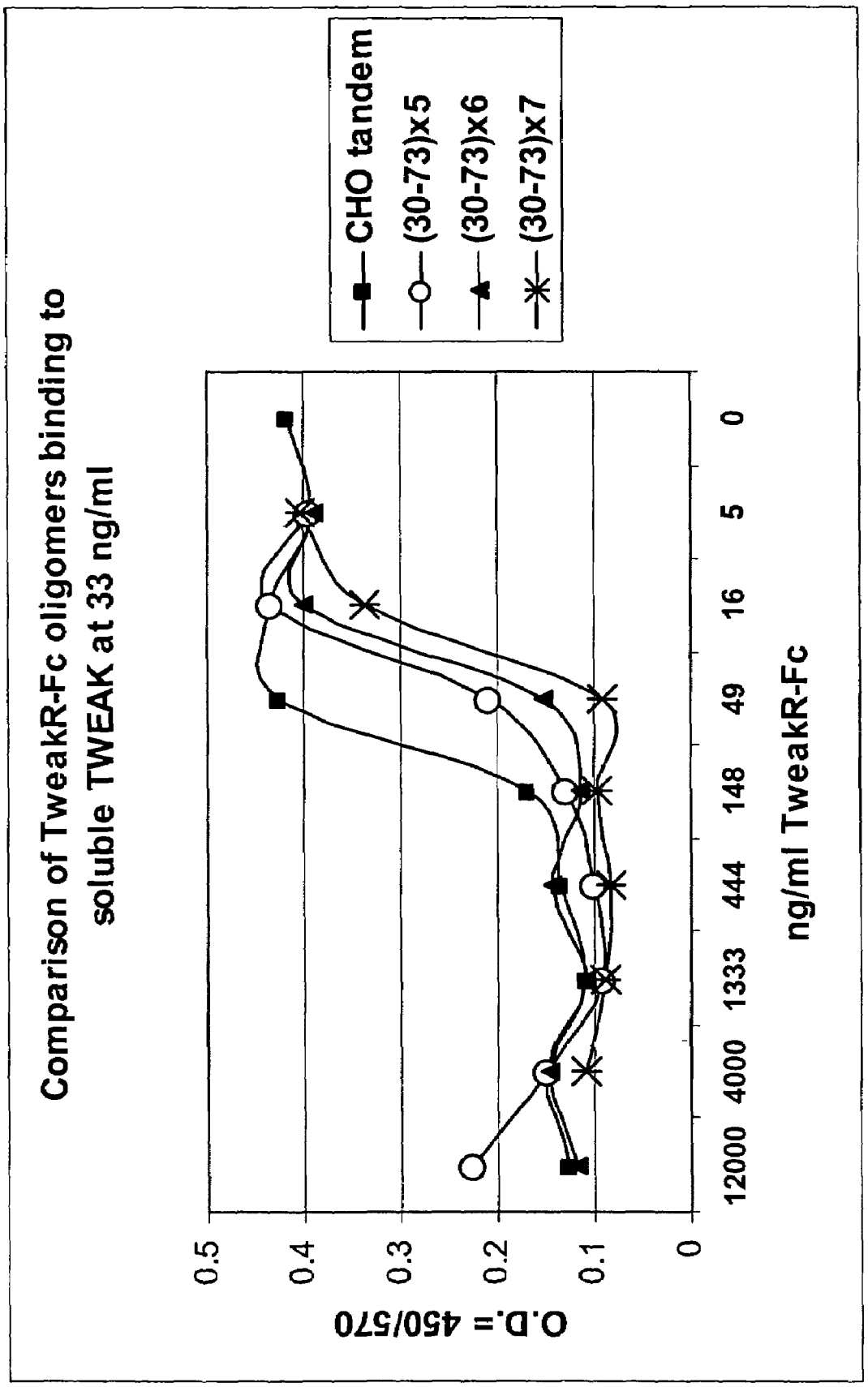
FIG. 11 shows a comparison of TweakR-Fc oligomers binding to soluble TWEAK at 33 ng/ml using CHO TANDEM (SEQ ID NO:19 expressed in stably transfected CHO cells), TWEAKR 43 pentamer (SEQ ID NO:39) (white circles), TWEAKR 43 hexamer (SEQ ID NO:41) (white triangles), and TWEAKR 43 heptamer (SEQ ID NO:43) (asterisks).
Figure 12:
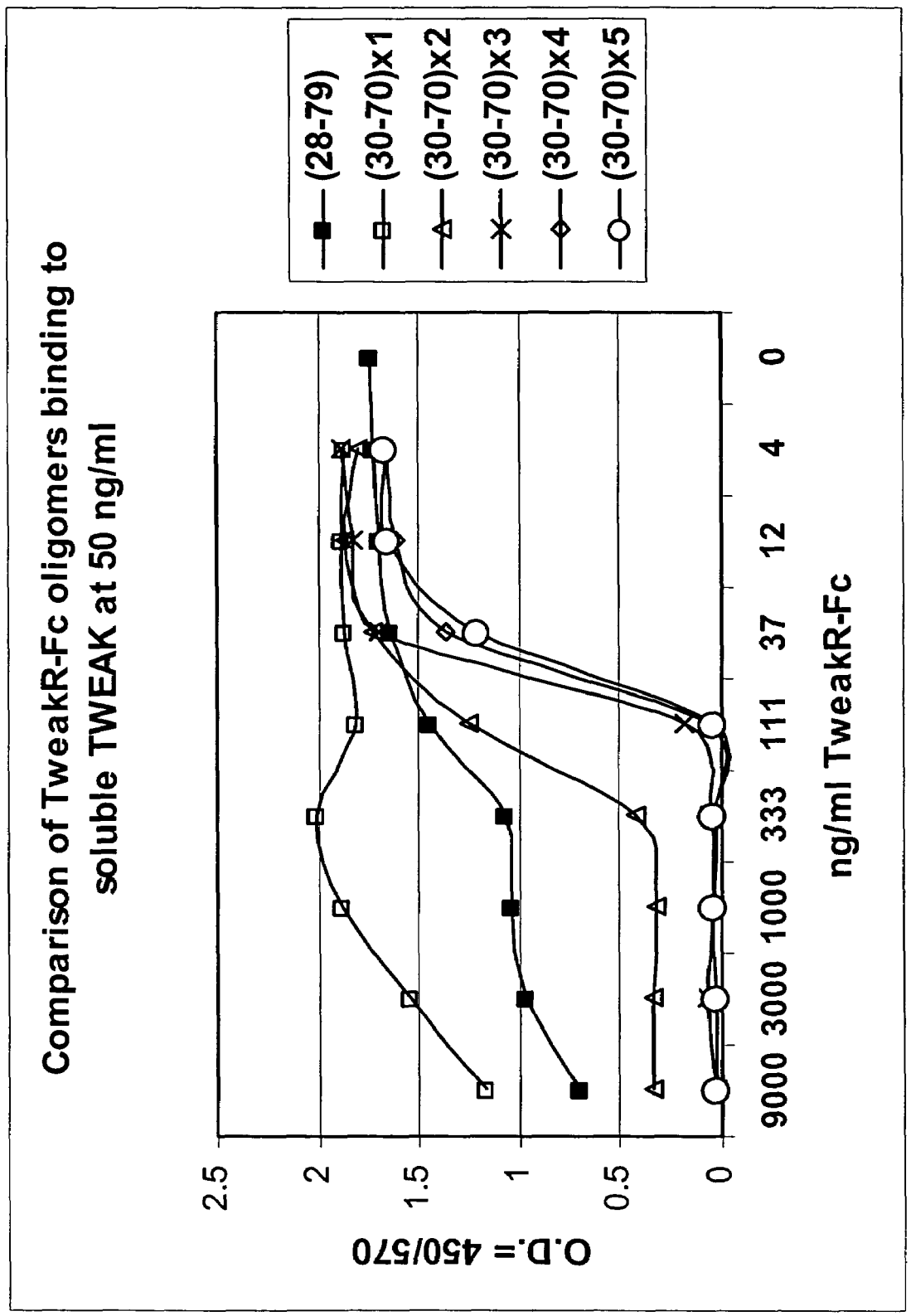
FIG. 12 shows a comparison of TweakR-Fc oligomers binding to soluble TWEAK at 50 ng/ml using huTWEAKR:Fc (SEQ ID NO:7) (black squares), TWEAKR 40 monomer (SEQ ID NO:21) (white squares), TWEAKR 40 dimer (SEQ ID NO:23) (white triangles), TWEAKR 40 trimer (SEQ ID NO:25) (crosses), TWEAKR 40 tetramer (SEQ ID NO:27) (white diamonds), and TWEAKR 40 pentamer (SEQ ID NO:29) (white circles).

Using an ELISA-style assay similar to that described in Example 8, it was determined that monomeric oligomers (TWEAKR:Gly5:Fc and TWEAKR:1KPEG:Fc) bind to TWEAK about equally well, but much less well than dimeric oligomeric constructs (TWEAKR:1KPEG:TWEAKR:Gly5:Fc and TWEAKR:Gly5:TWEAKR:Gly5:Fc) (FIG. 8).

EXAMPLE 11

This example presents the results of an ELISA-based TWEAK-binding assay using huTWEAKR:Fc (SEQ ID NO:7), TWEAKR 40mono-3 (SEQ ID NO:21), TWEAKR 40dimer-1 (SEQ ID NO:23), TWEAKR 40trimer-5 (SEQ ID NO:25), TWEAKR 40quad-2 (SEQ ID NO:27), TWEAKR 40quint-1 (SEQ ID NO:29), TWEAKR 43mono-F4 (SEQ ID NO:31), TWEAKR 43dimer-F2 (SEQ ID NO:33), TWEAKR 43trimer-1 (SEQ ID NO:35), TWEAKR 43quad-2 (SEQ ID NO:37), TWEAKR 43quint-3 (SEQ ID NO:39), TWEAKR 43hex-1 (SEQ ID NO:41), and TWEAKR 43sept-1 (SEQ ID NO:43). The protocol described in Example 8 was used except that in the present example BSA was omitted from the wash buffers. The results are presented in FIGS. 9-12.

EXAMPLE 12

Figure 13:
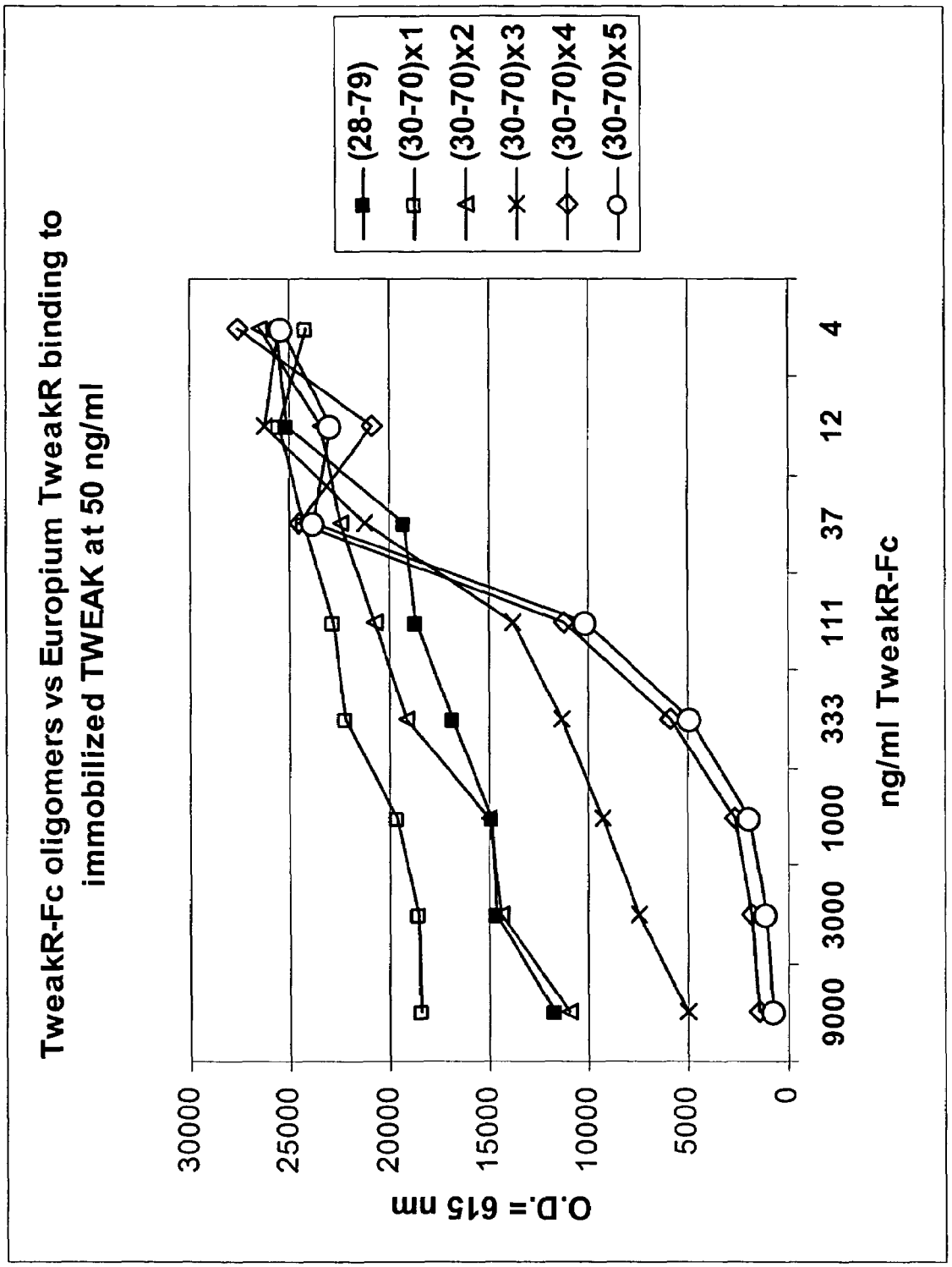
FIG. 13 shows a comparison of TweakR-Fc oligomers vs Europium TweakR binding to immobilized TWEAK at 50 ng/ml using huTWEAKR:Fc (SEQ ID NO:7) (black squares), TWEAKR 40 monomer (SEQ ID NO:21) (white squares), TWEAKR 40 dimer (SEQ ID NO:23) (white triangles), TWEAKR 40 trimer (SEQ ID NO:25) (crosses), TWEAKR 40 tetramer (SEQ ID NO:27) (white diamonds), TWEAKR 40 pentamer (SEQ ID NO:29) (white circles).
Figure 14:
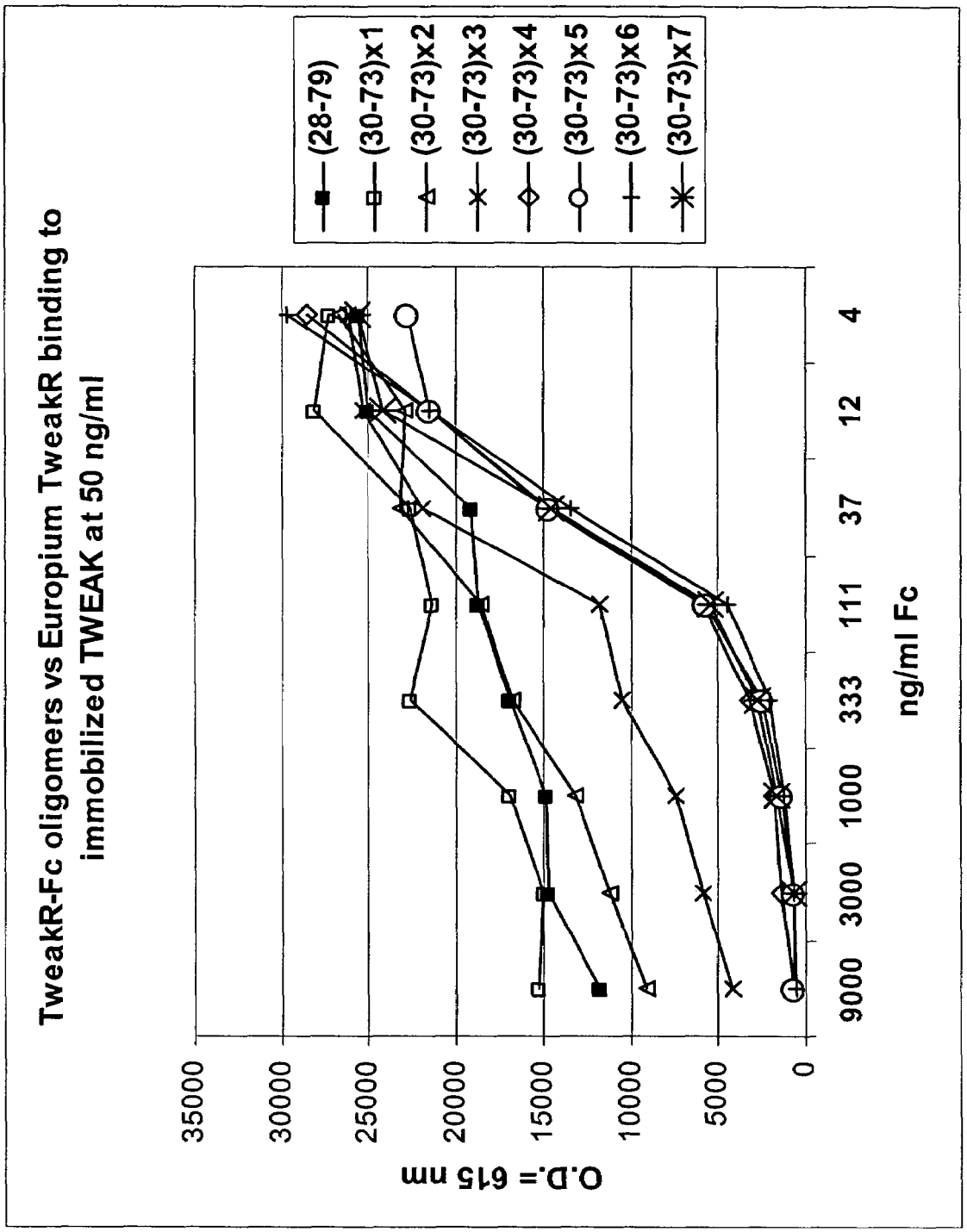
FIG. 14 shows a comparison of TweakR-Fc oligomers vs Europium TweakR binding to immobilized TWEAK at 50 ng/ml using huTWEAKR:Fc (SEQ ID NO:7) (black squares), TWEAKR 43 monomer (SEQ ID NO:31) (white squares), TWEAKR 43 dimer (SEQ ID NO:33) (white triangles), TWEAKR 43 trimer (SEQ ID NO:35) (crosses), TWEAKR 43 tetramer (SEQ ID NO:37) (white diamonds), TWEAKR 43 pentamer (SEQ ID NO:39) (white circles), TWEAKR 43 hexamer (SEQ ID NO:41) (vertical lines), and TWEAKR 43 heptamer (SEQ ID NO:43) (asterisks).

This example presents the results of a competition binding assay using Europium labeled TWEAKR:Fc as described in Example 9. In the present example, huTWEAKR:Fc (SEQ ID NO:7), TWEAKR 40mono-3 (SEQ ID NO:21), TWEAKR 40dimer-1 (SEQ ID NO:23), TWEAKR 40trimer-5 (SEQ ID NO:25), TWEAKR 40quad-2 (SEQ ID NO:27), TWEAKR 40quint-1 (SEQ ID NO:29), TWEAKR 43mono-F4 (SEQ ID NO:31), TWEAKR 43dimer-F2 (SEQ ID NO:33), TWEAKR 43trimer-1 (SEQ ID NO:35), TWEAKR 43quad-2 (SEQ ID NO:37), TWEAKR 43quint-3 (SEQ ID NO:39), TWEAKR 43hex-1 (SEQ ID NO:41), and TWEAKR 43sept-1 (SEQ ID NO:43) were used. The results are presented in FIGS. 13 and 14.

The relevant disclosures of publications cited herein are specifically incorporated by reference. The examples presented above are not intended to be exhaustive or to limit the scope of the invention. The skilled artisan will understand that variations and modifications and variations are possible in light of the above teachings, and such modifications and variations are intended to be within the scope of the invention.

I claim:

1. A polypeptide consisting of a first peptide sequence, a second peptide sequence, an oligomerization domain, and optionally one or more linkers, wherein said polypeptide binds to TWEAK, and said first peptide sequence and said second peptide sequence each independently consists of a sequence that is at least 95% identical to a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 70 of the amino acid sequence of SEQ ID NO:7.

2. The polypeptide of claim 1, wherein said first peptide sequence consists of a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 70 of the amino acid sequence of SEQ ID NO:7.

3. The polypeptide of claim 1, wherein said first peptide sequence and said second peptide sequence each independently consists of a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 10 of the amino acid sequence of SEQ ID NO:7.

4. A polypeptide consisting of a first peptide sequence, a second peptide sequence, a third polypeptide sequence, an oligomerization domain, and optionally one or more linkers, wherein said polypeptide binds to TWEAK, and said first peptide sequence, second peptide sequence, and third peptide sequence each independently consists of a sequence that is at least 95% identical to a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 70 of the amino acid sequence of SEQ ID NO:7.

5. The polypeptide of claim 4, wherein said first peptide sequence, second peptide sequence, and third peptide sequence each independently consists of a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 70 of the amino acid sequence of SEQ ID NO:7.

6. A polypeptide consisting of a first peptide sequence, a second peptide sequence, a third polypeptide, a fourth peptide sequence, an oligomerization domain, and optionally one or more linkers, wherein said polypeptide binds to TWEAK, and said first peptide sequence, second peptide sequence, third peptide sequence, and fourth peptide sequence each independently consists of a sequence that is at least 95% identical to a sequence selected from the group consisting of:
   a. residues 29 through 70 of the amino acid sequence of SEQ ID NO:7;
   b. residues 30 through 73 of the amino acid sequence of SEQ ID NO:7; and
   c. residues 30 through 70 of the amino acid sequence of SEQ ID NO:7.

7. The polypeptide of claim 6, wherein said first peptide sequence, second peptide sequence, third peptide sequence, and fourth peptide sequence each independently consists of a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

8. A polypeptide consisting of a first peptide sequence, a second peptide sequence, a third polypeptide, a fourth peptide sequence, a fifth peptide sequence, an oligomerization domain, and optionally one or more linkers, wherein said polypeptide binds to TWEAK, and said first peptide sequence, second peptide sequence, third peptide sequence, fourth peptide sequence, and fifth peptide sequence each independently consists of a sequence that is at least 95% identical to a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

9. The polypeptide of claim 8, wherein said first peptide sequence, second peptide sequence, third peptide sequence, fourth peptide sequence, and fifth peptide sequence each independently consists of a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

10. A polypeptide consisting of a first peptide sequence, a second peptide sequence, a third polypeptide, a fourth peptide sequence, a fifth peptide sequence, a sixth peptide sequence, an oligomerization domain, and optionally one or more linkers, wherein said polypeptide binds to TWEAK, and said first peptide sequence, second peptide sequence, third peptide sequence, fourth peptide sequence, fifth peptide sequence, and sixth peptide sequence each independently consists of a sequence that is at least 95% identical to a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

11. The polypeptide of claim 10, wherein said first peptide sequence, second peptide sequence, third peptide sequence, fourth peptide sequence, fifth peptide sequence, and sixth peptide sequence each independently consists of a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

12. A polypeptide consisting of a first peptide sequence, a second peptide sequence, a third polypeptide, a fourth peptide sequence, a fifth peptide sequence, a sixth peptide sequence, a seventh peptide sequence, an oligomerization domain, and optionally one or more linkers, wherein said polypeptide binds to TWEAK, and said first peptide sequence, second peptide sequence, third peptide sequence, fourth peptide sequence, fifth peptide sequence, sixth peptide sequence, and seventh peptide sequence each independently consists of a sequence that is at least 95% identical to a sequence selected from the group consisting of:
  a. residues 29 through 70 of the amino acid sequence of SEQ ID NO:7;
  b. residues 30 through 73 of the amino acid sequence of SEQ ID NO:7; and
  c. residues 30 through 70 of the amino acid sequence of SEQ ID NO:7.

13. The polypeptide of claim 12, wherein said first peptide sequence, second peptide sequence, third peptide sequence, fourth peptide sequence, fifth peptide sequence, sixth peptide sequence, and seventh peptide sequence each independently consists of a sequence selected from the group consisting of:
  a. residues 29 trough 70 of the amino acid sequence of SEQ ID NO:7;
  b. residues 30 through 73 of the amino acid sequence of SEQ ID NO:7; and
  c. residues 30 trough 70 of the amino acid sequence of SEQ ID NO:7.

14. The polypeptide of claim 1, wherein said oligomerization domain comprises a leucine zipper.

15. The polypeptide of claim 1, wherein said oligomerization domain comprises a fragment of an antibody.

16. The polypeptide of claim 15, wherein said fragment of an antibody comprises an fragment domain.

17. A protein comprising a first polypeptide of claim 1 and a second polypeptide of claim 1, wherein said first and second polypeptides are oligomerized to each other.

18. The protein of claim 17 wherein the amino acid sequence of said first polypeptide is identical to the amino acid sequence of said second polypeptide.

19. The protein of claim 17 wherein the amino acid sequence of said first polypeptide is not identical to the amino acid sequence of said second polypeptide.

20. A method of inhibiting a TWEAK receptor in a subject in need thereof, comprising administering to said subject the polypeptide of claim 1.

21. A method of inhibiting angiogenesis in a subject in need thereof, comprising administering to said subject a therapeutically effective amount of a composition comprising the polypeptide of claim 1.

22. The method of claim 21 wherein said composition further comprises a pharmaceutically acceptable carrier.

23. The method of claim 21 wherein said subject is a mammal.

24. The method of claim 23 wherein said mammal is a human.

25. The method of claim 21 wherein said subject has a disease or condition mediated or exacerbated by angiogenesis.

26. The method of claim 25 wherein said disease or condition is characterized by ocular neovascularization.

27. The method of claim 25 wherein said disease or condition is a solid tumor.

28. The method of claim 27 wherein said method further comprises treating said subject with radiation.

29. The method of claim 27 wherein said method further comprises treating said subject with a second chemotherapeutic agent.

30. The method of claim 29 wherein said second chemotherapeutic agent is selected from the group consisting of: an alkylating agent, an antimetabolite, a vinca alkaloid, a plant-derived chemotherapeutic, a nitrosourea, an antitumor antibiotic, an antitumor enzyme, a topoisomerase inhibitor, a platinum analog, an adrenocortical suppressant, a hormone, a hormone agonist, a hormone antagonist, an antibody, an immunotherapeutic, a blood cell factor, a radiotherapeutic, and a biological response modifier.

31. The method of claim 29 wherein said second chemotherapeutic agent is selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, vinblastine, a lymphokine, a cytokine, an interleukin, an interferon, alpha interferon, beta interferon, delta interferon, TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, and fluoxymesterone.

32. The method of claim 25 wherein said disease or condition is an inflammatory disease or condition.

33. The method of claim 32 wherein said method further comprises treating said subject with a second therapeutic agent.

34. The method of claim 33 wherein said second therapeutic agent inhibits a cytokine or a cytokine receptor that promotes inflammation.

35. The method of claim 34 wherein said second therapeutic agent comprises a soluble fragment of said cytokine receptor, an antibody that binds said cytokine, or an antibody that binds said cytokine receptor.

36. The method of claim 33 wherein said second therapeutic agent activates a receptor that inhibits inflammation.

37. The method of claim 33 wherein said second therapeutic agent is selected from the group consisting of Flt3 ligand, CD40 ligand, interleukin-2, an interleukin-4 antagonist, an IL-13 antagonist, interleukin-12, 4-1BB ligand, an anti-4-1BB antibody, a TNF antagonist, a TNF receptor antagonist, TRAIL, a CD148 agonist, a VEGF antagonist a VEGF receptor antagonist, an IgE antagonist, and a Tek antagonist.

* * * * *